United States Patent
Lessene et al.

(10) Patent No.: US 8,962,830 B2
(45) Date of Patent: Feb. 24, 2015

(54) PROTEIN KINASE INHIBITORS AND METHODS OF TREATMENT

(75) Inventors: Guillaume Laurent Lessene, Parkville (AU); Jonathan Bayldon Baell, Parkville (AU); Antony Wilks Burgess, Camberwell (AU); Hiroshi Maruta, Brunswick West (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 0 days.

(21) Appl. No.: 13/809,369

(22) PCT Filed: Jul. 8, 2011

(86) PCT No.: PCT/AU2011/000858
§ 371 (c)(1),
(2), (4) Date: Mar. 29, 2013

(87) PCT Pub. No.: WO2012/003544
PCT Pub. Date: Jan. 12, 2012

(65) Prior Publication Data
US 2013/0184274 A1 Jul. 18, 2013

Related U.S. Application Data

(60) Provisional application No. 61/362,739, filed on Jul. 9, 2010.

(51) Int. Cl.
*C07D 487/00* (2006.01)
*A61K 31/519* (2006.01)
*C07D 487/04* (2006.01)

(52) U.S. Cl.
CPC ............ *C07D 487/04* (2013.01); *A61K 31/519* (2013.01)
USPC ........................................ 544/262; 514/262.1

(58) Field of Classification Search
None
See application file for complete search history.

(56) References Cited

U.S. PATENT DOCUMENTS

2007/0293516 A1   12/2007   Knight et al.

FOREIGN PATENT DOCUMENTS

| WO | WO 02/076986 A1 | 10/2002 |
| WO | WO 02/080926 A1 | 10/2002 |
| WO | WO 2008/039218 A2 | 4/2008 |
| WO | WO 2010/009342 A2 | 1/2010 |
| WO | WO 2011/046964 A2 | 4/2011 |

OTHER PUBLICATIONS

International Search Report and Written Opinion for PCT/AU2011/000858, mailed on Aug. 24, 2011 (11 pages).
International Preliminary Report on Patentability for PCT/AU2011/000858, mailed Jan. 15, 2013 (6 pages).
Apsel, B. et al., "Targeted polypharmacology: discovery of dual inhibitors of tyrosine and phosphoinositide kinases," *Nature Chemical Biology* 4(11):691-699, 2008.

*Primary Examiner* — Nyeemah A Grazier
(74) *Attorney, Agent, or Firm* — Cooley LLP

(57) ABSTRACT

The present invention relates to chemical compounds of formula (I) and methods for their use and preparation. In particular, the invention relates to substituted pyrazolo[3,4-d]pyrimidine based compounds which can be used in treating proliferative disorders, use of these compounds in methods of therapy and the manufacture of medicaments as well as compositions containing these compounds.

(I)

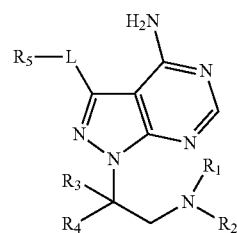

22 Claims, No Drawings

PROTEIN KINASE INHIBITORS AND METHODS OF TREATMENT

FIELD OF THE INVENTION

The present invention relates generally to chemical compounds and methods for their use and preparation. In particular, the invention relates to substituted pyrazolo[3,4-d]pyrimidine based compounds which can be used in treating proliferative disorders, use of these compounds in methods of therapy and the manufacture of medicaments as well as compositions containing these compounds.

BACKGROUND OF THE INVENTION

Tyrosine protein kinases (TPKs) are able to catalyse the transfer of the terminal phosphate of adenosine triphosphate to tyrosine residues in protein substrates. TPK are a subgroup of the larger protein kinase class of enzymes. The enzymes' ability to phosphorylate is an important mechanism in signal transduction for the regulation of cellular activity. Cellular proliferation in thought to rely (at least to some extent) on TKRs. Mutations can cause some TPKs to become constitutively active, and this aberrant activity has been thought to contribute to initiation or progression of proliferative disorders such as cancer. Accordingly, in relation to the treatment of diseases and conditions characterised by the proliferation of cells the TPK subgroup of enzymes represents an attractive target.

A family of proto-oncogenic TPKs referred to herein as SFKs (Src family kinases) have provided researchers with a better understanding of the mechanism of cancer as a disease state where normally healthy cellular signalling is disrupted. SFKs have been observed to play a critical role in cell adhesion, invasion, proliferation, survival and angiogenesis during tumour development.

SFKs comprise nine family members that share similar structure and function. The nine members are c-Src, Yrk, Yes, Fyn, Fgr, Lyn, Lck, Hck, and Blk. The overexpression or high activation of these SFKs has been observed in many tumours.

SFKs can interact with tyrosine kinase receptors, such as the EGFR and the VEGF receptor. SFKs are thought to affect cell proliferation through the Ras/ERK/MAPK pathway and may regulate gene expression via transcription factors such as STAT molecules. SFKs like some other TPKs can also affect cell adhesion and migration. The SFKs are thought to act via interaction with integrins, actins, GTPase-activating proteins, scaffold proteins, such as p130$^{CAS}$ and paxillin, and kinases such as focal adhesion kinases. Furthermore, SFKs have also been shown to regulate angiogenesis via gene expression of angiogenic growth factors, such as VEGF, interleukin 8, and fibroblast growth factor.

Due to this recognition and better understanding as to role being played by TPKs in general and SFKs in particular, small-molecule SFK inhibitors are being developed for the treatment of hyperproliferative disorders such as cancer. At this stage however of a number of promising SFK inhibitors (e.g., Bosutinib, AZ0530, and Desatinib as shown below) only Desatinib is approved whereas the others are presently still undergoing clinical trials and as such there is no guarantee that any further acceptable SFK inhibitor (based on the currently recognised compounds) will reach the market.

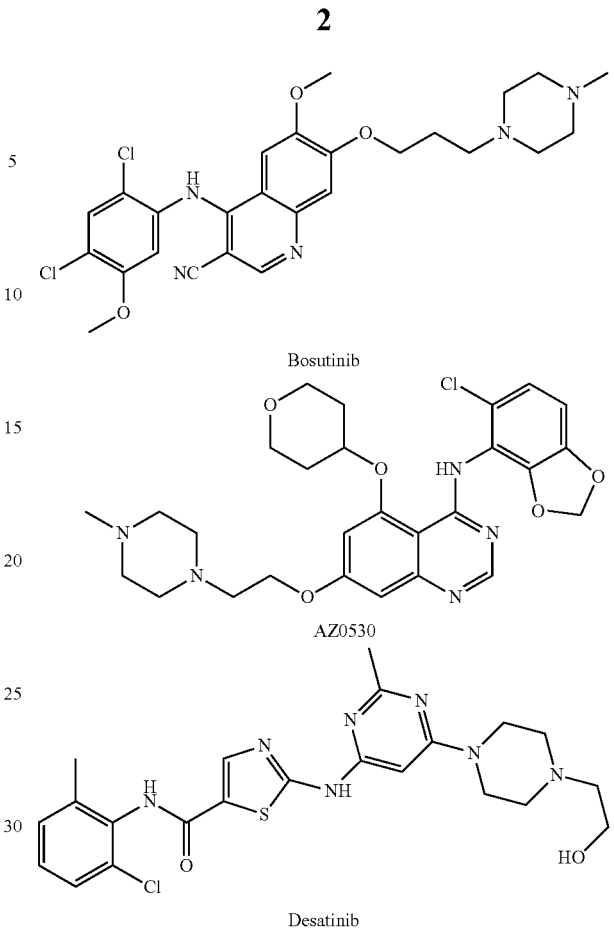

Bosutinib

AZ0530

Desatinib

SUMMARY OF INVENTION

In one aspect the invention provides compounds of formula (I) or salts thereof,

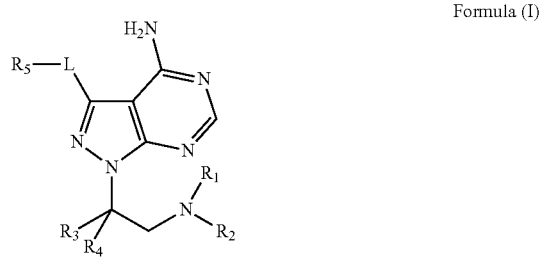

Formula (I)

wherein:
  $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;
  $R_2$ is selected from hydrogen and $C_1$-$C_3$ alkyl;
  $R_3$ and $R_4$ are independently $C_1$-$C_3$ alkyl;
  L is selected from a bond, —O—, —S—, —N(R$_9$)—, optionally substituted alkylene, —N(R$_9$)C(X')—N(R$_{9'}$)—, where each of R$_9$ and R$_{9'}$ is independently hydrogen or $C_1$-$C_4$ alkyl;

$R_5$ is selected from optionally substituted aryl, optionally substituted heteroaryl, optionally substituted heterocyclyl, and optionally substituted cycloalkyl;

X and X' are independently selected from O, S and $NR_7$;

$R_6$ is selected from optionally substituted $C_1$-$C_6$ alkyl, optionally substituted $C_1$-$C_6$ alkoxy, optionally substituted $C_2$-$C_6$alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;

$R_7$ is selected from hydrogen, cyano, optionally substituted $C_1$-$C_6$ alkyl, optionally substituted aryl, $S(O)_2R_8$, and optionally substituted aminoacyl; and $R_8$ is selected from optionally substituted $C_1$-$C_6$ alkyl and optionally substituted aryl.

In a further aspect the invention provides pharmaceutical compositions comprising a compound of formula (I) or a salt thereof, together with at least one pharmaceutically acceptable adjuvant, carrier or diluent.

In a further aspect the invention provides a method of treating a disease or condition characterised by cell proliferation including the step of administering an effective amount of a compound of formula (I) or a salt thereof to a patient in need thereof.

In still a further aspect the invention provides the use of a compound of formula (I) or a salt thereof in the manufacture of a medicament for the treatment of a disease or condition characterised by cell proliferation, including cell hyperproliferation.

In yet a further aspect the invention also provides the use of a compound of formula (I) or a salt thereof for the treatment of a disease or condition characterised by cell proliferation, including cell hyperproliferation.

DETAILED DESCRIPTION OF THE INVENTION

The term "alkyl" as used herein refers to monovalent alkyl groups which may be straight chained or branched and preferably have from 1 to 10 carbon atoms, more preferably 1 to 6 carbon atoms and most preferably 1 to 4 carbon atoms. Examples of such alkyl groups include methyl, ethyl, n-propyl, iso-propyl, n-butyl, iso-butyl, and the like.

The term "alkylene" as used herein refers to divalent alkyl groups. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

The term "aryl" as used herein refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

The term "acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

The term "arylacyl" as used herein refers to the group —C(O)aryl where the aryl group is as described above.

The term "alkenyl" as used herein refers to a monovalent alkenyl groups which may be straight chained or branched and preferably have from 2 to 10 carbon atoms, more preferably 2 to 6 carbon atoms and most preferably 2 to 4 carbon atoms and have at least 1 and preferably from 1-2, carbon to carbon, double bonds. Examples include ethenyl (—CH═$CH_2$), n-propenyl (—$CH_2$CH═$CH_2$), iso-propenyl (—C($CH_3$)═$CH_2$), but-2-enyl (—$CH_2$CH═$CHCH_3$), and the like.

The term "alkynyl" as used herein refers to monovalent alkynyl groups which may be straight chained or branched and preferably have from 2 to 10 carbon atoms, more preferably 2 to 6 carbon atoms and most preferably 2 to 4 carbon atoms and have at least 1, and preferably from 1-2, carbon to carbon, triple bonds. Examples of alkynyl groups include ethynyl (—C≡CH), propargyl (—$CH_2$C≡CH), pent-2-ynyl (—$CH_2$C≡$CCH_2$—$CH_3$), and the like.

The term "amino" as used herein refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

The term "aminoacyl" as used herein refers to the group —C(O)NR*R* where each R* is independently hydrogen, alkyl, cycloalkyl and aryl, and where each of alkyl, aryl, and cycloalkyl, is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein, and preferably hydrogen and $C_1$-$C_4$ alkyl.

"Oxyacylamino" refers to the group —NR*C(O)OR* where each R* is independently hydrogen, alkyl, cycloalkyl, aryl, heteroaryl and heterocyclyl and where each of alkyl, cycloalkyl, aryl, heteroaryl, and heterocyclyl are as described herein, and preferably hydrogen and $C_1$-$C_4$ alkyl.

The term "cycloalkyl" as used herein refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

The term "halo" or "halogen" as used herein refers to fluoro, chloro, bromo and iodo.

"Heteroaryl" refers to a monovalent aromatic carbocyclic group, preferably of from 2 to 10 carbon atoms and 1 to 4 heteroatoms selected from oxygen, nitrogen and sulfur within the ring. The most preferred heteroatoms are nitrogen, oxygen, and sulfur. Such heteroaryl groups can have a single ring (e.g., pyridyl, pyrrolyl, imididazolyl, thienyl, or furanyl) or multiple condensed rings (e.g., indolizinyl or benzothienyl).

"Heteroarylacyl" refers to the group —C(O)heteroaryl where heteroaryl is given the meaning referred to above.

"Heteroarylthio" as used herein refers to the group —S-heteroaryl wherein the heteroaryl group is as described above.

"Heterocyclyl" as used herein refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatoms are nitrogen and oxygen. Examples of heterocyclyl groups include morpholinyl, piperidinyl and piperazinyl.

"Heterocyclylacyl" as used herein refers to the group —C(O)heterocyclyl where heterocyclyl is given the meaning referred to above.

In this specification the term "optionally substituted" is taken to mean that a group may or may not be further substituted or fused (so as to form a condensed polycyclic group) with one or more groups. Substituents may be selected from hydroxyl, acyl, alkyl, alkoxy, alkenyl, alkenyloxy, alkynyl, alkynyloxy, amino, aminoacyl, oxyacylamino, thio, arylalkyl, arylalkoxy, aryl, aryloxy, carboxyl, cycloalkyl, cyano, halogen, nitro, sulphate, phosphate, heterocyclyl, heteroaryl, heterocyclyloxy, heteroaryloxy, trihalomethyl, and trialkylsilyl.

In an embodiment L is —O—, —S—, —N(R$_9$)—, optionally substituted alkylene (preferably C$_1$-C$_3$ alkylene), or —N(R$_9$)C(X')—N(R$_9$)—, where each of R$_9$ and R$_{9'}$ is independently hydrogen or C$_1$-C$_4$ alkyl.

In an embodiment L is a bond.

In an embodiment L is a bond and R$_5$ is selected from optionally substituted aryl, optionally substituted heteroaryl, optionally substituted heterocyclyl, and optionally substituted cycloalkyl.

In an embodiment L is a bond and R$_5$ is an optionally substituted aryl or optionally substituted heteroaryl.

In an embodiment L is a bond and R$_5$ is an optionally substituted phenyl.

In an embodiment L is a bond and R$_5$ is a phenyl group substituted one to three times with substitutent groups independently selected from halo, hydroxyl, acyl, C$_1$-C$_8$ alkyl, C$_2$-C$_6$ alkenyl, C$_2$-C$_6$ alkenyloxy, amino, oxyacylamino, C$_1$-C$_8$ alkoxy, aryl, aryloxy, carboxyl, cycloalkyl, cycloalkyloxy, cyano, sulphate, phosphate, heterocyclyl, heterocyclyloxy, heteroaryl, heteroaryloxy, trihalomethyl, and trialkylsilyl.

In an embodiment L is a bond and R$_5$ is a phenyl group substituted one or two times with substituent groups independently selected from halo, hydroxyl, acyl, C$_1$-C$_8$ alkyl, C$_2$-C$_6$ alkenyl, C$_2$-C$_6$ alkenyloxy, amino, oxyacylamino, C$_1$-C$_8$ alkoxy, aryl, aryloxy, carboxyl, cycloalkyl, cycloalkyloxy, cyano, sulphate, phosphate, heterocyclyl, heterocyclyloxy, heteroaryl, heteroaryloxy, trihalomethyl, and trialkylsilyl, and preferably C$_1$-C$_4$ alkyl, hydroxy, oxyacylamino, heteroaryl, aryloxy, and halo.

In an embodiment L is a bond and R$_5$ is a phenyl group substituted with hydroxyl.

In an embodiment -LR$_5$ is

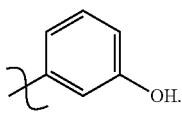

In an embodiment L is a bond and R$_5$ is a phenyl group substituted with C$_1$-C$_4$ alkoxy and —NHC(O)OC$_1$-C$_4$ alkyl.

In an embodiment -LR$_5$ is

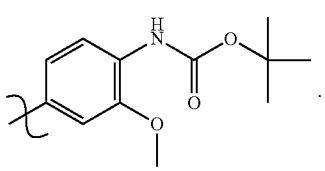 [SMILES: COc1cc(C)ccc1NC(=O)OC(C)(C)C]

In an embodiment L is a bond and R$_5$ is a phenyl group substituted with halo and hydroxy.

In an embodiment -LR$_5$ is

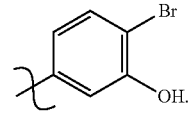

In an embodiment L is a bond and R$_5$ is a heteroaryl group.

In an embodiment -LR$_5$ is

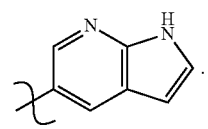

In an embodiment L is a bond and R$_5$ is a phenyl group substituted with aryloxy.

In an embodiment -LR$_5$ is

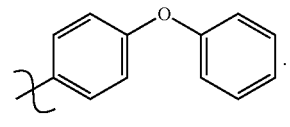

In an embodiment L is —CH$_2$— and R$_5$ is a phenyl group substituted with halo, hydroxy, and C$_1$-C$_3$ alkyl.

In an embodiment L is —CH$_2$— and R$_5$ is a phenyl group substituted with hydroxy.

In an embodiment -LR$_5$ is

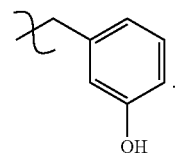

In an embodiment L is —CH$_2$— and R$_5$ is a phenyl group substituted with C$_1$-C$_3$ alkyl.

In an embodiment -LR$_5$ is

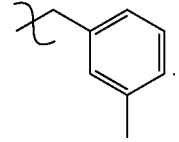

In an embodiment, L is —CH$_2$— and R$_5$ is a phenyl group substituted with chloro and C$_1$-C$_4$ alkyl.

In an embodiment $-LR_5$ is

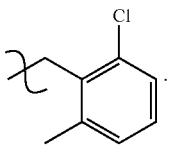

In an embodiment $-LR_5$ is phenyl.

In an embodiment L is a bond and $R_5$ is a phenyl group substituted with a substituent group selected from halo, hydroxyl, acyl, $C_1$-$C_8$ alkyl, $C_2$-$C_6$ alkenyl, $C_2$-$C_6$ alkenyloxy, amino, $C_1$-$C_8$ alkoxy, aryl, aryloxy, carboxyl, cycloalkyl, cycloalkyloxy, cyano, sulphate, phosphate, heterocyclyl, trihalomethyl, and trialkylsilyl.

In a preferred embodiment, where L is a bond and $R_5$ is a phenyl group, the substituent group, if present, is in the para position.

Accordingly, in a further aspect the invention provides compounds of formula (Ia) or salts thereof,

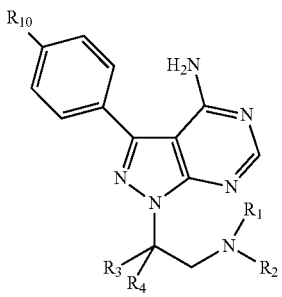

Formula (Ia)

wherein:
- $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—$R_6$;
- $R_2$ is selected from hydrogen and $C_1$-$C_3$ alkyl;
- $R_3$ and $R_4$ are independently $C_1$-$C_3$ alkyl;
- $R_{10}$ is selected from hydrogen, halo, $C_1$-$C_4$ alkyl, $C_2$-$C_4$ alkynyl, $C_2$-$C_4$ alkenyl, arylalkyl, OR$^1$ (where R$^1$ is H, $C_1$-$C_3$ alkyl or aryl), COOR$^2$ (where R$^2$ is H, $C_1$-$C_3$ alkyl or aryl), nitro, cyano, amino, trihalomethyl, thio, and thio $C_1$-$C_3$ alkyl;
- X is selected from O, S and NR$_7$;
- $R_6$ is selected from optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
- $R_7$ is selected from hydrogen, cyano, acyl, optionally substituted $C_1$-$C_6$ alkyl, optionally substituted aryl, S(O)$_2$R$_8$, and optionally substituted aminoacyl; and
- $R_8$ is selected from optionally substituted $C_1$-$C_6$ alkyl and optionally substituted aryl.

With reference to compounds of formula (I) and (Ia), preferably $R_{10}$ is $C_1$-$C_4$ alkyl or halo.

In a further preferred embodiment and with reference to compounds of formula (I) and (Ia), $R_3$ and $R_4$ are independently $C_1$-$C_3$ alkyl, and $R_{10}$ is $C_1$-$C_4$ alkyl or halo.

In a further aspect the invention provides compounds of formula (Ib) or salts thereof,

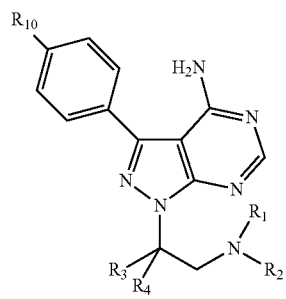

Formula (Ib)

wherein:
- $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—$R_6$;
- $R_2$ is selected from hydrogen and $C_1$-$C_3$ alkyl;
- $R_3$ and $R_4$ are independently $C_1$-$C_3$ alkyl;
- $R_{10}$ is $C_1$-$C_4$alkyl or halo;
- X is selected from O, S and NR$_7$;
- $R_6$ is selected from optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
- $R_7$ is selected from hydrogen, cyano, acyl, optionally substituted $C_1$-$C_6$ alkyl, optionally substituted aryl, S(O)$_2$R$_8$, and optionally substituted aminoacyl; and
- $R_8$ is selected from optionally substituted $C_1$-$C_6$ alkyl, and optionally substituted aryl.

In an embodiment and with reference to formula (Ia) or (Ib), $R_{10}$ is methyl or chloro.

In a further embodiment and with reference to formula (Ia) or (Ib), $R_{10}$ is methyl.

Accordingly, in a further aspect the invention provides compounds of formula (Ic) or salts thereof,

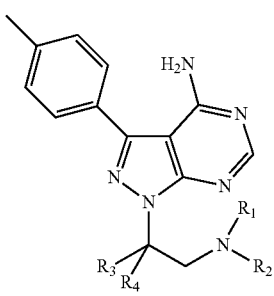

Formula (Ic)

wherein:
- $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;
- $R_2$ is selected from hydrogen and $C_1$-$C_3$ alkyl;
- $R_3$ and $R_4$ are independently $C_1$-$C_3$ alkyl;
- X is selected from O, S and NR$_7$;
- $R_6$ is selected from optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
- $R_7$ is selected from hydrogen, cyano, optionally substituted $C_1$-$C_6$ alkyl, optionally substituted aryl, S(O)$_2$R$_8$, and optionally substituted aminoacyl; and
- $R_8$ is selected from optionally substituted $C_1$-$C_6$ alkyl and optionally substituted aryl.

In an embodiment and with reference to formula (I), (Ia), (Ib) or (Ic), $R_3$ and $R_4$ are independently selected from $C_1$-$C_2$ alkyl.

In a further embodiment and with reference to formula (I), (Ia), (Ib) or (Ic), $R_3$ and $R_4$ are methyl.

Accordingly, in a further aspect the invention provides compounds of formula (Id) or salts thereof,

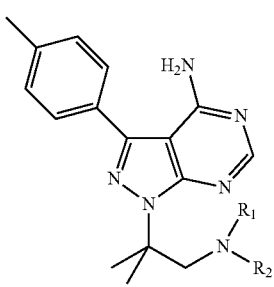

Formula (Id)

wherein:
- $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;
- $R_2$ is selected from hydrogen and $C_1$-$C_3$ alkyl;
- X is selected from O, S and NR$_7$;
- $R_6$ is selected from optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
- $R_7$ is selected from hydrogen, cyano, optionally substituted $C_1$-$C_6$ alkyl, optionally substituted aryl, S(O)$_2$R$_8$, and optionally substituted aminoacyl; and
- $R_8$ is selected from optionally substituted $C_1$-$C_6$ alkyl and optionally substituted aryl.

In an embodiment and with reference to formula (I), (Ia), (Ib), (Ic) or (Id), $R_2$ is hydrogen or methyl.

In a further embodiment and with reference to formula (I), (Ia), (Ib), (Ic) or (Id), $R_2$ is hydrogen.

Accordingly in a further aspect the invention provides compounds of formula (Ie), or salts thereof, Formula (Ie)

wherein:
- $R_1$ is selected from hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;
- X is selected from O, S and NR$_7$;
- $R_6$ is selected from optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
- $R_7$ is selected from hydrogen, cyano, optionally substituted $C_1$-$C_6$ alkyl, optionally substituted aryl, S(O)$_2$R$_8$, and optionally substituted aminoacyl; and
- $R_8$ is selected from optionally substituted $C_1$-$C_6$ alkyl and optionally substituted aryl.

In still a further embodiment and with reference to formula (I), (Ia), (Ib), (Ic), (Id) or (Ie) $R_1$ is selected from the following preferred groups:

a) hydrogen;
b) optionally substituted $C_1$-$C_6$ alkyl, and more preferably $C_1$-$C_6$ alkyl;
c) —(SO$_2$)— optionally substituted aryl or —(SO$_2$)— optionally substituted heteroaryl;
d) C(=X)—R$_6$ where X is O, S and NR$_7$, wherein R$_6$ is selected from optionally substituted alkyl, optionally substituted aryl, optionally substituted heteroaryl, optionally substituted aryl-$C_{1-3}$alkyl, optionally substituted heteroaryl-$C_{1-3}$alkyl, optionally substituted aryl-$C_{1-3}$alkoxy, optionally substituted heteroaryl-$C_{1-3}$alkoxy, trifluoroalkyl, NR'R" (where R' is hydrogen or $C_{1-3}$ alkyl, and R" is hydrogen, optionally substituted alkyl, or optionally substituted arylacyl) and R$_7$ is hydrogen, optionally substituted aryl, or optionally substituted $C_{1-3}$alkyl.

In still a further embodiment and with reference to formula (I), (Ia), (Ib), (Ic), (Id) or (Ie) R$_1$ is selected from the following preferred groups:

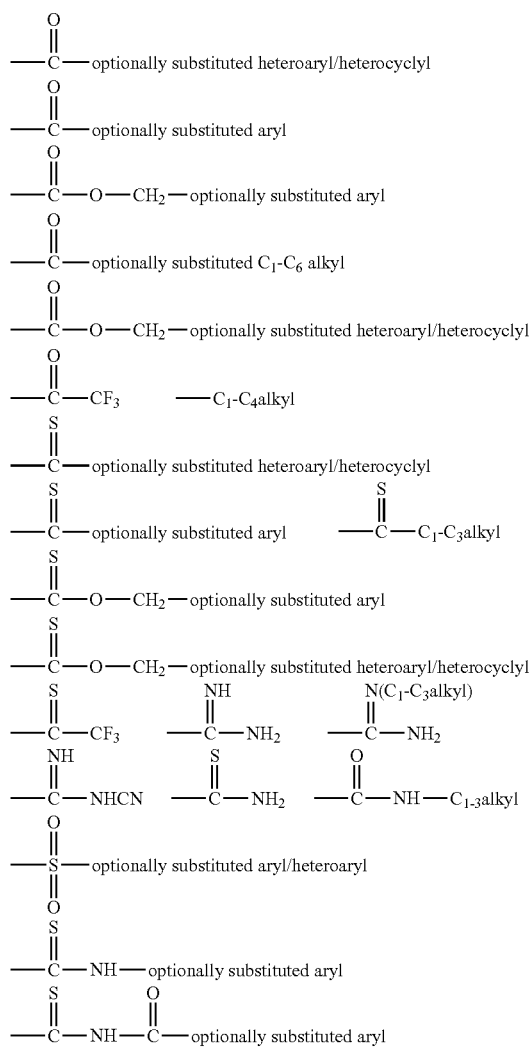

wherein heteroaryl preferably represents:
(i) a 5-membered heteroaryl group selected from pyrrole, 2H-pyrrole, furan, pyrazole, thiophene, isothiazole, thiazole, 1,2,3-triazole, 1,2,4-triazole, 1,2,3-oxadiazole, 1,2,5-oxadiazole, 1,3,4-thiadiazole, tetrazole, imidazole, oxazole, and isoxazole; or
(ii) a 6-membered heteroaryl group selected from pyridine, pyrimidine, pyrazine, and 1,3,5-triazine;

wherein heterocyclyl preferably represents:
(i) a 5-membered heterocyclyl group selected from 1-pyrroline, 2-pyrroline, 3-pyrroline, pyrrolidine, tetrahydrofuran, tetrahydrothiophene, 2-pyrazoline, 3-pyrazoline, 2-imidazoline, pyrazolidine, imidazolidine, 3-dioxolane, thiazolidine, and isoxazolidine; or
(ii) a 6-membered heterocyclyl group selected from 2H-pyran, 4H-pyran, 3,4-dihydro-2H-pyran, piperidine, 1,4-oxazine, 1,4-dioxine, piperazine, morpholine, 1H-dioxane, 1,4-thazine, thiomorpholine, 1,4-oxathane, 1,4-dithane, 1,3,5-trioxane, 6H-1,2,5-thiadiazine, 2H-1,5,2-dithiazine, and 1,3,5-trithiane;

and wherein preferably aryl is selected from phenyl, napthyl and anthracenyl;
and where the heteroaryl, heterocyclyl or aryl group may be substituted from 1 to 4 times by the group consisting of hydroxyl, acyl, $C_1$-$C_4$ alkyl, $C_1$-$C_4$ alkoxy, $C_2$-$C_6$ alkenyl, $C_2$-$C_6$ alkenyloxy, $C_2$-$C_6$ alkynyl, $C_2$-$C_6$ alkynyloxy, —O—(CH$_2$)$_n$—OH, —O—(CH$_2$)$_n$—OC$_1$-$C_3$ alkyl, —(CH$_2$)$_n$-amino, —(CH$_2$)$_n$-diC$_1$-$C_3$ alkyl amino, —(CH$_2$)$_n$-aminoacyl, —(CH$_2$)$_n$-thio, arylalkyl, —(CH$_2$)$_n$-arylalkoxy, —(CH$_2$)$_n$-aryl, —(CH$_2$)$_n$-aryloxy, —(CH$_2$)$_n$-carboxyl, —(CH$_2$)$_n$-cycloalkyl, cyano, halogen, nitro, sulphate, phosphate, —(CH$_2$)$_n$-heterocyclyl, —(CH$_2$)$_n$-heteroaryl, —(CH$_2$)$_n$-trihalomethyl, and —(CH$_2$)$_n$-trialkylsilyl, wherein n is an integer from 0-6.

In an embodiment, —C(O)-optionally substituted $C_1$-$C_6$ alkyl includes:
—C(O)—(CH$_2$)$_n$-substituent,
where n is an integer from 1 to 6
and the substituent group is selected from:
a) —NC(O)O-optionally substituted phenyl;
b) —C(O)C$_1$-$C_3$ alkyl;
c) —OC$_1$-$C_3$ alkyl;
d) —O-optionally substituted phenyl;
e) -optionally substituted phenyl;
f) —CN;
g) —O—C$_1$-$C_3$ alkylene-optionally substituted phenyl; and
h) -amino.

In a further embodiment and with reference to formula (I), (Ia), (Ib), (Ic), or (Ie), R$_1$ is C(O)R$_6$ where R$_6$ is defined above.

In a further embodiment the invention provides compounds of formula (If):

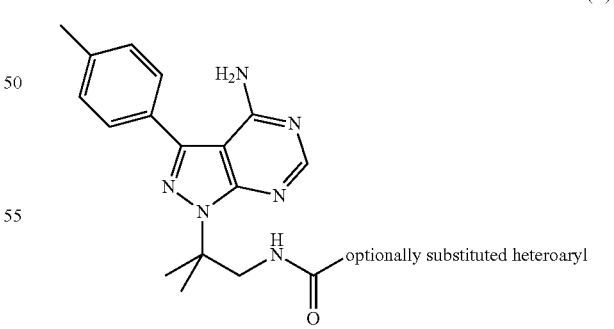

(If)

Preferably, and with reference to formula (If) compounds, the optionally substituted heteroaryl group is selected from optionally substituted pyridyl or optionally substituted thiazolyl. Preferred substituents, when present, include —(CH$_2$)$_n$-heterocyclyl, optionally substituted $C_1$-$C_4$ alkoxy and optionally substituted phenyl, where n is an integer from 0-4.

Representative compounds of the present invention include:
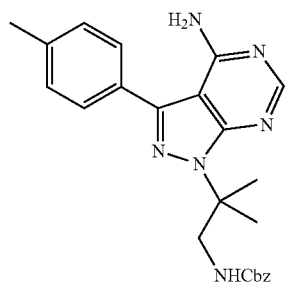
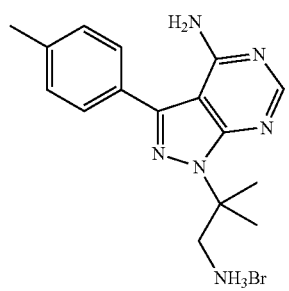
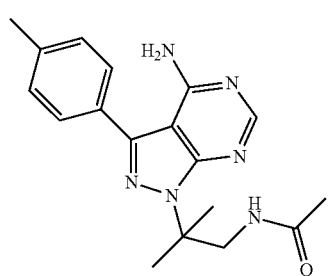
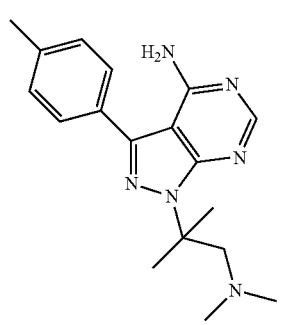
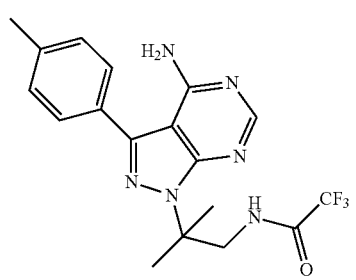
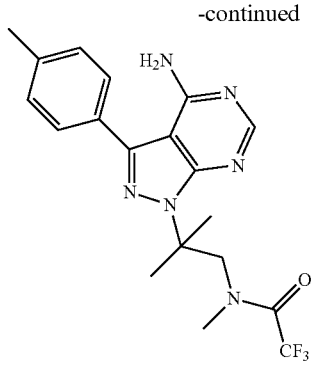
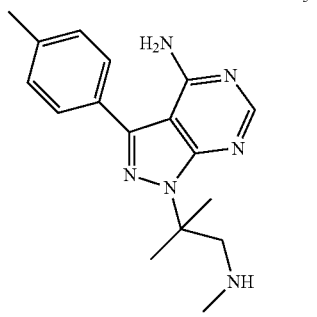
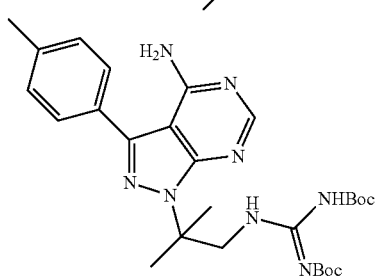
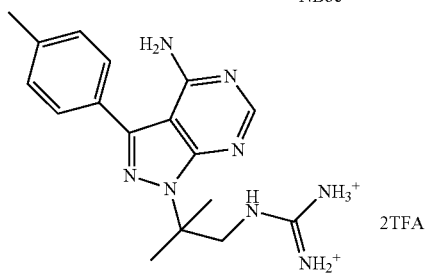
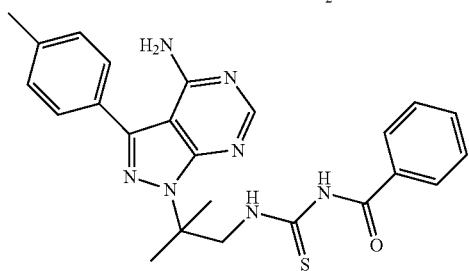
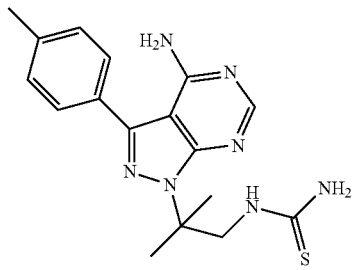

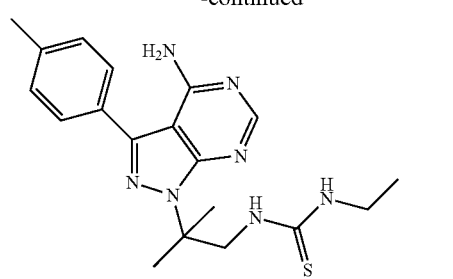
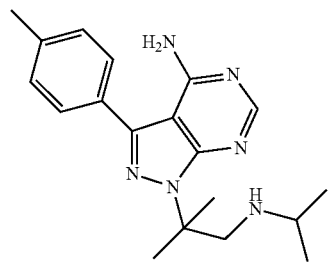
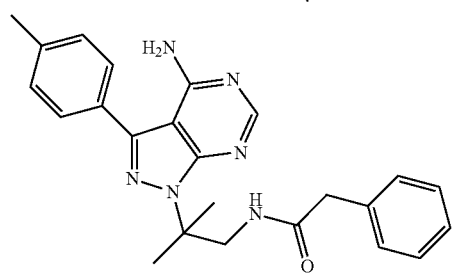
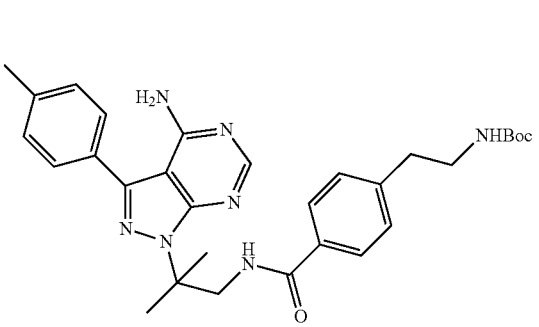
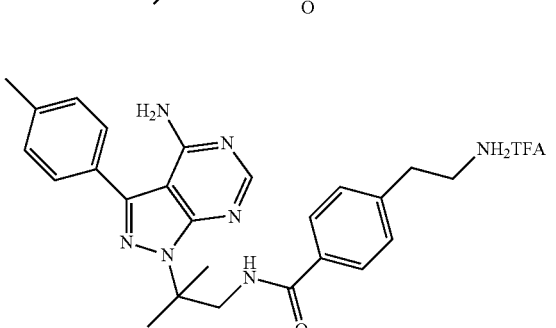
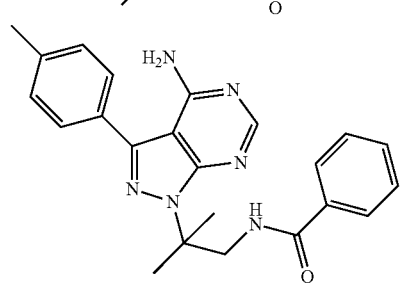
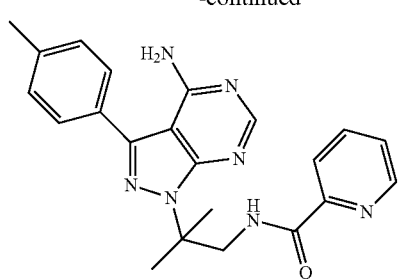
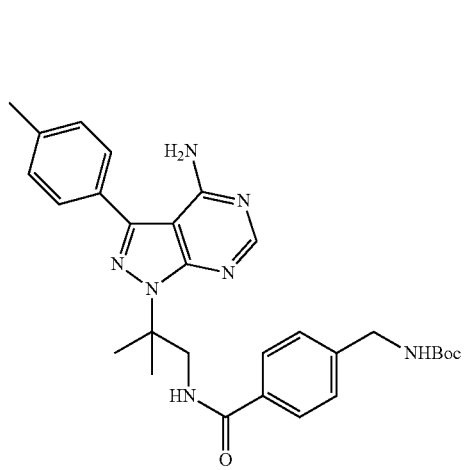 [SMILES: Cc1ccc(-c2nn(C(C)(C)CNC(=O)c3ccc(CNC(=O)OC(C)(C)C)cc3)c3ncnc(N)c23)cc1]
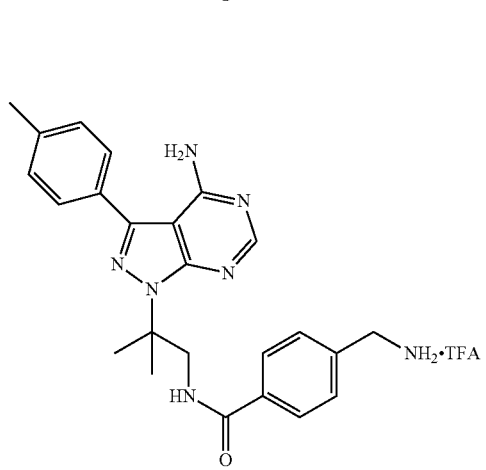
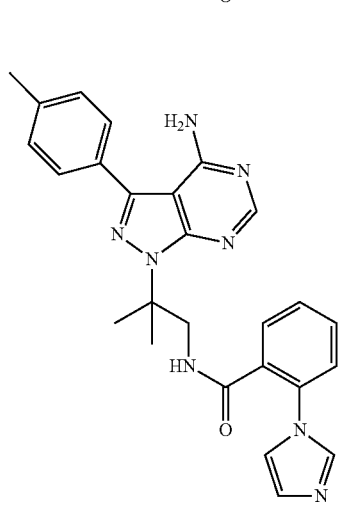

17
-continued
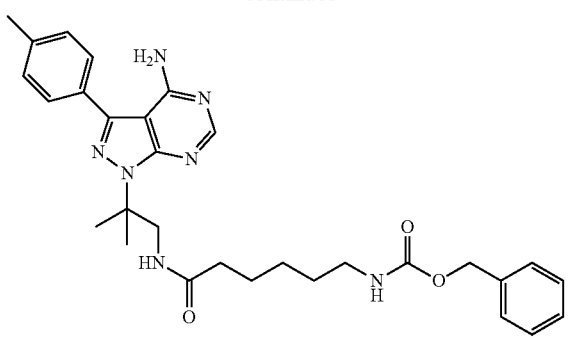
18
-continued
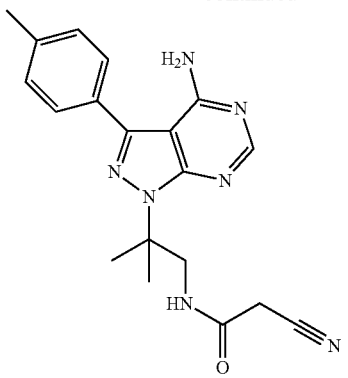
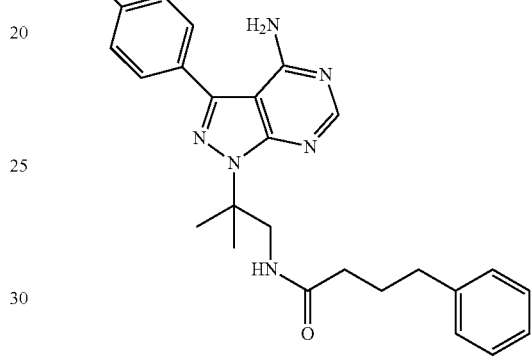
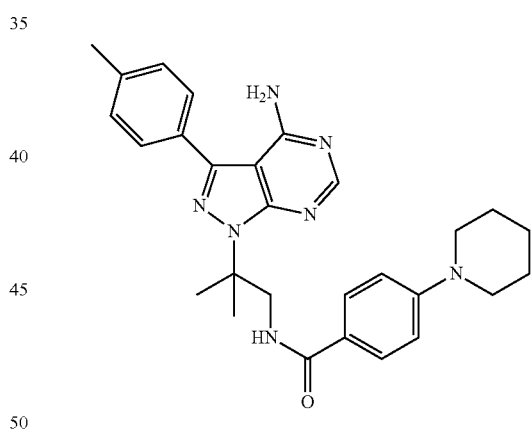
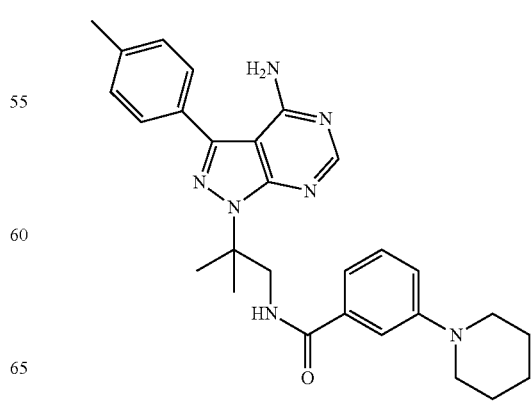

-continued
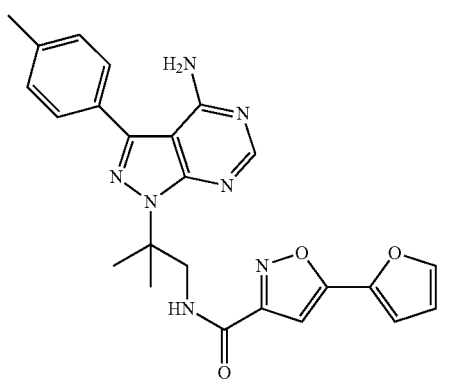
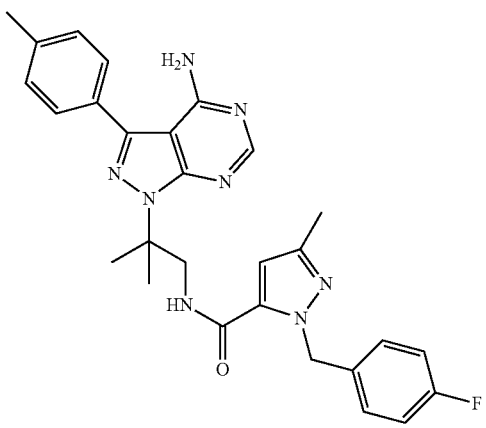
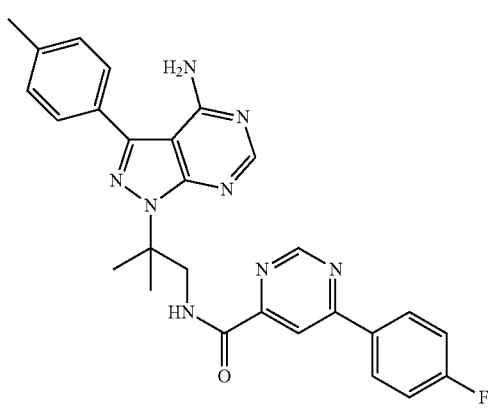
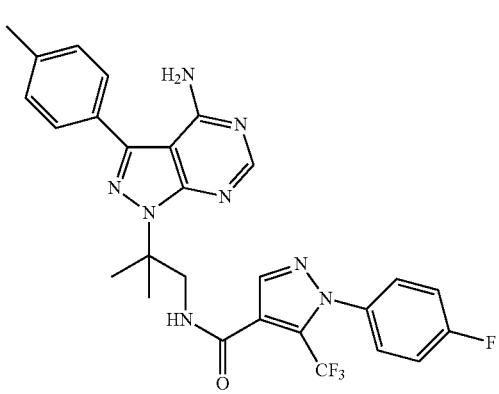
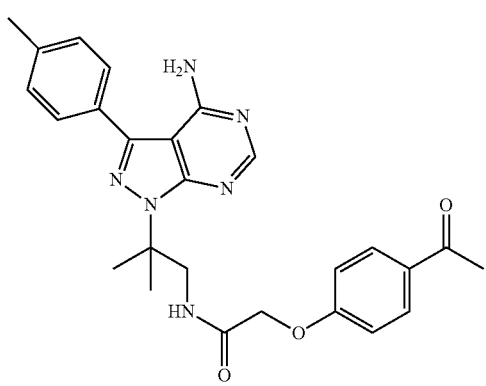
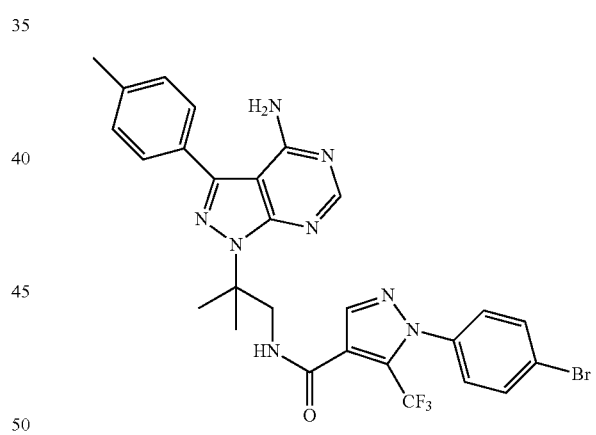
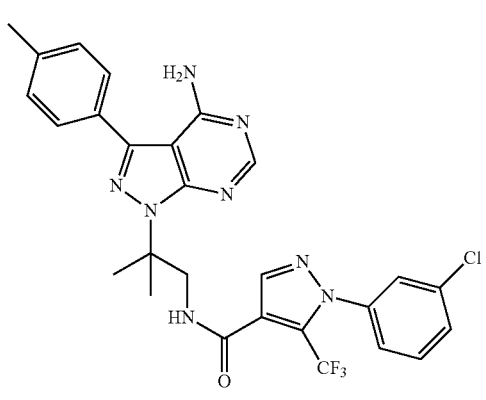
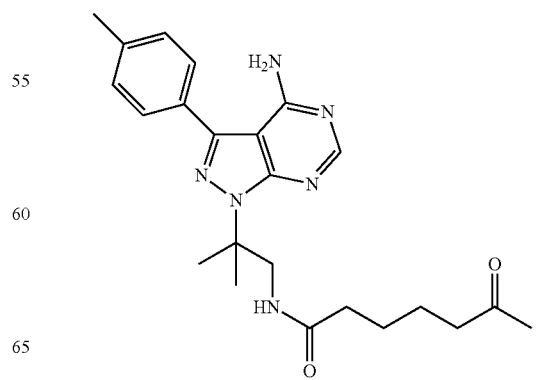

21
-continued
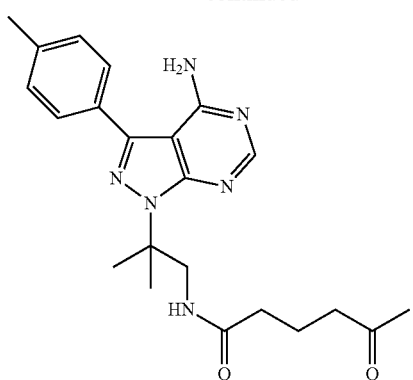
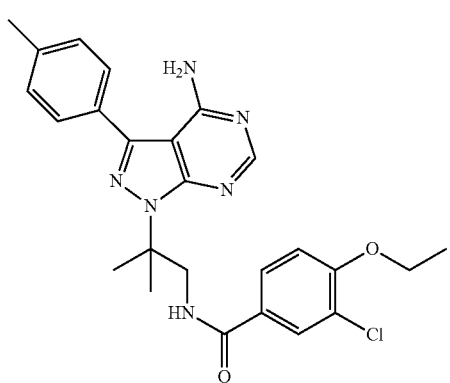
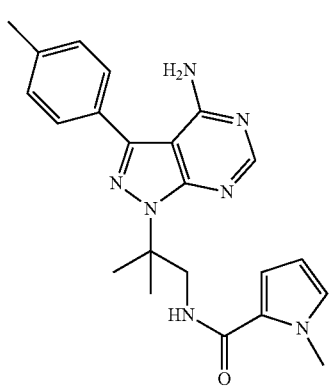
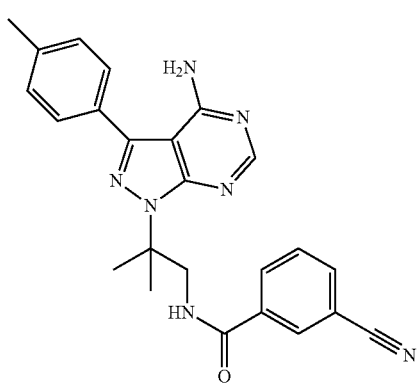
22
-continued
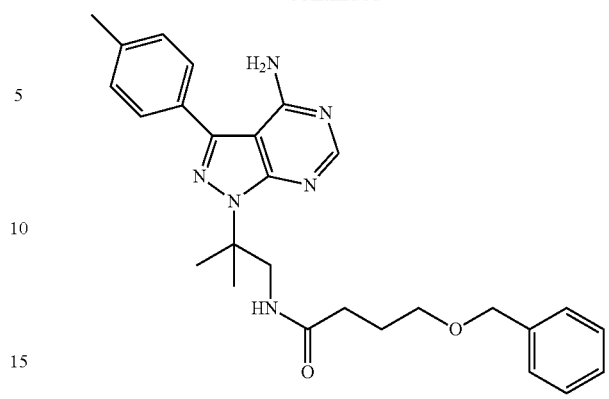
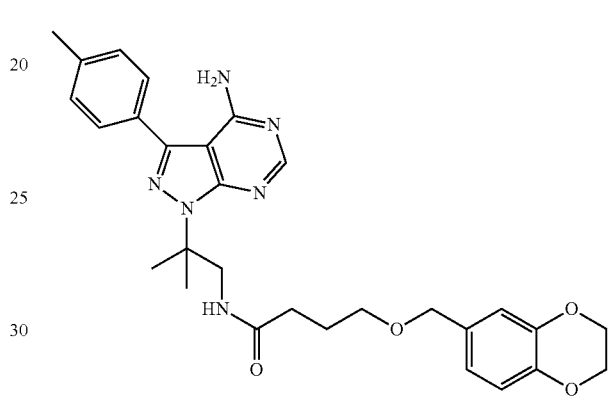
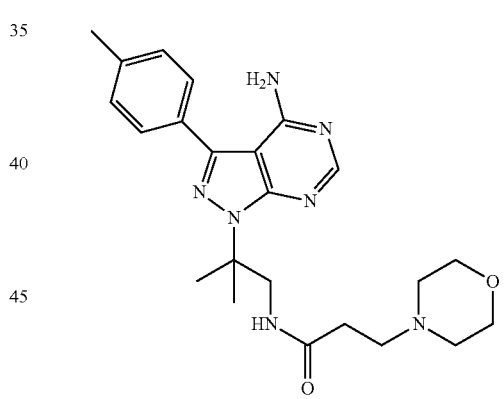
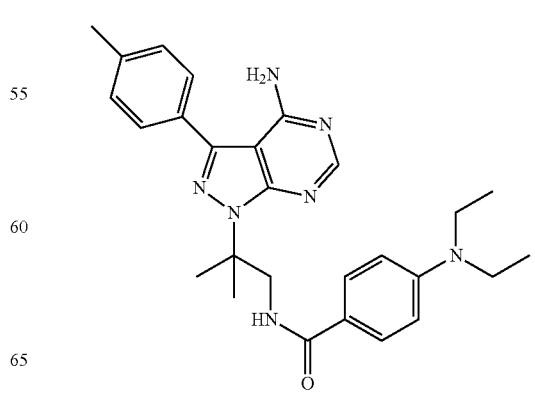

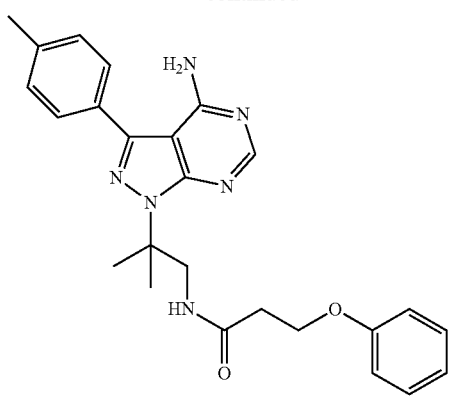
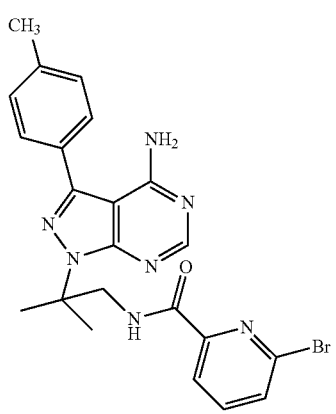
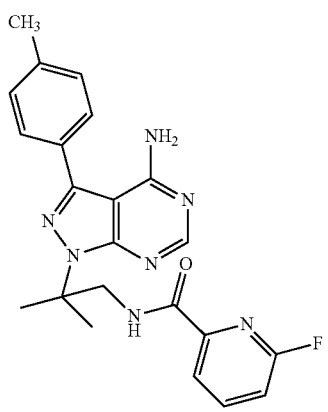
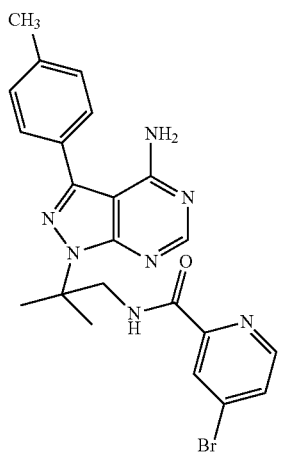
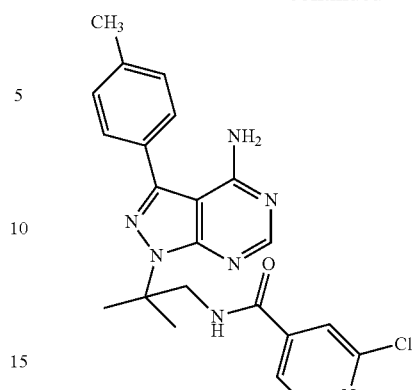
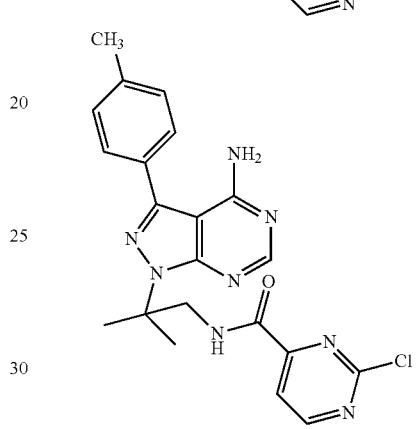
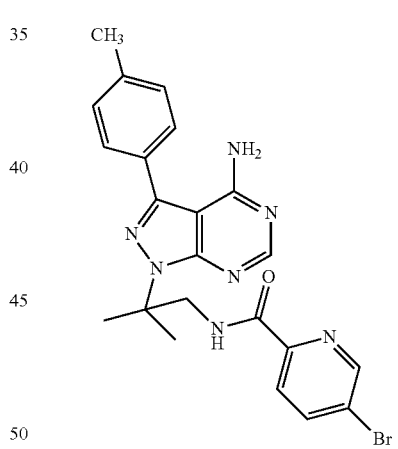
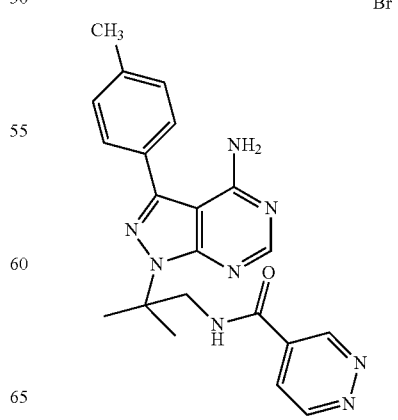

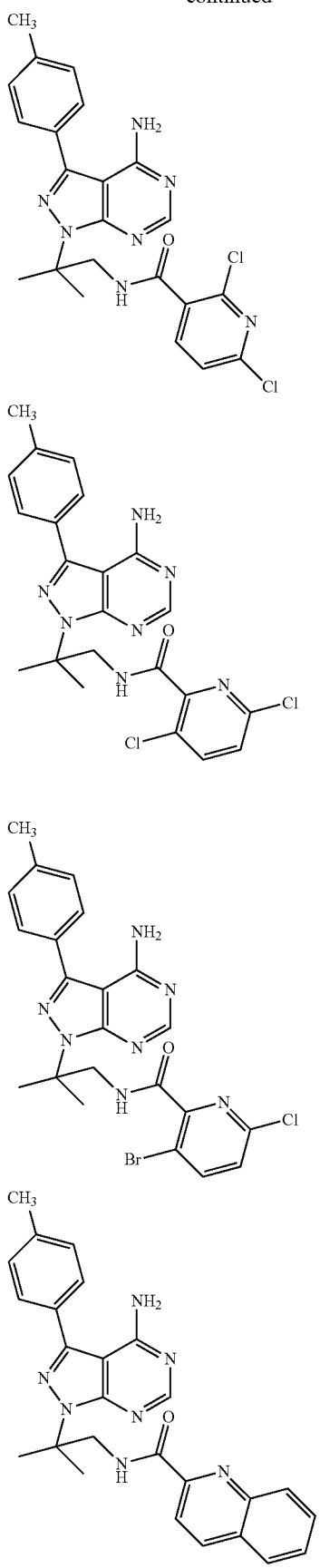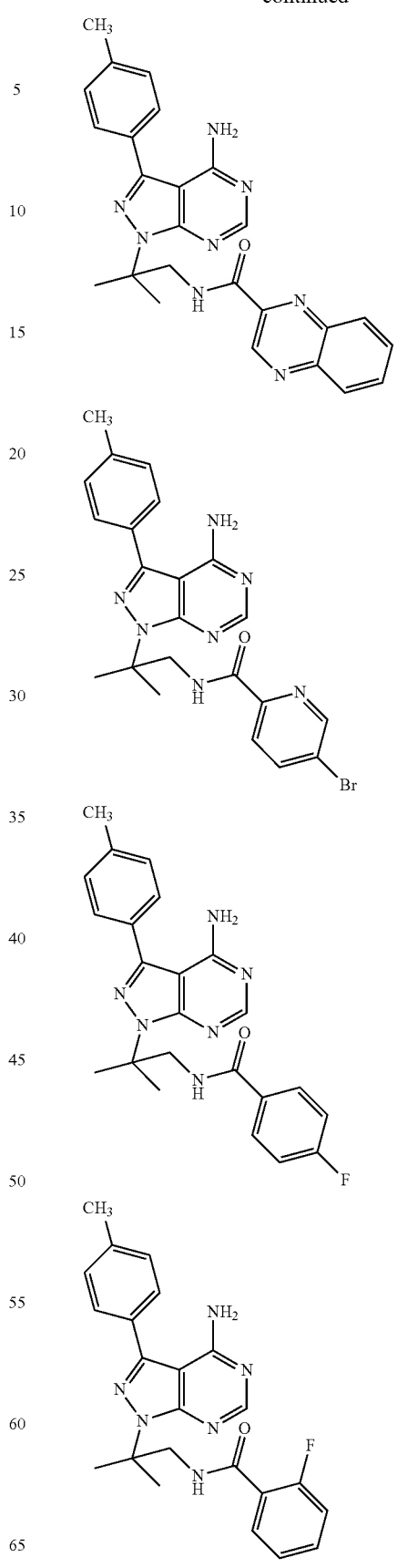

27
-continued
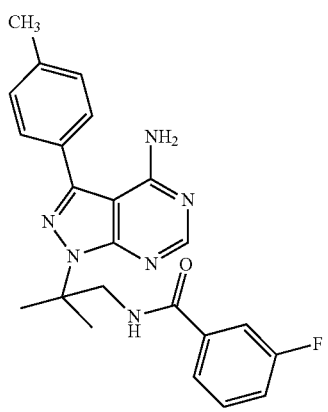
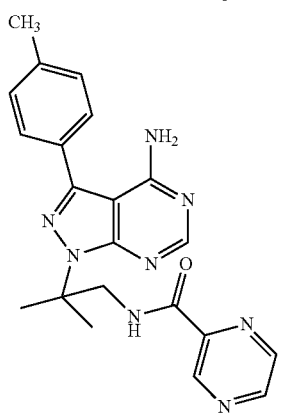
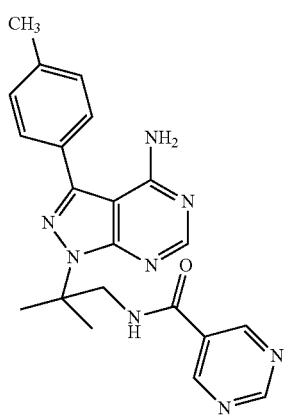
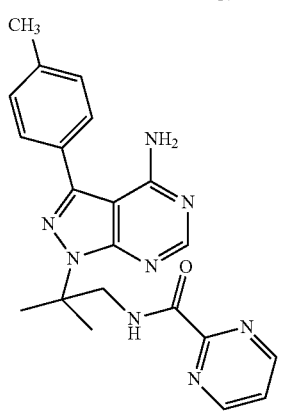
28
-continued
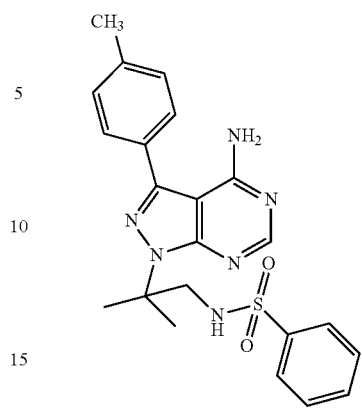
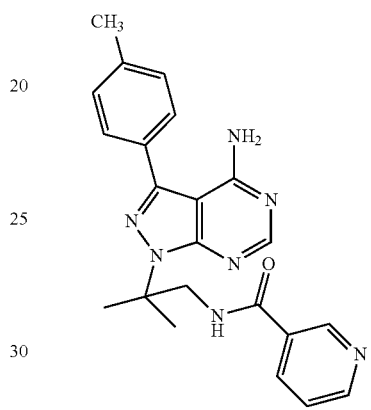
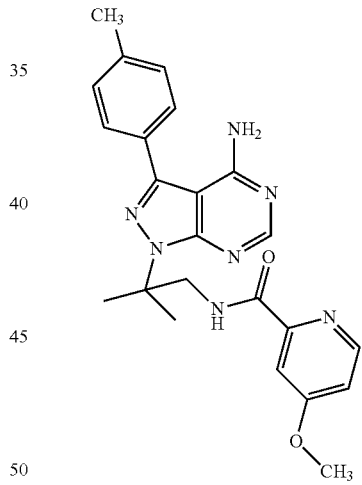
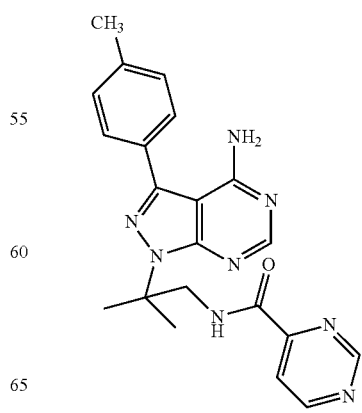

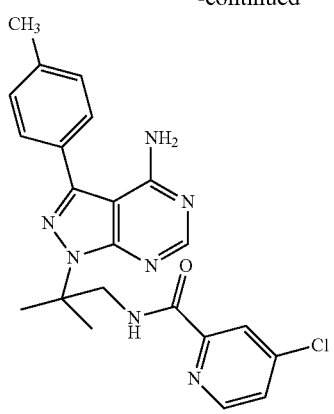
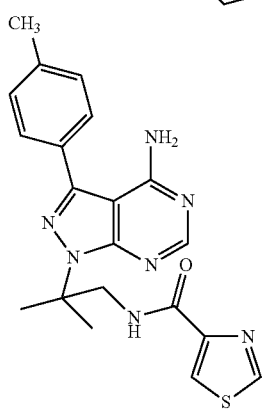
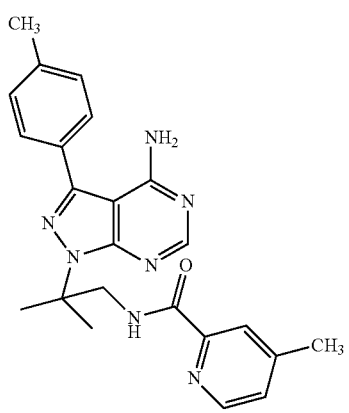
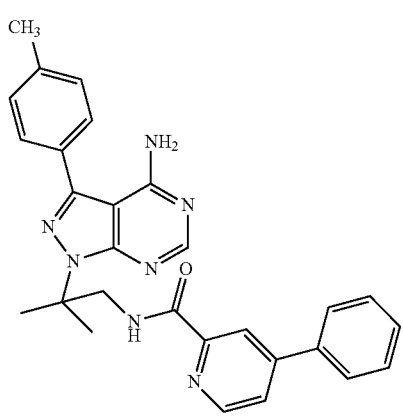
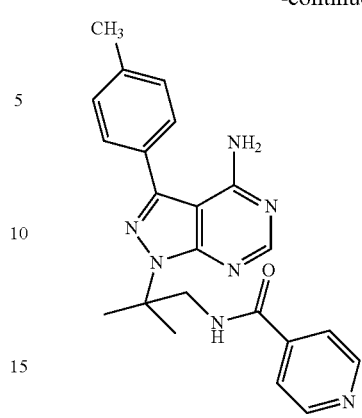
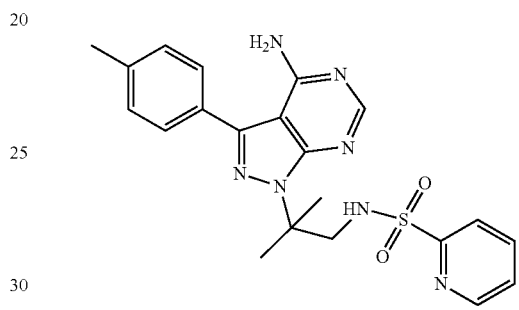
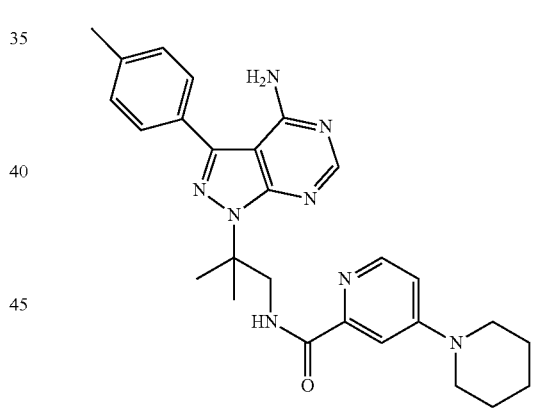
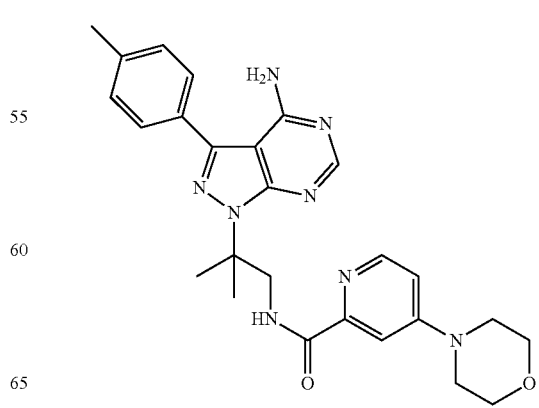

31
-continued
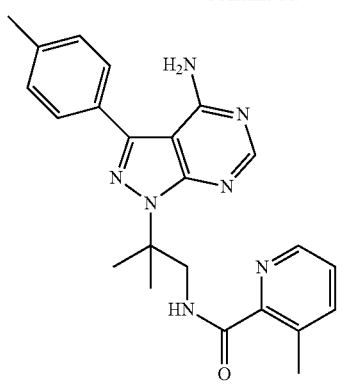
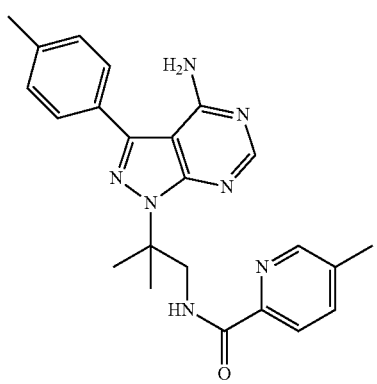
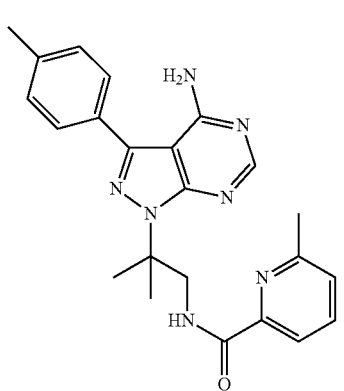
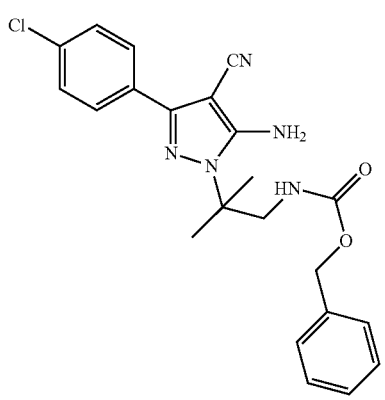
32
-continued
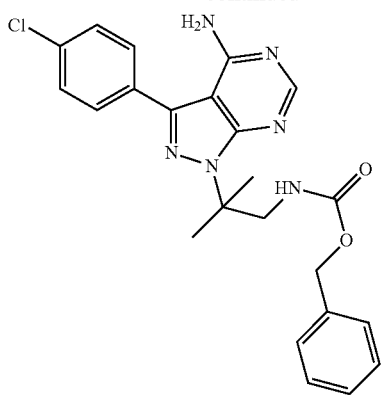
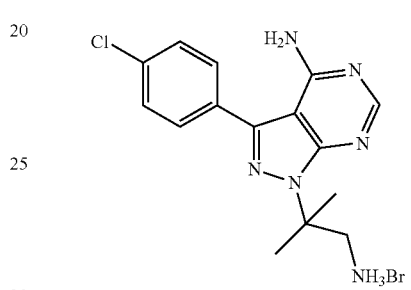
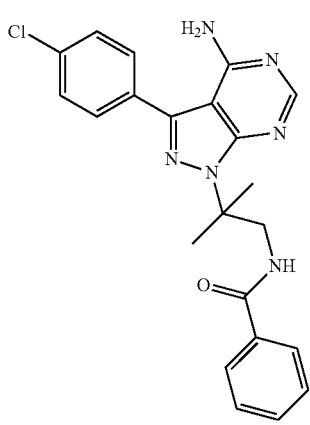
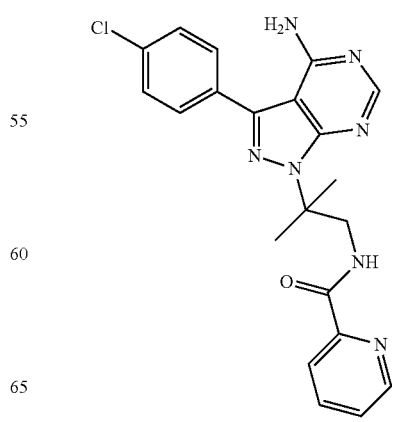

33
-continued
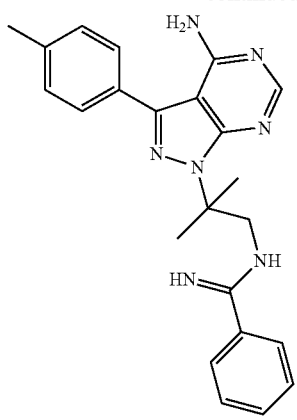
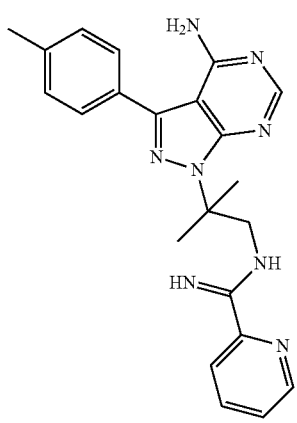
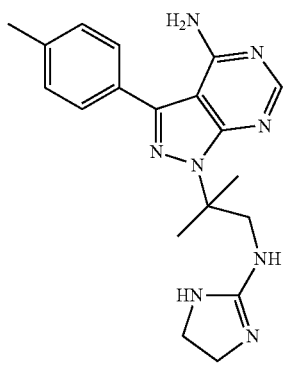
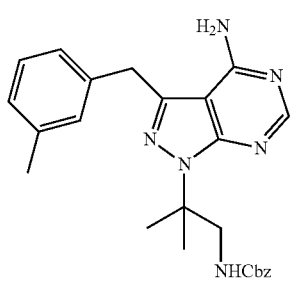
34
-continued
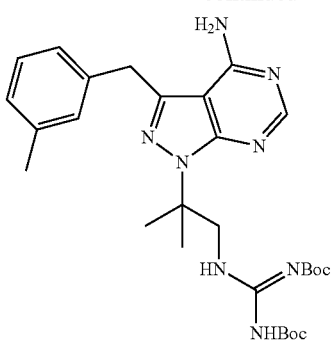
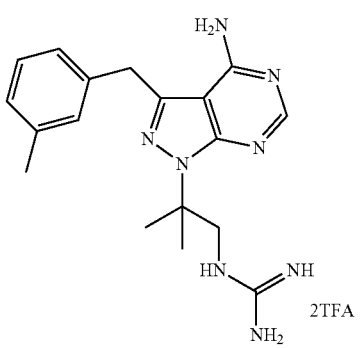
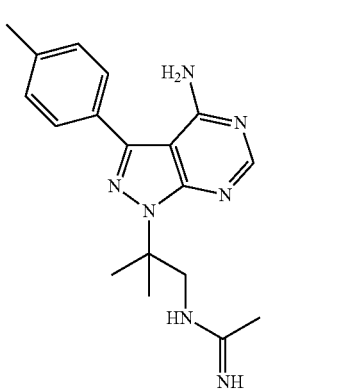
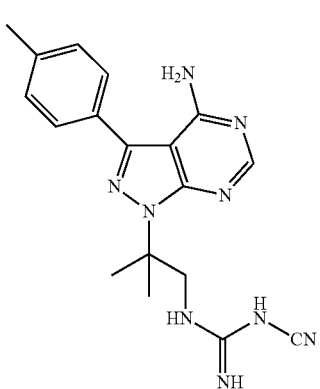

35
-continued
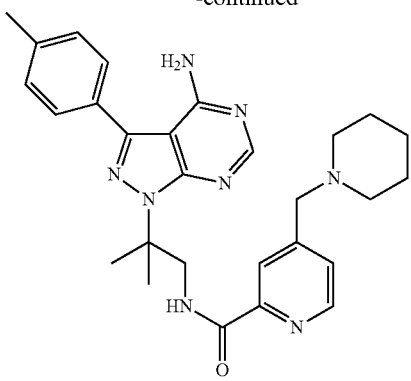
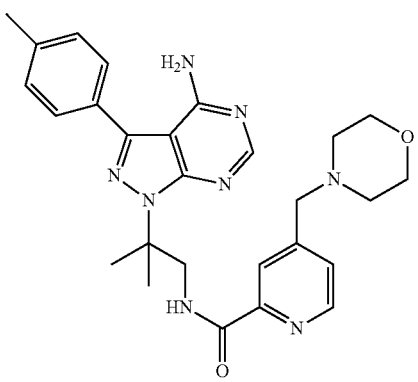
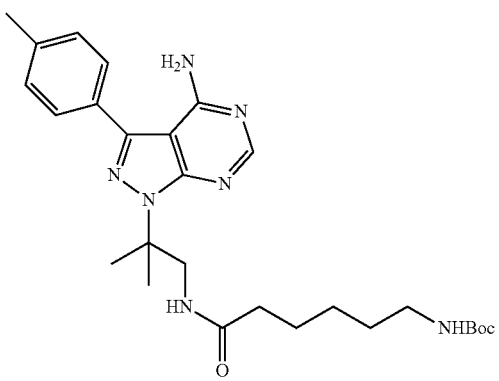
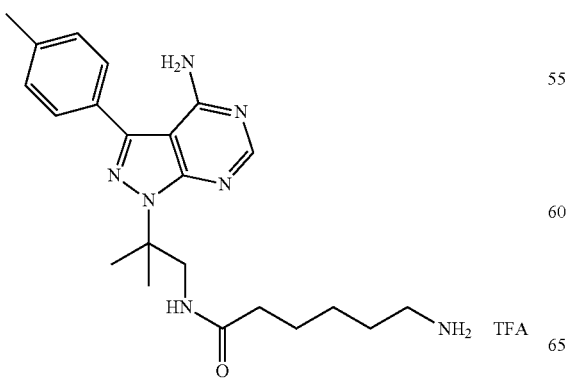
36
-continued
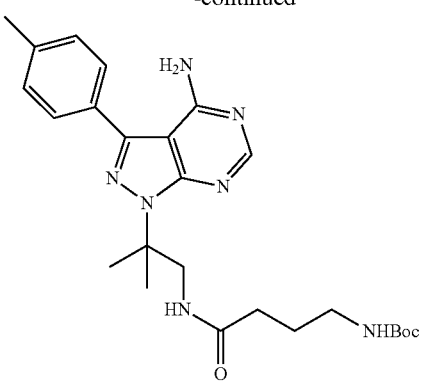
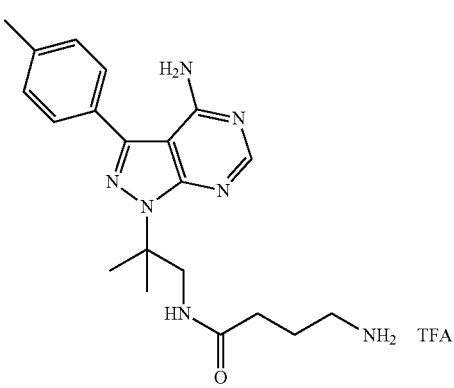
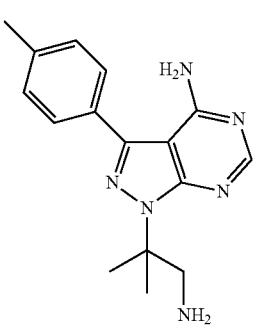
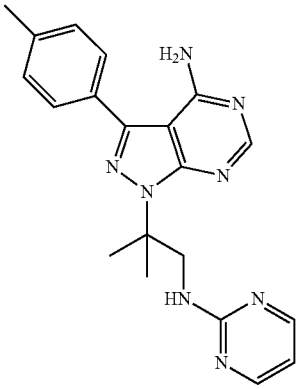

-continued

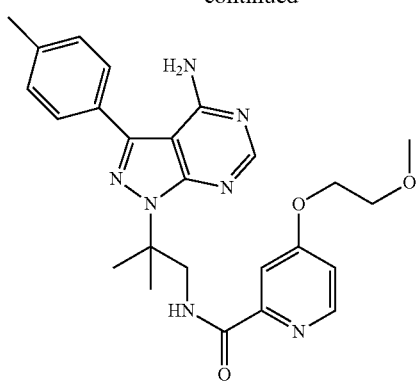

The compounds of the present invention may be prepared by the following general reaction sequence depicted in the Schemes below:

Scheme 1

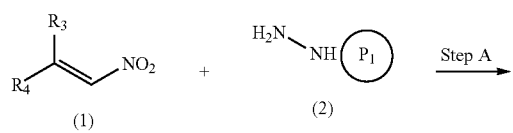

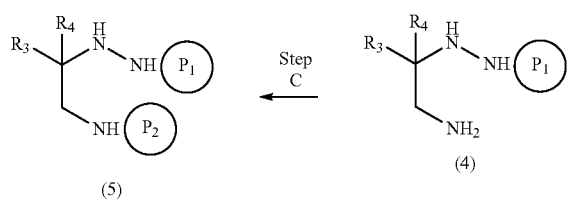

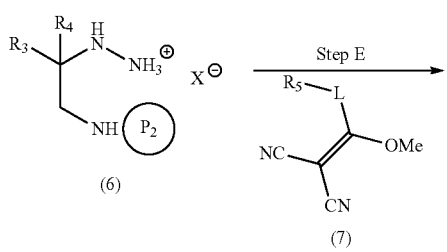

-continued

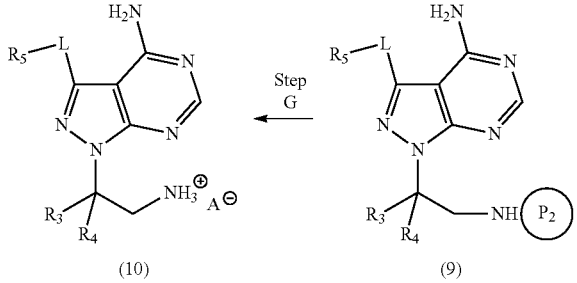

Wherein

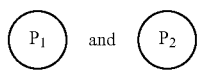

represent nitrogen protecting groups, and variables $R_3$-$R_5$ and L are as defined above.

Preferred conditions for the steps outlined in Scheme 1 include:

Step A: Addition of the 2,2-disubstituted nitroethene (1) to protected carbazate (2) may be facilitated by mixing the starting materials (in preferably equimolar amounts) in an aqueous solvent system. Preferably the solvent system is 1:1 water/acetonitrile. Preferably the reaction is conducted at room temperature. The reaction progress can be monitored by layer chromatography (TLC) [e.g., CH$_2$Cl$_2$/MeOH 90:10].

Step B: The reduction of (3) to primary amine (4) may be facilitated by any suitable reducing agent known in the art such as FeCl$_3$, and sodium dithionite. The reduction may also be facilitated by hydrogenation using pallasium (Pd) or Raney nickel as catalysts. More preferably the reduction process is catalysed by 10% Pd/C in the presence of ammonium formate in a polar protic solvent such as methanol. This reaction is preferably conducted at room temperature and the reaction progress may be monitored by TLC (e.g., CH$_2$Cl$_2$/MeOH 95:5). The crude reaction product may be separated from the catalyst by filtration and used in the next step without any further purification.

Step C: Involves the protection of the primary amine group. Suitable nitrogen protecting groups for

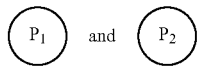

are known to those skilled in the art of organic synthesis and include acyl groups (e.g., acetyl, trifluoroacetyl, and benzoyl), acyloxy groups (e.g., benzylester), aryl (e.g., phenyl), alkylaryl (e.g., benzyl), etc. Other nitrogen protecting groups may be found in *Protective Groups in Organic Synthesis*, T. W. Greene and P. Wutz, John Wiley & Son, 3$^{rd}$ edition. In a preferred embodiment the protecting group

is t-butyloxy carbonyl (BOC). In a preferred embodiment the protecting group

is the N-benzyloxy carbonyl group (Cbz). Protection may be facilitated by reacting the amine (4) in acetonitrile with triethylamine and N-(Benzyloxycarbonyloxy)succinimide.

Step D: Involves the deprotection of the

group of (5) to prepare the salt (6).

Step E: In a preferred embodiment, the reaction product (6) from step D is not purified but instead directly reacted (in situ) with 2-(methoxy-optionally substituted aryl-methylene)-malonitrile (7) to afford the substituted pyrazole (8). This cyclisation step may be facilitated with the use of a suitable non-nucleophilic base (such as Hünigs base, or TEA). The reaction is preferably conducted at elevated temperatures (e.g., between 50°-70° C.).

Step F: The subsequent ring forming step to prepare the pyrazole-[3,4,d]-pyrimidine (9) may be facilitated by reacting (8) with formamide or formamidine acetate (in mol excess) (HN=CHNH$_2$.CH$_3$COOH) at elevated temperatures (e.g., between 110°-160° C.). To drive the reaction to completion further amounts of formamidine acetate may be required over the course of the reaction.

Step G: Involves a deprotection step which may be facilitated by a suitable deprotection agent known in the art. Such agents include those discussed in *Protective Groups in Organic Synthesis*, T. W. Greene and P. Wutz, John Wiley & Son, 3$^{rd}$ edition. Usually such deprotection agents include inorganic and organic acids and accordingly A$^{\ominus}$ represents an anion which has been exchanged during the deprotection step using the inorganic or organic acid. Accordingly, depending on the deprotection agents employed in the process, both X$^{\ominus}$ and A$^{\ominus}$ may be the same or different. Preferably, X$^{\ominus}$ and A$^{\ominus}$ are different. In relation to the embodiments where

is a Cbz group, the deprotection agent may be a HBr solution. In this instance, A$^{\ominus}$ would be represented as Br$^{\ominus}$ (bromide).

Accordingly, it would be appreciated by those skilled in the art that the compounds of formula (8), (9) and (10) represent key intermediates in the production of the compounds of the present invention as these intermediates are endowed with the

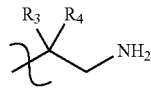

group (or a salt or protected form thereof) which provides greater accessibility and convergency to the compounds of formula (I) in relation to variations in R$_2$ or more particularly R$_1$.

Accordingly, in a further aspect the invention provides a process for preparing a compound of formula (8):

(8)

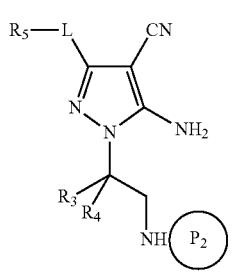

said process comprising the steps of:

a) reacting a compound of formula (I)

(1)

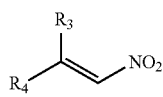

with a compound of formula (2), (2)

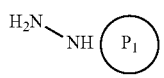

in a suitable polar solvent for a time and under conditions sufficient to obtain (3)

(3)

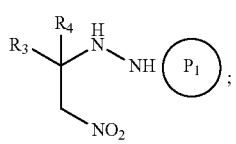

and b) reducing (3) to obtain (4)

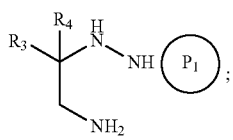
(4)

and c) protecting the primary amine of (4) to obtain (5)

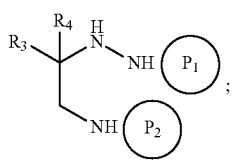
(5)

and d) treating (5) with a deprotection agent to obtain (6)

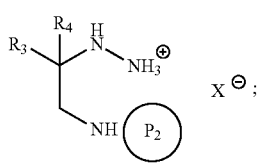
(6)

and e) reacting (6) with (7)

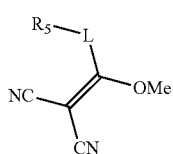
(7)

in the presence of a non-nucleophile base in a polar solvent for a time and under conditions sufficient to obtain (8).

In a further aspect the invention also provides a process for preparing a compound of formula (9):

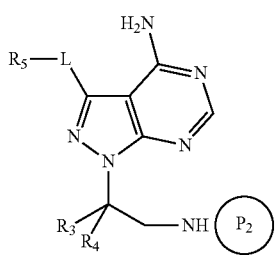
(9)

said process comprising the step of:

a) reacting a compound of formula (8)

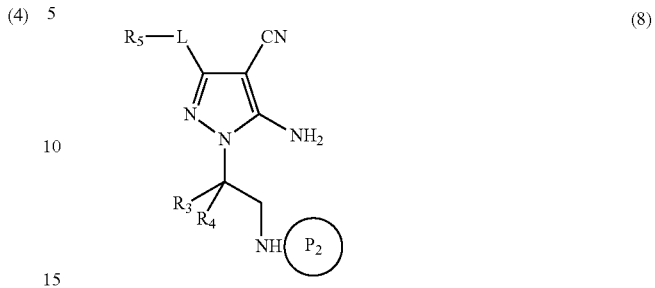
(8)

with formamide or formamidine acetate in a suitable polar solvent for a time and under conditions sufficient to obtain (9).

In an embodiment the reaction is conducted at elevated temperatures, preferably between 130°-160° C.

In a further embodiment the reaction is conducted at elevated temperatures, using methoxyethanol as solvent.

In a further aspect the invention also provides a process for preparing a compound of formula (10)

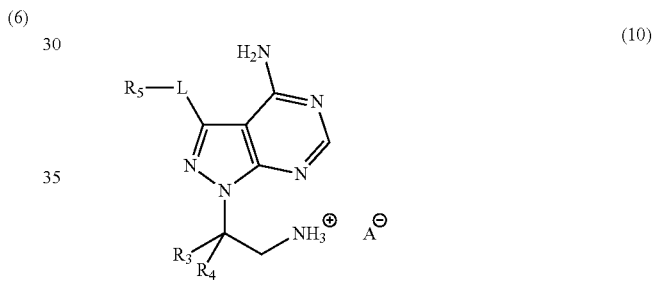
(10)

said process comprising the step of:

a) deprotecting a compound of formula (9)

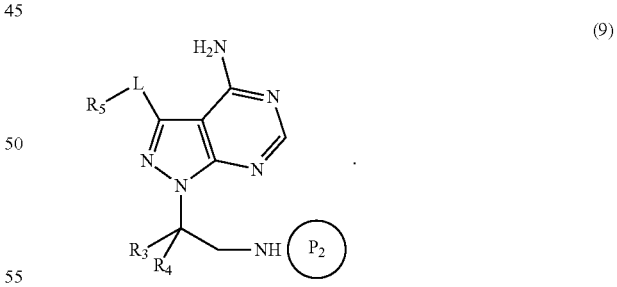
(9)

In an embodiment the deprotection step involves treating a compound of formula (10) with an acid, and preferably an inorganic acid selected from HBr or HCl, more preferably an aqueous solution of HBr.

With (10) in hand the compounds of formula (I) with variable $R_1$ and $R_2$ groups may be prepared, for instance, using conventional nucleophilic chemistry by initially treating the salt (9) with a suitable non-nucleophilic base (e.g., Hünigs base or TEA) and then reacting with a desired electrophilic group (e.g, a substituted anhydride).

In still a further aspect the invention also provides a process for preparing a compound of formula (I):

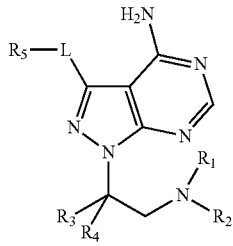
(I)

said process comprising the step of:
a) reacting a compound of formula (10)

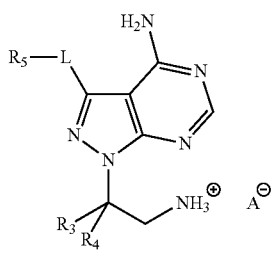
(10)

or the free base thereof,
with a suitable substrate for a time and under conditions sufficient to form a compound of formula (I).

Other methods for preparing the compounds may include the following process steps:

Scheme 2

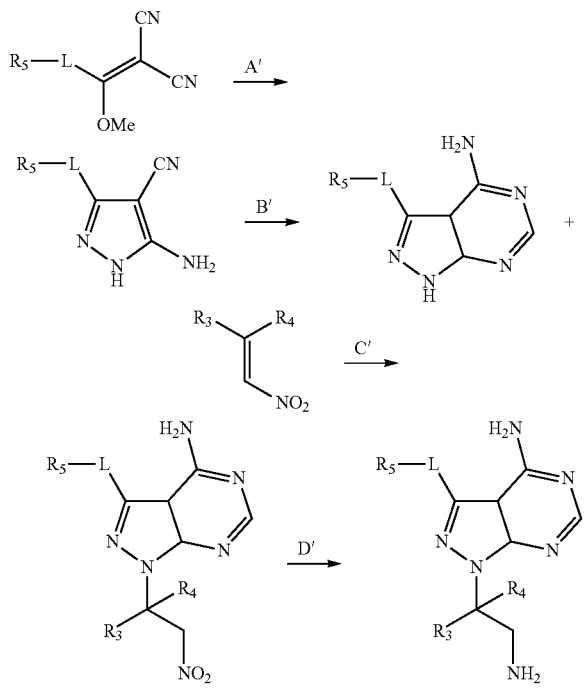

Step A': Uses hydrazine or salt thereof maybe in presence of base in EtOH at reflux Step B': Starting material heated at, for instance, 180° C. in formamide or reacted with formamidine acetate in ethoxy-ethanol at 120° C. Other classical methods of pyrrazolopyrimidine synthesis can be used.

Step C': Starting material and substituted nitroalkene stirred in, for instance, DMF at 95° C. for 48 hrs.

Step D': Aliphatic nitro reduction methods apply here. Used for this work: Zn, 6M HCl, EtOH or Pd(OH)$_2$ in MeOH under hydrogen.

Scheme 3

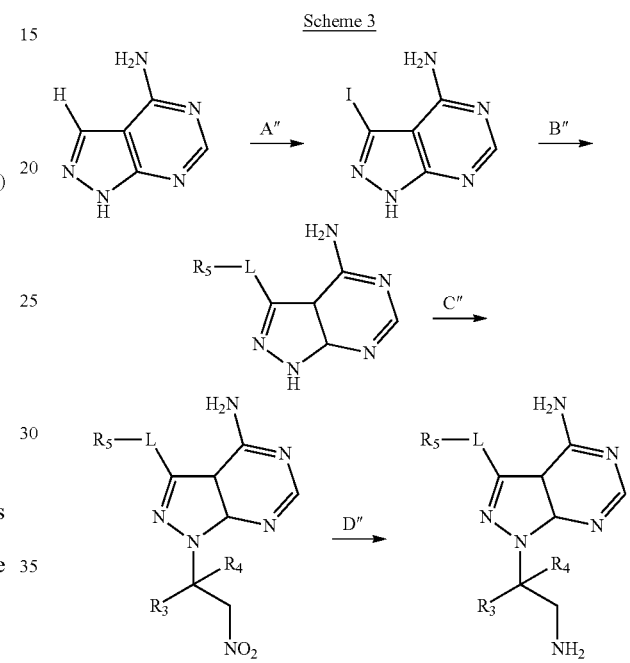

Step A": Usual iodination methods. Methods used: N-iodosuccinimide in DMF at 80° C.

Step B": Metal mediated coupling reactions such as Suzuki or Negishi coupling reactions can be applied here. For example, boronic acid and Pd(Ph$_3$)$_4$ in dioxane at 180° C. in microwave reactor for 10 minutes; or aryl- or alkyl-potassium trifluoroborate salts with palladium catalysts.

Step C" and D": As with step C' and D' above.

Another variation is to add, remove or modify the substituents of the product to form new derivatives which fall within the scope of the compounds of the present invention. This could be achieved again by using standard techniques for functional group inter-conversion, well known in the industry such as those described in Comprehensive Organic Transformations: a guide to functional group preparations by Larock R C, New York, VCH Publishers, Inc. 1989.

Examples of possible functional group inter-conversions are: —C(O)NRR' from —CO$_2$CH$_3$ by heating with or without catalytic metal cyanide, e.g. NaCN, and HNRR' in CH$_3$OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR'" with H$_3$NR$^+$OAc$^-$ by heating in alcohol; —C(NR'R")SR from —C(S)NR'R" with R—I in an inert solvent, e.g. acetone; —C(S)NR'R" (where R' or R" is not hydrogen) from —C(S)NH$_2$ with HNR'R"; —C(=NCN)—NR'R" from —C(=NR'R")—SR with NH$_2$CN by heating in anhydrous alcohol, alternatively from —C(=NH)—NR'R" by treatment with BrCN and NaOEt in EtOH; —NR—C(=NCN)SR from —NHR' by treatment with (RS)$_2$C=NCN; —NR"SO$_2$R from —NHR' by treatment with ClSO$_2$R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR' with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R' from RC(O)R' by R"CO$_3$H; —CCH$_2$OH from —C(O)OR' with Na/R'OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH; —S(O)$_2$R from —SR with mCPBA.

As mentioned previously, the preferred compounds of the invention are inhibitors of tyrosine kinase and in particular Src kinase and therefore can be useful in methods of therapy. The compounds of the present invention have also been observed to target serine/threonin protein kinases, and in particular RIPK2 and MEK5. As such these compounds may be used for treating tumours. As used herein the term "tumour" is used broadly to define any malignant cancerous growth, and may include leukemias, melanomas, colon, lung, ovarian, skin, breast, prostate, CNS, and renal cancers, as well as other cancers.

The compounds of the invention having Src kinase inhibitory activity may also be used in the treatment of tumours, and in particular colon cancer.

The invention also provides for the use of a compound of formula (I), (Ia), (Ib), (Ic), (Id), (Ie) or (If) in the manufacture of a medicament for treating tumours, and in particular colon cancer.

There is also provided a method of treatment of tumours (in particular colon cancer) comprising the administration of an effective amount of a compound of formula (I), (Ia), (Ib), (Ic), (Id), (Ie) or (If) to a subject in need thereof.

In another embodiment the tumour is breast cancer.

However, it will be understood that the compounds of the invention can be used in treating diseases or conditions characterised by cell proliferation (including cell hyperproliferation) which is initiated and/or progressed by aberrant TPK activity and more particularly serine/threonine protein kinase and/or Src kinase activity. In particular, the present compounds can also be used in treating psoriasis, immunoregulation (graft rejection), atherosclerosis, rheumatoid arthritis, acute and chronic inflammatory conditions, Crohn's disease and the like.

Known related pyrazolopyrimidines PP1 and PP2 (as disclosed in U.S. Pat. No. 5,593,997)

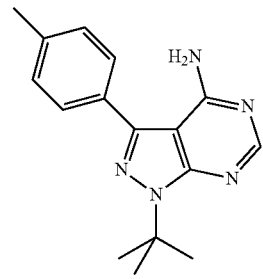

PP1

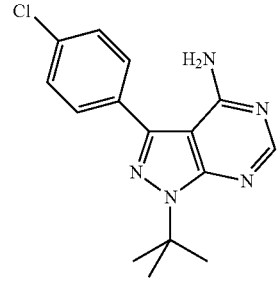

PP2 have been reported as potent inhibitors of SFKs, althought they do not discriminate between members of this kinase family. They also inhibit other tyrosine kinases such as EGF-R.

While such activity would appear to be therapeutically useful, PP1 and PP2 are poorly soluble and accordingly these compounds are not viewed as being "drug like". It has been surprisingly found that the compounds of the present invention have improved solubility and drug-like profiles (especially under acidic conditions) while at the same time retain potent inhibitory activity.

Compounds of the invention which possess bioactivity, such as Src kinase inhibitory activity, can be formulated as a composition, particularly a pharmaceutical composition, together with a pharmaceutically acceptable additive.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated (e.g., colon cancer).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages may lie within the range of about 0.1 ng per kg of body weight to 1 g per kg of body weight per dosage. A typical dosage is in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well blown in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan guni, bentonite, alginic acid or agar. Suitable flavouring agents include peppermint oil, oil of wintergreen, cherry, orange or raspberry flavouring. Suitable coating agents include polymers or copolymers of acrylic acid and/or niethacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The novel bioactive compounds of the invention can be administered to a subject as a pharmaceutically acceptable salt thereof. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quartemised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I), (Ia), (Ib), (Ic), (Id), (Ie) or (If) is also within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate or phosphate ester, or where a free amino group is converted into an amide (eg α-aminoacid amide). Procedures for esterifying, eg. acylating, the compounds of the invention are well known in the art and may include treatment of the compound with an appropriate carboxylic acid, anhydride or chloride in the presence of a suitable catalyst or base.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The mode of proliferative diseases, such as tumors, is multi-factorial. In the treatment of such diseases drugs with different mechanisms may be combined (ie combination therapies). The compounds of the invention may be particularly useful in combination therapy, eg. combining the treatment with other chemotherapeutic or radiation treatments.

For instance in order to potentiate anti-tumour treatments using the compounds of the present invention one or more other cytotoxic compounds including 5-FU, oxaliplatin, paclitaxel, gemcitabine, docetaxel, cisplatin, and doxorubicin may also be administered. The combination therapy may also include the addition of other Src kinase inhibitors such as AZD-0530 (Saracatinib), Dasatinib (BMS-354825 or Sprycel) and Bosutinib (SKI0606) or inhibitors of ERK5, MEK5, RIPK5, and FAK (PTK2) such as AZD6244, U0126, SB202190, and PF-562271.

The combination partners in such therapies may be administered together, one after the other, separately in one combined unit dosage or in separate unit dosage forms.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLE

Synthetic Examples

Example 1

Preparation of N'-(1,1-Dimethyl-2-nitro-ethyl)-hydrazinecarboxylic acid tert-butyl ester

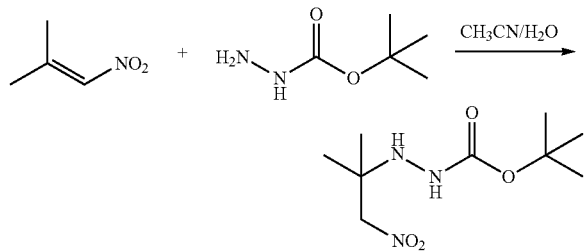

1A: tert-Butyl carbazate (2.61 g, 19.8 mmol) was added to mixture of 2,2-dimethyl-nitroethylene (2 g, 19.8 mmol) in 20 mL of 1:1 water/acetonitrile. After one hour, TLC (CH$_2$Cl$_2$/MeOH 90:10) indicated complete reaction. The reaction was diluted with water. The aqueous phase was washed three times with EtOAc. The combined organic phases were rinsed with water and brine, dried over Na$_2$SO$_4$ and concentrated. The solid residue was purified on SiO$_2$ using CH$_2$Cl$_2$/MeOH 95:5 to 90:10. A white solid was obtained (m=3.6 g, 78%). $^1$H NMR (ppm, CDCl$_3$): δ 1.26 (s, 6H), 1.49 (s, 9H), 4.43 (s, 2H), 6.12 (br s, 1H). $^{13}$C NMR (ppm, CDCl$_3$): δ 23.24, 28.23, 57.91, 81.35, 82.06, 158.20. LCMS (+esi): 256 (M+Na$^+$).

1B: Preparation of N'-(2-Benzyloxycarbonylamino-1,1-dimethyl-ethyl)hydrazinecarboxylic acid tert-butyl ester

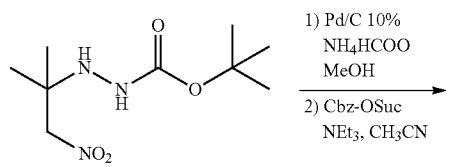

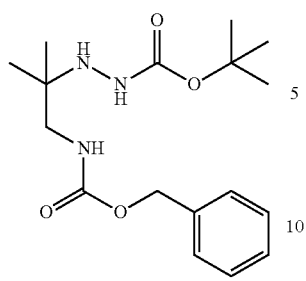

Pd/C (10%, 240 mg) was added to a mixture of compound 1A (1 g, 4 mmol) and ammonium formate (1.16 g, 18.4 mmol) in 8 mL of dry methanol. The reaction was stirred at room temperature for 1 hour (strong gas evolution) after which time TLC ($CH_2Cl_2$/MeOH 95:5) indicated complete consumption of starting material. The reaction was filtered through a pad of celite and the solids were rinsed with methanol. The filtrate was concentrated. The colourless oil was used in the next step without further purification. $^1$H NMR (ppm, $CDCl_3$): δ 1.16 (s, 6H), 1.47 (s, 9H), 2.78 (s, 2H), 3.03 (br s, 2H+$H_2O$), 6.6 (br s, 1H). LCMS (+esi): 204.1 (M+H$^+$).

The amine was dissolved in 8 mL of anhydrous acetonitrile. Triethylamine (0.5 mL, 3.6 mmol) and N-(Benzyloxycarbonyloxy)succinimide (897 mg, 3.6 mmol) were successively added. The reaction was stirred at room temperature for 16 hours and then concentrated. The residue was taken into EtOAc and 10% citric acid. The aqueous layer was extracted three times with EtOAc. The combined organic layers were washed with 10% citric acid, water and brine, dried over $Na_2SO_4$ and concentrated. A colourless oil was obtained that crystallised slowly upon standing. No further purification was required (m=1.2 g, 90% for two steps). $^1$H NMR (ppm, $CDCl_3$): δ 1.01 (s, 6H), 1.43 (s, 9H), 3.04 (d, J=6.57 Hz, 2H), 3.51 (br s, 1H), 5.09 (s, 2H), 6.22 (br s, 1H), 7.28-7.32 (m, 5H). $^{13}$C NMR (ppm, $CDCl_3$): δ 22.91, 28.25, 46.36, 57.73, 66.67, 81.08, 128.00, 128.06, 128.46, 136.76, 157.23, 157.61.

1C: Preparation of [2-(5-Amino-4-cyano-3-phenyl-pyrazol-1-yl)-2-methyl-propyl]-carbamic acid benzyl ester

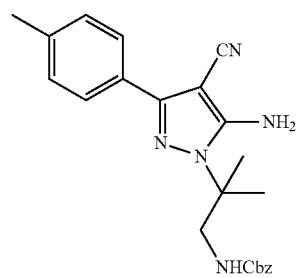

Compound 1B (310 mg, 0.92 mmol) was dissolved in 1 mL of dry acetonitrile. Tosic acid (875 mg, 4.6 mmol) was dissolved in 3 mL of dry acetonitrile. Molecular sieves were added to both solutions and stood for 30 minutes. The solution of tosic acid was then added the other mixture and the reaction was stirred at room temperature for 3 hours. After that time the reaction was filtered and the solid washed with acetonitrile and $CH_2Cl_2$). The filtrate was concentrated to afford a thick colourless oil. It was dissolved in 2 mL of ethanol. Triethylamine (640 μL, 1.48 mmol) and 2-(Methoxy-p-tolyl-methylene)-malononitrile (182 mg, 0.92 mmol) were successively added. The reaction was then heated at 60° C. for 3 hours. After cooling down, the reaction was concentrated. Water and EtOAc were then added and the aqueous phase was extracted three times with EtOAc. The combined organic layers were dried over $Na_2SO_4$ and concentrated. The oily residue obtained was purified by flash chromatography on $SiO_2$ using 100% $CH_2Cl_2$ then $CH_2Cl_2$/MeOH 99:1. A colourless oil that solidifies slowly overnight was obtained (m=270 mg, 73%). NMR (ppm, $CDCl_3$): δ 1.58 (s, 6H), 2.36 (s, 3H), 3.77 (d, J=6.63 Hz, 2H), 4.40 (br s, 2H), 5.08 (s, 2H), 5.59 (br t, J=5.94 Hz, 1H), 7.20 (d, J=8.55 Hz, 2H), 7.31 (m, 5H), 7.74 (d, J=8.13 Hz, 2H). $^{13}$C NMR (ppm, $CDCl_3$): δ 21.35, 24.18, 50.56, 63.17, 66.99, 76.34, 115.22, 126.09, 128.15, 128.22, 128.33, 128.55, 129.42, 136.34, 139.11, 149.13, 151.57, 156.96. LCMS (+esi): 404.3 (M+H$^+$).

1D: Preparation of [2-(4-Amino-3-phenyl-pyrazolo[3,4-d]pyrimidin-1-yl)-2-methyl-propyl]-carbamic acid benzyl ester

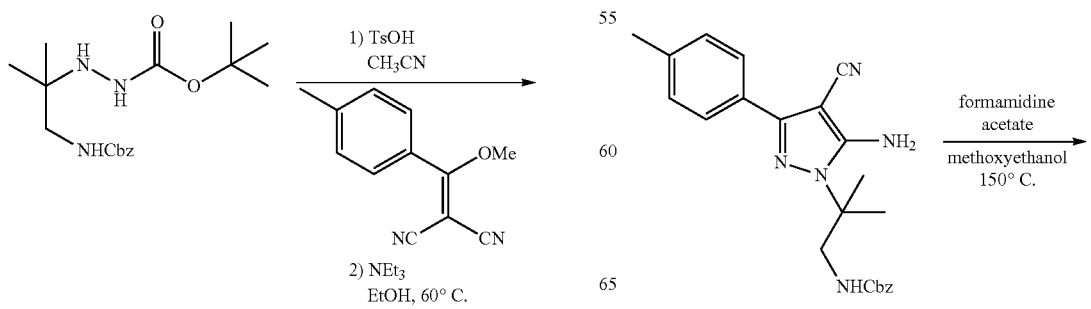

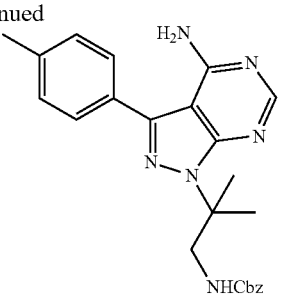

Compound 1C (100 mg, 0.25 mmol) and formamidine acetate (108 mg, 1 mmol) were reacted at 150° C. in 0.4 mL of methoxyethanol. 3 more portions of formamidine acetate were added at one hour interval to reaction mixture. After that time, water and EtOAc were added. The aqueous phase was extracted three times with EtOAc. The combined organic phases were washed two times with water and brine, dried over $Na_2SO_4$ and concentrated. The thick yellowish oil obtained was purified by two successive flash chromatographies: first using $CH_2Cl_2$/MeOH 100:0 to 97:3 then $CH_2Cl_2$/EtOAc 70:30 to 50:50. A colourless oil was obtained which solidified slowly (m=76 mg, 71%). $^1H$ NMR (ppm, $CDCl_3$): δ 1.71 (s, 6H), 2.38 (s, 3H), 3.87 (d, J=6.63 Hz, 2H), 5.02 (s, 2H), 5.82 (br t, J=6.33 Hz, 1H), 5.94 (br s, 2H), 7.23-7.28 (m, 7H), 7.45 (d, J=8.07 Hz, 2H), 8.23 (s, 1H). $^{13}C$ NMR (ppm, $CDCl_3$): δ 21.34, 25.02, 49.82, 64.24, 66.77, 99.18, 128.12, 128.16, 128.35, 128.51, 129.87, 130.15, 136.58, 139.50, 143.79, 152.50, 153.71, 156.83, 156.86. LCMS (+esi): 431.3 (M+H$^+$).

1E: Preparation of 1-(2-Amino-1,1-dimethyl-ethyl)-3-phenyl-1H-pyrazolo[3,4-d]pyrimidin-4-ylamine hydrobromide

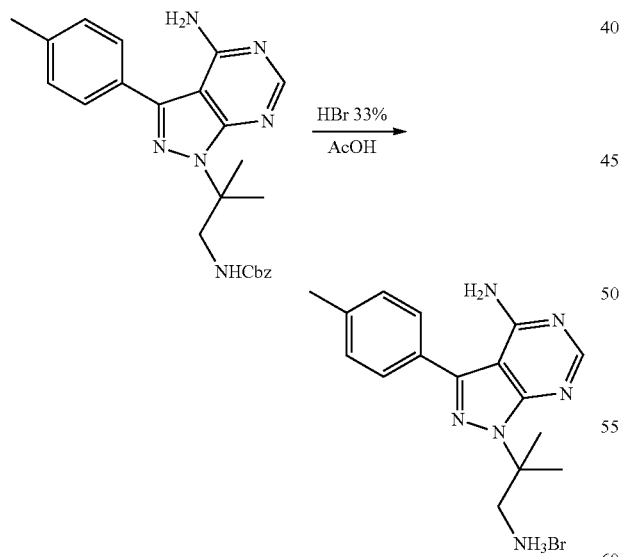

Compound 1D (85 mg, 0.2 mmol) was treated with 1 mL of 33% solution of HBr in glacial acetic acid. The reaction was stirred at room temperature for 1 hour. Dry ether was then added to the mixture leading to the formation of a precipitate. It was collected by filtration, rinsed thoroughly with $Et_2O$ and dried. 50 mg of the compound were redissolved in 50 mL of water and freeze dried for two days. A white solid was obtained. $^1H$ NMR (ppm, DMSO-$d_6$): δ 1.73 (s, 6H), 2.34 (s, 3H), 3.59 (br q, J=5.67 Hz, 2H), 7.33 (d, J=7.89 Hz, 2H), 7.53 (d, J=8.07 Hz, 2H), 7.95 (br s, 3H), 8.40 (s, 1H). $^{13}C$ NMR (ppm, DMSO-$d_6$): δ 20.93, 24.83, 46.51, 61.41, 98.47, 128.33, 128.76, 129.80, 138.82, 144.85, 149.49, 152.83, 154.21. LCMS (+esi): 297 (M-Br$^-$).

Example 2

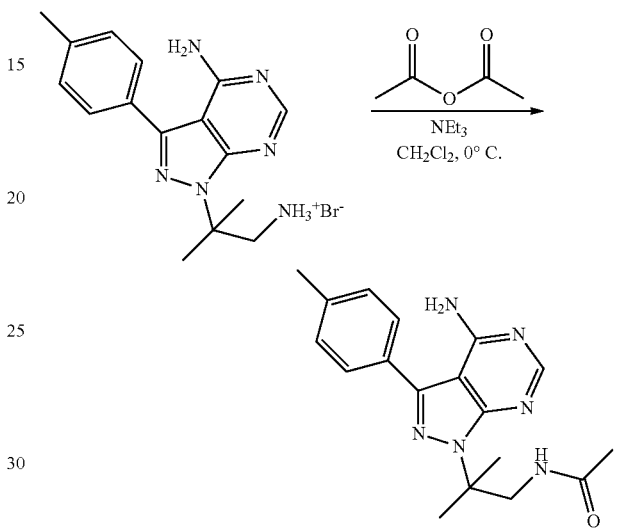

Compound 1E (50 mg, 0.13 mmol) was dissolved in 1 mL of dry $CH_2Cl_2$. The solution was cooled to 0° C. and triethylamine (38 μL, 0.27 mmol) followed by acetic anhydride (13 μL, 0.13 mmol) were added. The reaction was stirred for 1 hour at 0° C. after which time more triethylamine (19 μL, 0.132 mmol) and acetic anhydride (3 μL, 0.03 mmol) were added. The reaction was stirred for a total of 2.5 hours. TLC (90:10 $CH_2Cl_2$/MeOH) indicated complete reaction. The mixture was diluted with $CH_2Cl_2$ and poured onto water. The mixture was extracted three times with $CH_2Cl_2$. The combined organic phases were washed with water end brine and dried over $Na_2SO_4$. Concentration afforded the expected compound, which did not require further purification (m=24.5 mg, 56%). $^1H$ NMR (ppm, $CDCl_3$): δ 1.77 (s, 6H), 1.98 (s, 3H), 2.44 (s, 3H), 3.96 (d, J=6.36 Hz, 2H), 5.74 (br s, 2H), 7.02 (br s, 1H), 7.35 (d, J=7.8 Hz, 2H), 7.55 (d, J=8.07 Hz, 2H), 8.33 (s, 1H). LCMS (+esi): 339.1 (M+H$^+$).

Example 3

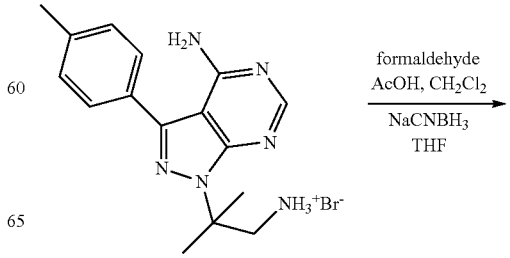

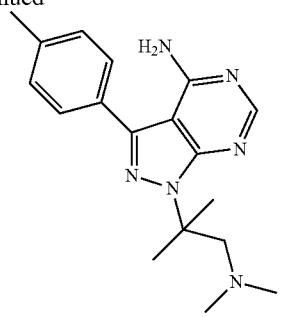

Compound 1E (50 mg, 0.13 mmol) was dissolved in 275 µL of $CH_2Cl_2$. Acetic acid (55 µL), 37% formaldehyde (275 µL) and 550 µL of a 1 M solution of $NaBH_3CN$ in THF were added. The reaction was stirred for 30 minutes. After that time, the reaction was diluted with $CH_2Cl_2$ and water was added. The aqueous phase was extracted three times with $CH_2Cl_2$. The combined organic layers were washed with water and brine and dried over $Na_2SO_4$. The residue was purified by flash chromatography using $CH_2Cl_2$/EtOAc (70:30 to 30:70). A white solid was obtained (m=22 mg, 51%). $^1$H NMR (ppm, DMSO-$d_6$): δ 1.72 (s, 6H), 2.05 (br s, 6H), 2.37 (s, 3H), 2.98 (br s, 2H), 6.7 (br s, 2H), 7.33 (d, J=8.34 Hz, 2H), 7.52 (d, J=8.07 Hz, 2H), 8.21 (s, 1H). LCMS (+esi): 325.2 (M+H$^+$).

Example 4

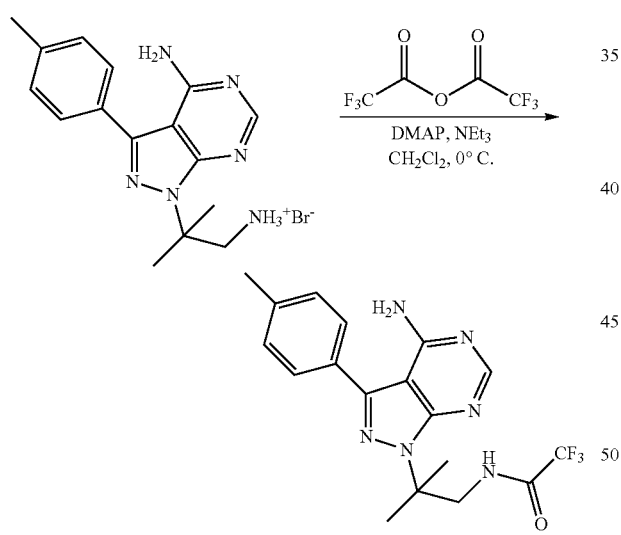

4A: Compound 1E (50 mg, 0.132 mmol) was dissolved in 1.5 mL of dry $CH_2Cl_2$ under nitrogen. DMAP (1.6 mg, 0.0132 mmol) and freshly distilled triethylamine (40 mg, 55.1 µL, 0.398 mmol) were added. The solution was cooled to 0° C. in an ice bath and stirred. In a separate flask, trifluoroacetic anhydride (41.6 mg, 27.5 µL, 0.198 mmol) was dissolved in 1 mL of $CH_2Cl_2$. This solution was added into the first flask and the reaction was stirred overnight. The product was directly purified by flash chromatography on $SiO_2$ using EtOAc/petroleum ether (20:80 to 40:60). The product was obtained as a pale pink solid (m=27 mg, 52%). $^1$H NMR (ppm, CDCl$_3$): δ 1.79 (s, 6H), 2.44 (s, 3H), 3.98 (d, J=6.18 Hz, 2H), 5.74 (br s, 2H), 7.34 (d, J=8.1 Hz, 2H), 7.54 (d, J=8.1 Hz, 2H), 8.33 (s, 1H), 9.27 (br s, 1H). $^{13}$C NMR (ppm, CDCl$_3$): δ 21.3, 25.3, 48.6, 63.2, 116.2, 128.1, 130.2, 139.5, 143.7, 153.9, 154.8, 157.0 (q), 158.1. LCMS (+esi): 393.2 (M+H$^+$).

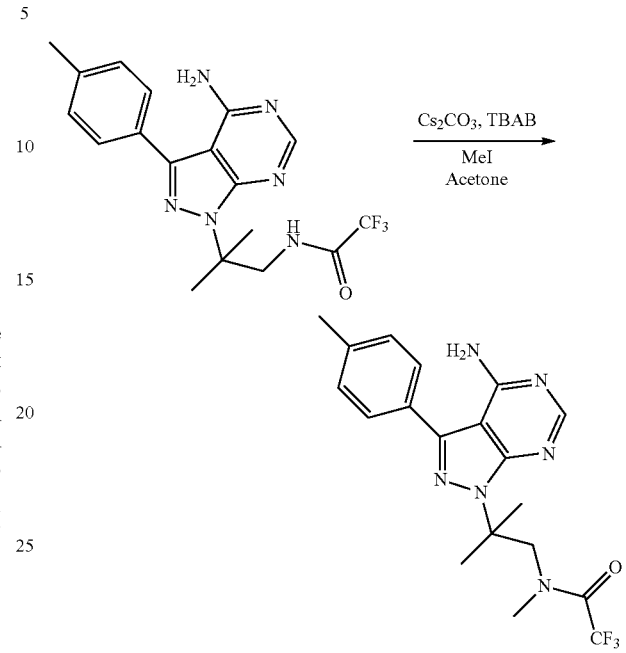

4B: Compound 4A (40 mg, 0.102 mmol), $Cs_2CO_3$ (99.7 mg, 0.31 mmol,) and Tetrabutylammonium bromide (3.3 mg, 0.01 mmol) was dissolved in 1 mL of acetone. MeI (22.3 µL, 0.36 mmol) in solution in acetone was added. The solution was stirred for 48 hr. The TLC (EtOAc/Petroleum Ether 50:50) showed 2 new products but no starting material. The mixture was filtered through celite and the filtrate concentrated. The residue was purified by flash chromatography on silica using EtOAc/Petroleum Ether 20:80 to eliminate the first product (dimethylated) and then 40:60 to give the expected product as a white solid (12 mg, 28%). $^1$H NMR (ppm, CDCl$_3$): δ 1.87 (s, 6H), 2.44 (s, 3H), 2.54 (q, $J^{HF}$=1.64 Hz, 3H), 4.30 (s, 2H), 5.66 (br s, 2H), 7.34 (d, J=8.1 Hz, 2H), 7.54 (d, J=8.1 Hz, 2H), 8.34 (br s, 1H). $^{13}$C NMR (ppm, CDCl$_3$): δ 21.3, 25.7, 35.6, 56.1, 63.8, 128.3, 130.1, 139.4, 143.5, 153.7, 154.6, 157.39, 158.02. LCMS (+esi): 407.1 (M+H$^+$).

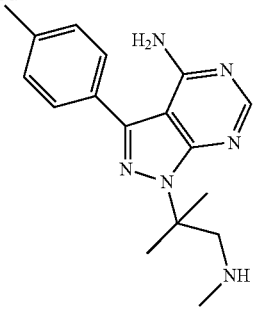

4C: Compound 4B (15.1 mg, 0.04 mmol) was dissolved in 1.5 mL of methanol/water (94:6) and K$_2$CO$_3$ (26.8 mg, 0.194 mmol) was added. The solution was stirred at room temperature for 1 hr. TLC showed starting material left so the mixture was heated at reflux for 2 h. The solvent was removed and 5 mL of water was added. The product was extracted with dichloromethane (3×5 mL), the combined organic layers were washed with water, dried over Na$_2$SO$_4$ and concentrated to give 12.3 mg of compound 4C (82%). $^1$H NMR (ppm, CDCl$_3$): δ 1.83 (s, 6H), 2.43 (s, 3H), 2.45 (s, 3H), 3.27 (s, 2H), 5.52 (br s, 2H), 7.32 (d, J=7.9 Hz, 2H), 7.56 (d, J=7.9 Hz, 2H), 8.31 (br s, 1H). $^{13}$C NMR (ppm, CDCl$_3$): δ 21.3, 25.9, 29.7, 36.9, 56.1, 60.9, 63.4, 128.5, 129.9, 130.6, 138.9, 142.8, 154.5, 157.9. LCMS (+esi): 311.1 (M+H$^+$).

Example 5

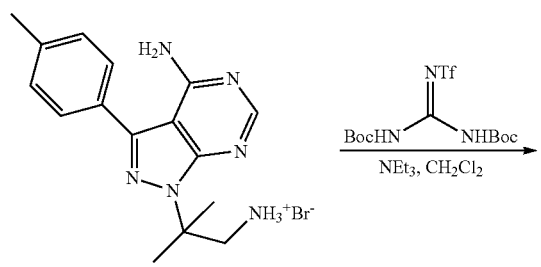

5A: Compound 1E (50 mg, 0.13 mmol), N,N-Di-Boc-N'-triflylguanidine (prepared according to Feichtinger et al., *J. Org. Chem.*, 1998, 63, 8432; 48.7 mg, 0.120 mmol) and triethylamine (37 μL, 0.266 mmol) were dissolved in dry dichloromethane (1 mL). The mixture was stirred at room temperature for 18 hr. It was then diluted in CH$_2$Cl$_2$, washed with 2M sodium bisulfate, saturated sodium bicarbonate and brine. The organic layer was dried over sodium sulfate and concentrated to give a white solid. The crude product was then purified on silica gel using CH$_2$Cl$_2$/MeOH (100:0 to 95:5). A white solid was obtained (m=38.7 mg, 55%). $^1$H NMR (ppm, CDCl$_3$): δ 1.47 (s, 9H), 1.49 (s, 9H), 1.84 (s, 6H), 2.42 (s, 3H), 4.14 (d, J=5.81 Hz, 2H), 5.76 (br s, 2H), 7.30 (d, J=7.92 Hz, 2H), 7.71 (d, J=7.92 Hz, 2H), 8.32 (s, 1H), 9.21 (t, J=5.81 Hz, 1H). $^{13}$C NMR (ppm, CDCl$_3$): δ 21.3, 24.8, 28.1, 28.3, 49.3, 63.0, 79.0, 82.7, 99.8, 128.7, 129.8, 130.5, 138.9, 143.2, 152.8, 154.3, 154.6, 156.7, 158.0, 163.8. LCMS (+esi): 539.0 (M+H$^+$).

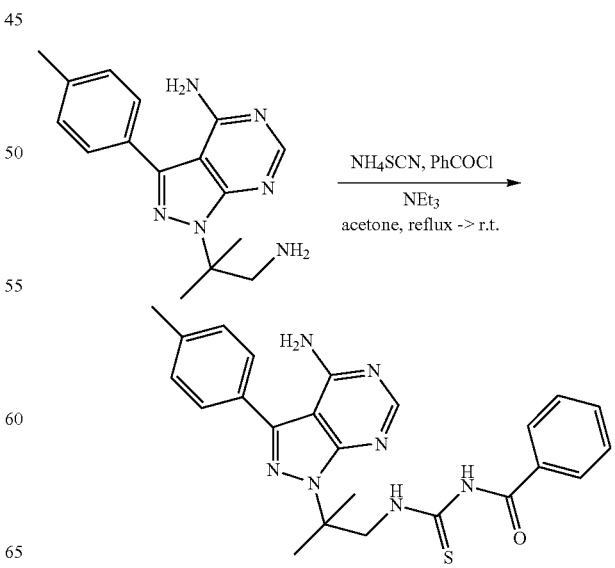

5B: Compound 5A (38.9 mg, 0.072 mmol) was dissolved in 1 mL of dry CH$_2$Cl$_2$ and cooled at 0° C. Then TFA (495 μL, 6.5 mmol) was added dropwise. The mixture was allowed to warm to room temperature and was stirred for 6 hrs. Solvent was removed under vacuum to give a thick brown oil. Toluene was added and evaporated to remove the remaining TFA. The product, still oily, was dissolved in a water/acetonitrile mixture and freeze-dried to give 31.6 mg (78%) of a white solid. $^1$H NMR (ppm, MeOD): δ 1.89 (s, 6H), 2.45 (s, 3H), 3.99 (s, 2H), 7.41 (d, J=6.24 Hz, 2H), 7.60 (d, J=6.90 Hz, 2H), 8.40 (s, 1H). LCMS (+esi): 339.0 (M-2TFA+H$^+$).

Example 6

6A: Compound 1E (50 mg, 0.132 mmol) was free-based by treating a suspension of the hydrobromide salt in CH$_2$Cl$_2$ with saturated aqueous NaHCO$_3$, drying over K$_2$CO$_3$ and concentrating. The residue was dissolved in 1 mL of acetone and triethylamine (18.4 µL, 0.132 mmol) was added. In a separate flask, PhCOCl (21.5 µL., 0.185 mmol,) was added dropwise to a solution of NH$_4$SCN (15.1 mg, 0.198 mmol) in 1 mL of acetone. A white precipitate was observed. The mixture was stirred and heated at reflux for 15 min and then cooled to room temperature. The solution of neutralised 1E in acetone was added quickly and the mixture was stirred at room temperature for 1 h. The mixture was then poured into excess cracked ice with stirring. A white precipitate was formed; it was filtered off and washed with water and then methanol:water (1:1). The solid was dried in a vacuum oven to afford 30 mg of a white powder (49%). $^1$H NMR (ppm, CDCl$_3$): δ 1.92 (s, 6H), 2.44 (s, 3H), 4.58 (d, J=6.09 Hz, 2H), 5.83 (br s, 2H), 7.36 (d, J=7.92 Hz, 2H), 7.50 (t, J=7.8 Hz, 2H), 7.61 (t, J=7.53 Hz, 1H), 7.75 (d, J=8.07 Hz, 2H), 7.81 (d, J=7.26 Hz, 2H), 8.35 (s, 1H), 9.00 (s, 1H).

6B: NaOH aq. 10% (2 mL) was to the crude compound 6A. The mixture was stirred and heated at 90° C. for 1 hr and was then poured in a mixture of HCl 4M and ice. Na$_2$CO$_3$ was added to basify the solution until pH=8-10. The product was extracted with dichloromethane (3 times). The combined organic phases were dried over sodium sulfate and concentrated to afford 12 mg of crude product. LCMS showed a mix of starting material and desired product. The crude mixture was purified by preparative HPLC preparative to afford 1.5 mg (3% yield) of the expected compound. $^1$H NMR (ppm, CDCl$_3$): δ 1.82 (s, 6H), 2.45 (s, 3H), 4.35 (br s, 2H), 6.09 (br s, 1H), 7.37 (d, J=7.53 Hz, 2H), 7.54 (d, J=7.89 Hz, 2H), 8.08 (s, 1H), 8.25 (s, 1H). LCMS (+esi): 356.0 (M+H$^+$).

Example 7

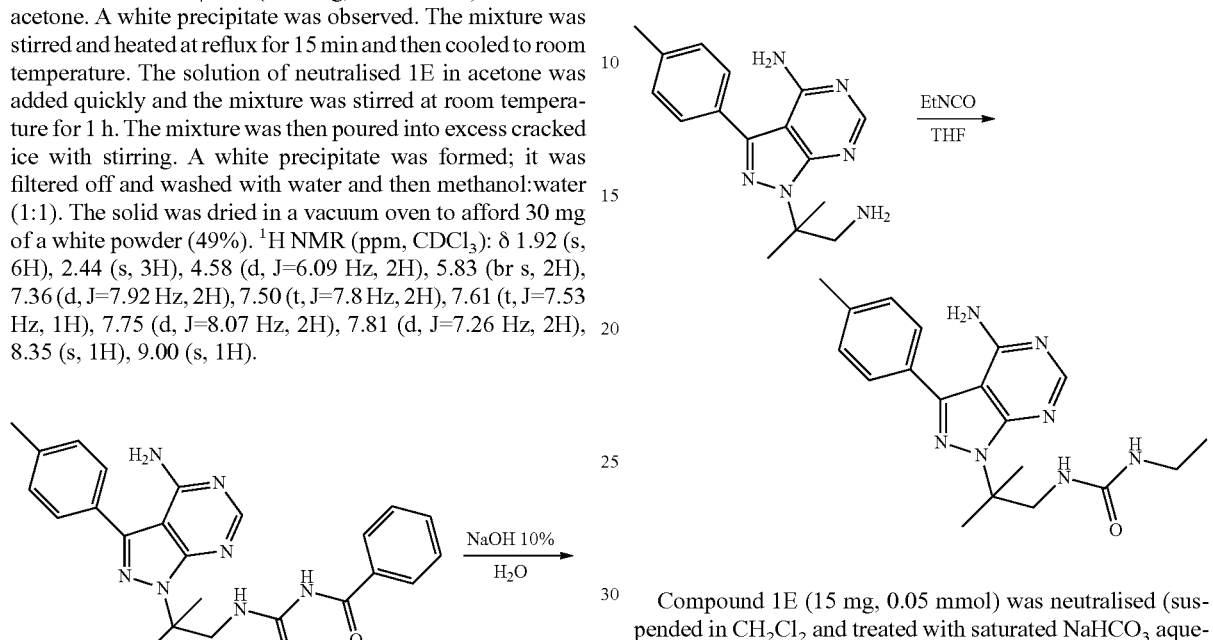

Compound 1E (15 mg, 0.05 mmol) was neutralised (suspended in CH$_2$Cl$_2$ and treated with saturated NaHCO$_3$ aqueous solution, dried over K$_2$CO$_3$ and concentrated). The residue was dissolved in 0.6 mL of dry THF. Ethyl isocyanate (4 µL, 0.05 mmol) was added at 0° C. The solution turned white cloudy. The mixture was stirred overnight and was then diluted with Ether (5 mL), washed with 1M HCl, saturated NaHCO$_3$ and then brine. The organic layer was dried over Na$_2$SO$_4$ and concentrated. As no expected compound was present in the organic layer, the combined aqueous layers were extracted twice with CH$_2$Cl$_2$, dried and concentrated again to give 17.2 mg of a white solid. This crude product was purified on silica gel using MeOH/CH$_2$Cl$_2$ (0:100 to 10:90) to afford 12.7 mg (69%) of a white solid. $^1$H NMR (ppm, CDCl$_3$): δ 1.09 (t, J=7.2 Hz, 3H), 1.77 (s, 6H), 2.44 (s, 3H), 3.16 (q, J=6.96 Hz, 2H), 3.93 (d, J=4.38 Hz, 2H), 4.44 (br s, 1H), 5.68 (br s, 2H), 5.81 (br s, 1H), 7.34 (d, J=7.77 Hz, 2H), 7.54 (d, J=7.92 Hz, 2H), 8.30 (s, 1H). LCMS (+esi): 368.0 (M+H$^+$).

Example 8

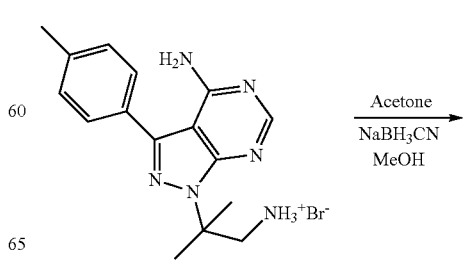

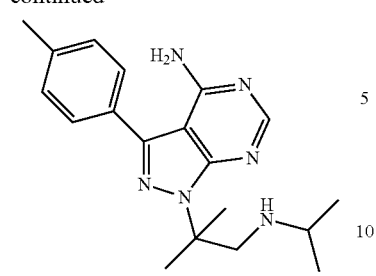

Compound 1E (50 mg, 0.132 mmol), acetone (48.5 μL, 0.66 mmol) and NaBH₃CN (33 mg, 0.53 mmol) were dissolved in 1.5 mL of methanol. The mixture was stirred at room temperature for 3 days (the reaction was monitored by TLC 10% MeOH in CH₂Cl₂). Solvents and volatiles were removed in vacuum, water. The residue was dissolved in CH₂Cl₂. The aqueous layer was extracted 3 times with CH₂Cl₂. The combined organic layers were washed with brine, dried over sodium sulfate and concentrated to afford 34 mg of a colourless oil. The crude was purified on silica gel using MeOH/CH₂Cl₂, (0:100 to 6:94). A white solid was obtained (m=21 mg, 47%). ¹H NMR (ppm, CDCl₃): δ 1.01 (d, J=6.27 Hz, 6H), 1.82 (s, 6H), 2.45 (s, 3H), 2.76 (hept, J=6.36 Hz, 1H), 3.27 (s, 2H), 5.62 (br s, 2H), 7.32 (d, J=8.37 Hz, 2H), 7.56 (d, J=8.04 Hz, 2H), 8.30 (s, 1H). LCMS (+esi): 338.4 (M+H⁺).

Example 9

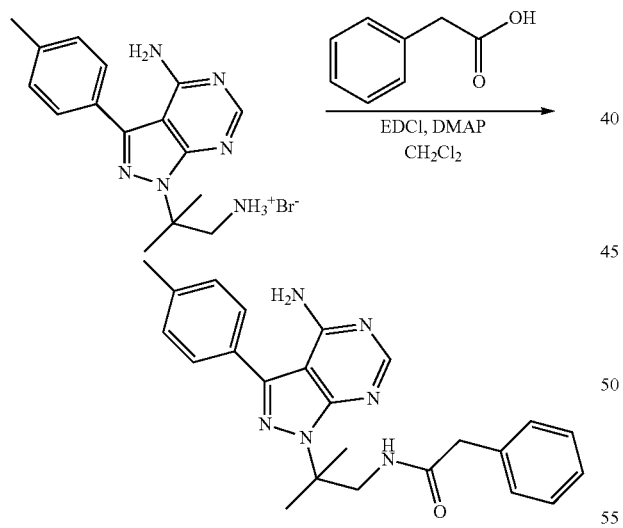

Compound 1E (50 mg, 0.132 mmol), DMAP (49 mg, 0.40 mmol), phenyl acetic acid (20 mg, 0.145 mmol) and EDCI (33 mg, 0.172 mmol) were dissolved in 2 mL of dry CH₂Cl₂. The reaction was stirred at room temperature for 3 hours. The reaction was diluted with CH₂Cl₂ and washed successively with HCl 1N, NaHCO₃sat., water and brine. The organic layer was dried over Na₂SO₄ and concentrated. NMR and LCMS indicated that the compound was pure (m=31 mg, 56%). ¹H NMR (ppm, CDCl₃): δ 1.71 (s, 6H), 2.46 (s, 3H), 3.59 (s, 2H), 3.92 (d, J=6.42 Hz, 2H), 5.74 (br s, 2H), 6.96 (br t, J=6.06 Hz, 1H), 7.16 (s, 5H), 7.33 (d, J=7.92 Hz, 2H), 7.39 (d, J=8.19 Hz, 2H), 8.12 (s, 1H). LCMS (+esi): 415.0 (M+H⁺).

Example 10

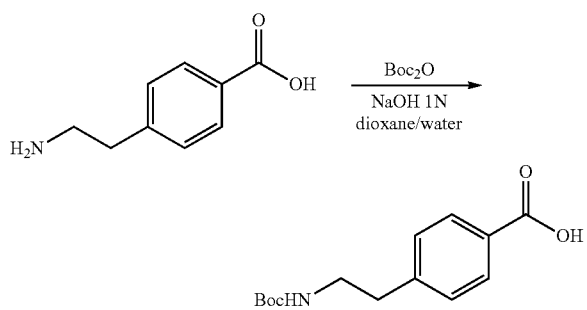

10A: 4-(2-aminethyl)-benzoic acid (200 mg, 0.99 mmol) and Boc₂O (260 mg, 1.2 mmol) were dissolved in 1 mL of 1M aqueous NaOH. The reaction was stirred at room temperature for 4 hrs. After this time, ethyl acetate was added followed by 10% aqueous solution of citric acid. A white solid precipitated. It was removed by filtration. The filtrate was then extracted three times with ethyl acetate. The combined organic layers were washed with water and brine, dried over Na₂SO₄ and concentrated. The residue was purified by flash chromatography on SiO₂ using CH₂Cl₂/MeOH (100:0 to 95:5). A white solid was obtained (m=47 mg, 16%). ¹H NMR (ppm, CDCl₃): δ 1.33 (s, 9H), 2.74 (t, J=7.44 Hz, 2H), 3.14 (guar, J=6.78 Hz, 2H), 6.84 (br t, J=5.43 Hz, 1H), 7.28 (d, J=8.28 Hz, 2H), 7.83 (d, J=8.25 Hz, 2H).

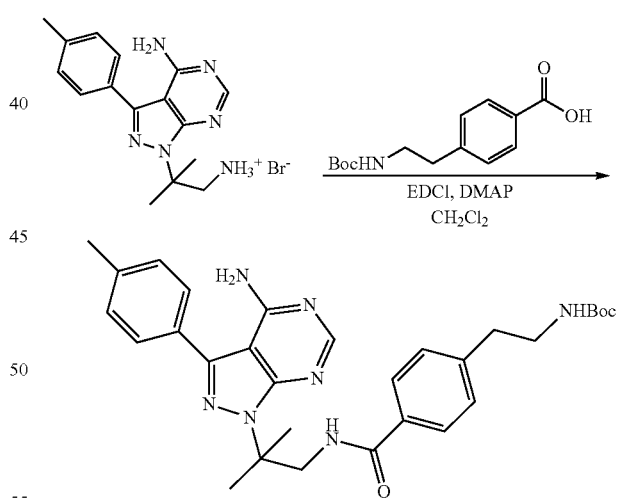

10B: Compound 10B was prepared using the same procedure described in example 1E using compound 1E (20 mg, 0.053 mmol) and compound 10A. After work up the resulting crude compound was purified by flash chromatography on SiO₂ using CH₂Cl₂/MeOH (99:1 to 98:2). A white solid was obtained (m=15 mg, 53%). ¹H NMR (ppm, CDCl₃): δ 1.41 (s, 9H), 1.83 (s, 6H), 2.44 (s, 3H), 2.83 (t, J=6.9 Hz, 2H), 3.37 (br quar, J=6.72 Hz, 2H), 4.12 (d, J=6.12 Hz, 2H), 4.58 (br s, 1H), 5.78 (br s, 1H), 7.23 (d, J=7.95 Hz, 2H), 7.36 (d, J=8.28 Hz, 2H), 7.56 (d, J=8.07 Hz, 2H), 7.74 (d, J=8.01 Hz, 2H), 8.35 (br s, 2H overlapping).

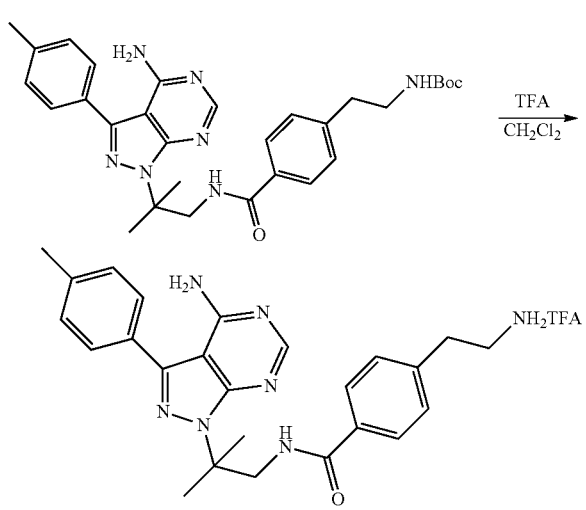

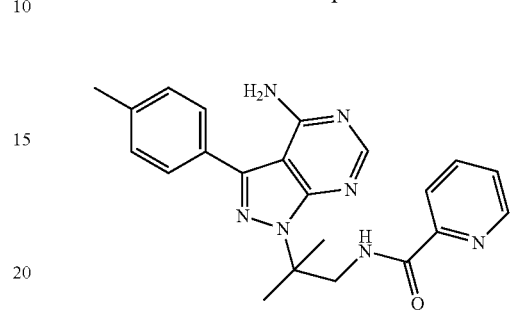

10C: Compound 10B (15 mg, 0.03 mmol) dissolved in 1 mL of CH$_2$Cl$_2$ was treated with 200 µL of TFA. The reaction was stirred at room temperature for 16 hrs. 200 µL of TFA was added and the reaction was left for a further 24 hours. The TFA was removed by azeotroping with toluene (3 times) to afford a colourless oil. A white solid precipitated upon addition of Et$_2$O. The solid was collected by filtration, rinsed with Et$_2$O and dried in a vacuum oven. NMR (ppm, CDCl$_3$): δ 1.81 (s, 6H), 2.38 (s, 3H), 2.92 (br s, 2H), 3.07 (br s, 2H), 4.02 (br s, 2H), 7.10 (br s, 2H), 7.26-7.31 (m, 2H), 7.29-7.46 (m, 4H), 7.72 (br s, 2H), 8.6 (br s, 3H). LCMS (+esi): 444.1 (M+H$^+$).

Example 11

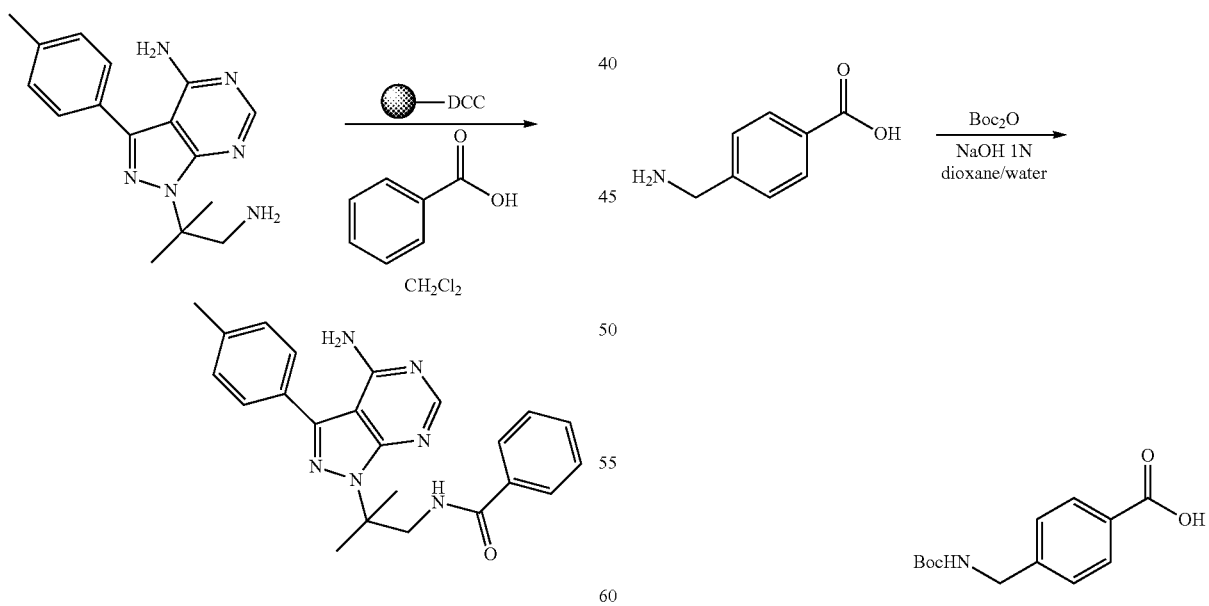

Compound from example 1E (64 mg, 0.17 mmol) was neutralised by treating a suspension of the hydrobromide salt in CH$_2$Cl$_2$ with saturated aqueous NaHCO$_3$, drying over K$_2$CO$_3$ and concentrating. The residue was dissolved in CH$_2$Cl$_2$ and benzoic acid (22 mg, 0.18 mmol) followed by solid supported DCC (Novabiochem, 390 mg, 0.51 mmol) were added and the reaction was placed on an orbital shaker for 24 hrs. The reaction was then filtered through a pad of celite. The solids were rinsed with CH$_2$Cl$_2$. Concentration afforded a colourless oil (m=40 mg, 59%). $^1$H NMR (ppm, CDCl$_3$): δ 1.85 (s, 6H), 2.44 (s, 3H), 4.14 (d, J=6.18 Hz, 2H), 5.69 (br s, 2H), 7.34-7.48 (m, 5H), 7.57 (d, J=8.1 Hz, 2H), 7.81 (t d, J=8.37 Hz, 2H), 8.37 (s, 1H), 8.39 (br t, 1H). LCMS (+esi): 401.1 (M+H$^+$).

Example 12

Compound 12: Compound 12 was prepared according to the procedure used to prepare compound from example 11 using picolinic acid (22 mg, 0.18 mmol). The off-white solids obtained were triturated with Et$_2$O, collected by filtration and rinsed with more Et$_2$O. A white powder was obtained (15 mg, 22%). NMR (ppm, CDCl$_3$): δ 1.87 (s, 6H), 2.46 (s, 3H), 4.20 (d, J=6.66 Hz, 2H), 5.75 (br s, 2H), 7.37 (d, J=7.68 Hz, 2H), 7.41-7.43 (m, 1H), 7.69 (d, J=8.1 Hz, 2H), 7.83 (t d, J=7.71, 1.65 Hz, 1H), 8.20 (d, J=7.83 Hz, 1H), 8.37 (s, 1H), 8.55 (d, J=4.8 Hz, 1H), 9.23 (br t, J=6.06 Hz, 1H). LCMS (+esi): 402.1 (M+H$^+$).

Example 13

13A: Compound 13A was prepared according to the procedure described for example 10A with 4-amino-methyl benzoic acid (200 mg, 1.94 mmol). A white solid was obtained (m=232 mg, 52%). $^1$H NMR (ppm, CDCl$_3$): δ 1.47 (s, 9H), 4.39 (br d, J=5.19 Hz, 2H), 4.94 (br s, 1H), 7.38 (d, J=8.4 Hz, 2H), 8.06 (d, J=8.31 Hz, 2H).

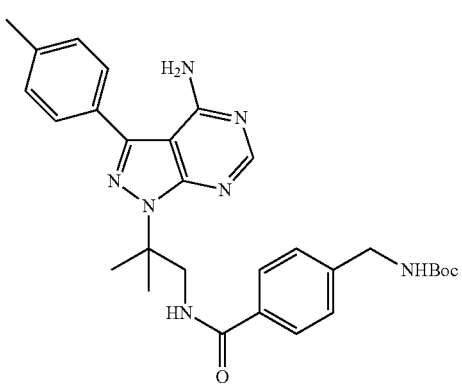

13B: Compound 13B was prepared according to the procedure described for example 11, using 13A. The product was obtained as a white foam. ¹H NMR (ppm, CDCl₃): δ 1.45 (s, 9H), 1.84 (s, 6H), 2.45 (s, 3H), 2.82 (br s, 1H), 4.11 (d, J=6.21 Hz, 2H), 4.33 (d, J=5.82 Hz, 2H), 4.95 (br s, 1H), 5.78 (br s, 1H), 7.33 (dd, J=2.25 Hz, 8.46 Hz, 4H), 7.55 (d, J=8.07 Hz, 2H), 7.77 (d, J=8.31 Hz, 2H), 8.33 (br s, 1H), 8.35 (s, 1H).

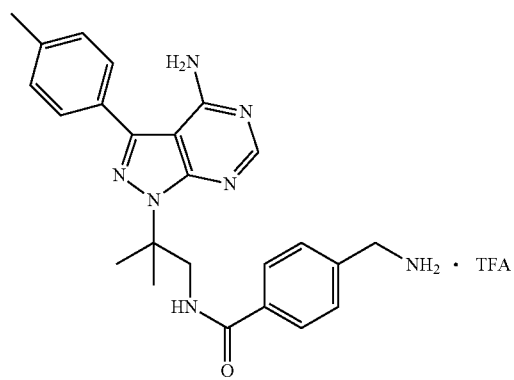

13C: Compound 13C was prepared according to the procedure described for compound 10C, using 13B as the BOC-protected amine. ¹H NMR (ppm, CDCl₃): δ 1.88 (s, 6H), 2.42 (s, 3H), 4.02 (m, 4H), 6.37 (br s, 2H), 7.34-7.51 (m, 8H), 8.13 (br s, 1H), 8.40 (br s, 2H), 10.41 (br s, 1H). LCMS (+esi): 430.3 (M+H⁺).

Example 14

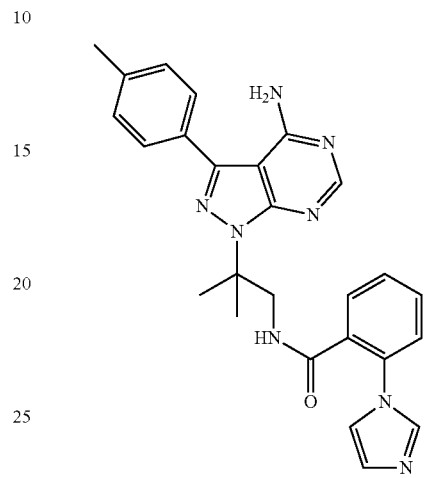

Compound 14 was prepared according to the procedure described for example 11, using 2-(1H-imidazol-1-yl)benzoic acid (6.7 mg, 0.04 mmol). The expected product was obtained as a white solid (10.3 mg, 55%). ¹H NMR (ppm, CDCl₃): δ 1.72 (s, 6H), 2.42 (s, 3H), 3.98 (d, J=6.30 Hz, 2H), 5.68 (br s, 2H), 7.01 (bs, 1H), 7.05 (br s, 1H), 7.29 (d, J=1.44 Hz, 1H), 7.32 (s. 1H), 7.35 (s, 1H), 7.41 (bs, 1H), 7.45 (d, J=1.41 Hz, 1H), 7.47 (d, J=1.65 Hz, 1H), 7.49 (d, J=2.01 Hz, 1H), 7.51 (s, 1H), 7.54 (s, 1H), 7.65 (d, J=1.83 Hz, 1H), 7.68 (d, J=1.62 Hz, 1H), 8.22 (s, 1H). LCMS (+esi): 467.2 (M+H⁺).

Similarly, the following examples were prepared from the corresponding acids:

| Example | Structure | Characterisation Data |
| --- | --- | --- |
| 15 | 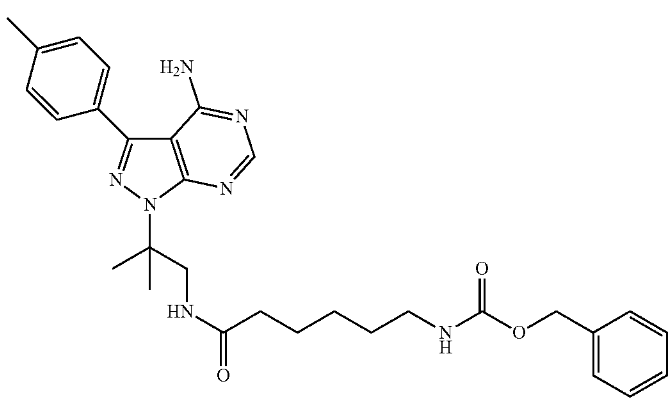 [SMILES: Cc1ccc(-c2nn(C(C)(C)CNC(=O)CCCCCNC(=O)OCc3ccccc3)c3ncnc(N)c23)cc1] | LCMS (+esi): 544.0 (M + H⁺) |

| Example | Structure | Characterisation Data |
|---|---|---|
| 16 | 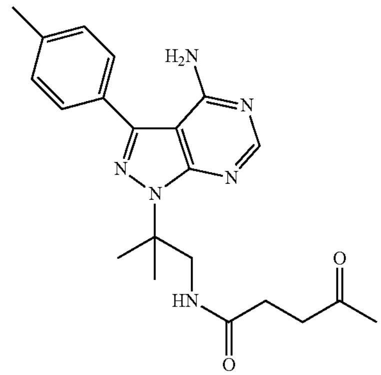 [SMILES: CC(=O)CCC(=O)NCC(C)(C)n1nc(-c2ccc(C)cc2)c2c(N)ncnc21] | LCMS (+esi): 394.9 (M + H⁺) |
| 17 | 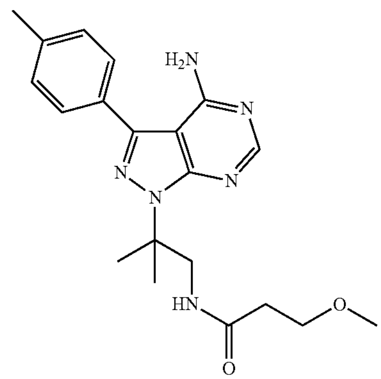 | LCMS (+esi): 382.8 (M + H⁺) |
| 18 | 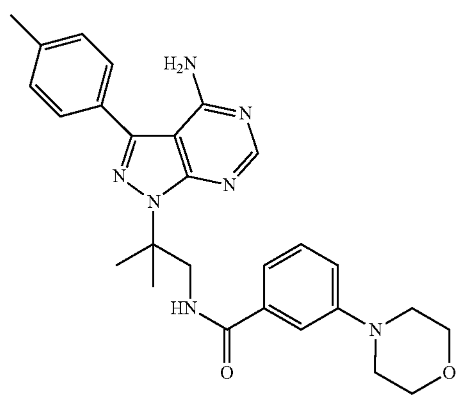 [SMILES: Cc1ccc(-c2nn(C(C)(C)CNC(=O)c3cccc(N4CCOCC4)c3)c3ncnc(N)c23)cc1] | LCMS (+esi): 486.1 (M + H⁺) |
| 19 | 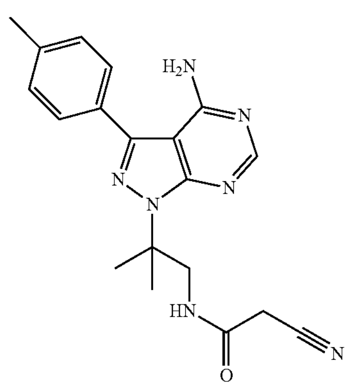 [SMILES: Cc1ccc(-c2nn(C(C)(C)CNC(=O)CC#N)c3ncnc(N)c23)cc1] | LCMS (+esi): 364.2 (M + H⁺) |

-continued

| Example | Structure | Characterisation Data |
|---------|-----------|-----------------------|
| 20 | 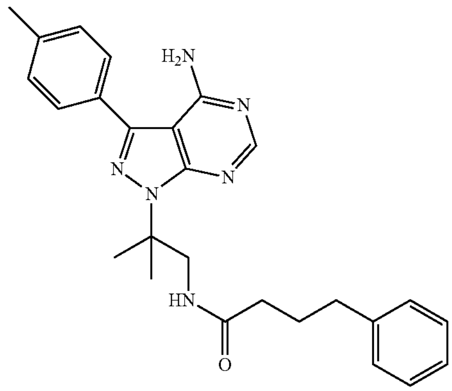 [SMILES: Cc1ccc(-c2nn(C(C)(C)CNC(=O)CCCc3ccccc3)c3ncnc(N)c23)cc1] | LCMS (+esi): 443.3 (M + H$^+$) |
| 21 | 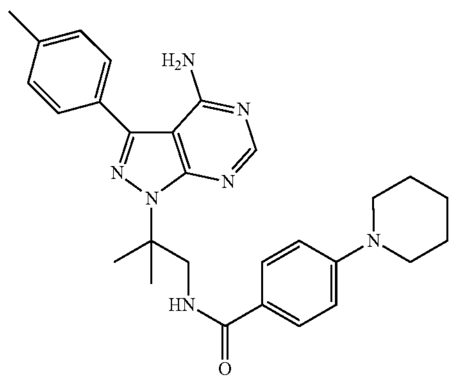 [SMILES: Cc1ccc(-c2nn(C(C)(C)CNC(=O)c3ccc(N4CCCCC4)cc3)c3ncnc(N)c23)cc1] | LCMS (+esi): 484.3 (M + H$^+$) |
| 22 | 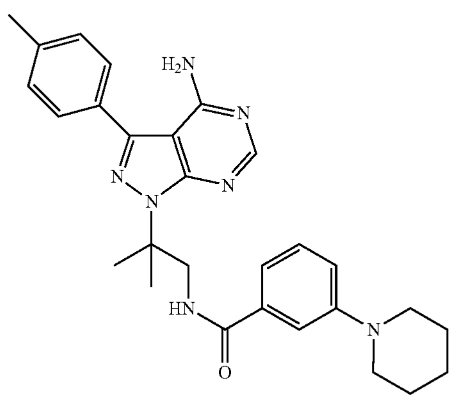 [SMILES: Cc1ccc(-c2nn(C(C)(C)CNC(=O)c3cccc(N4CCCCC4)c3)c3ncnc(N)c23)cc1] | LCMS (+esi): 484.2 (M + H$^+$) |
| 23 | 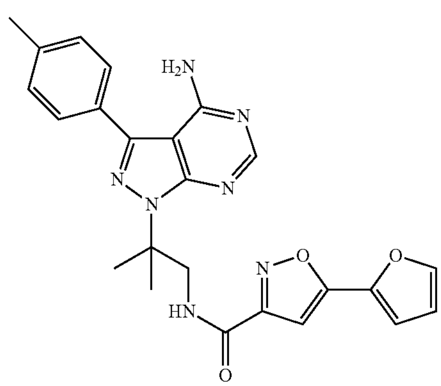 [SMILES: Cc1ccc(-c2nn(C(C)(C)CNC(=O)c3cc(-c4ccco4)on3)c3ncnc(N)c23)cc1] | LCMS (+esi): 458.1 (M + H$^+$) |

| Example | Structure | Characterisation Data |
|---|---|---|
| 24 | 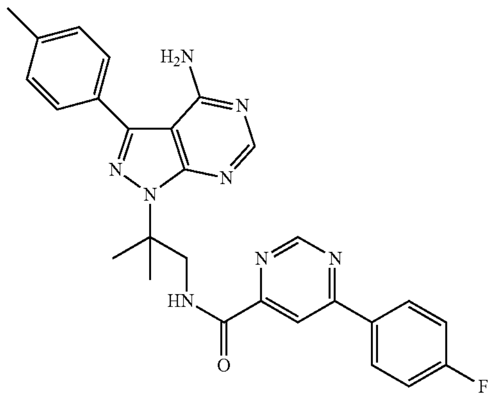 [SMILES: Cc1ccc(-c2nn(C(C)(C)CNC(=O)c3cc(-c4ccc(F)cc4)ncn3)c3ncnc(N)c23)cc1] | LCMS (+esi): 497.2 (M + H⁺) |
| 25 | 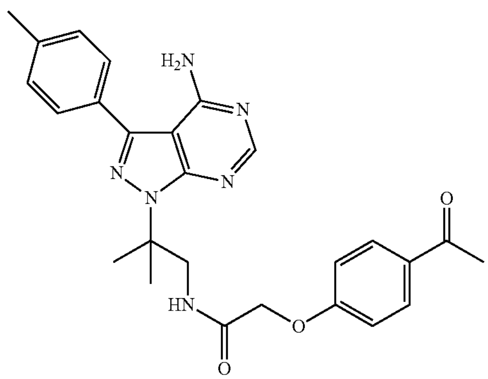 [SMILES: CC(=O)c1ccc(OCC(=O)NCC(C)(C)n2nc(-c3ccc(C)cc3)c3c(N)ncnc32)cc1] | LCMS (+esi): 473.2 (M + H⁺) |
| 26 | 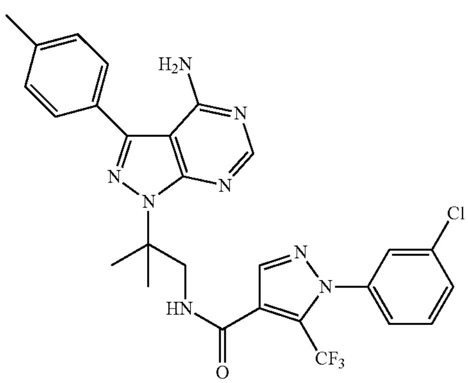 [SMILES: Cc1ccc(-c2nn(C(C)(C)CNC(=O)c3cnn(-c4cccc(Cl)c4)c3C(F)(F)F)c3ncnc(N)c23)cc1] | LCMS (+esi): 569.3 (M + H⁺) |
| 27 | 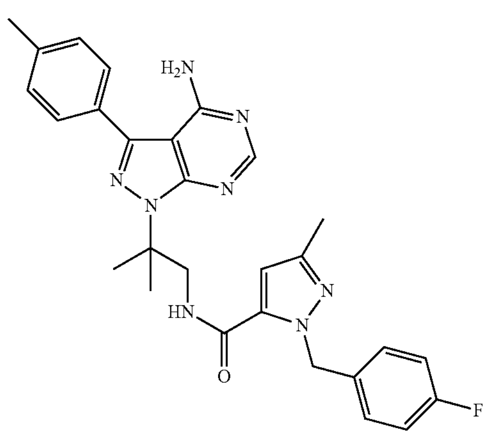 [SMILES: Cc1ccc(-c2nn(C(C)(C)CNC(=O)c3cc(C)nn3Cc3ccc(F)cc3)c3ncnc(N)c23)cc1] | LCMS (+esi): 513.2 (M + H⁺) |

-continued

| Example | Structure | Characterisation Data |
|---|---|---|
| 28 | 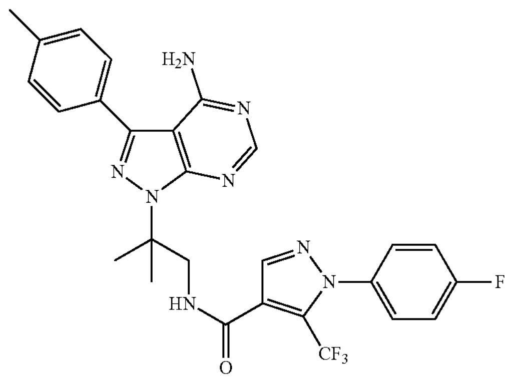 [SMILES: Cc1ccc(-c2nn(C(C)(C)CNC(=O)c3cnn(-c4ccc(F)cc4)c3C(F)(F)F)c3ncnc(N)c23)cc1] | LCMS (+esi): 553.2 (M + H⁺) |
| 29 | 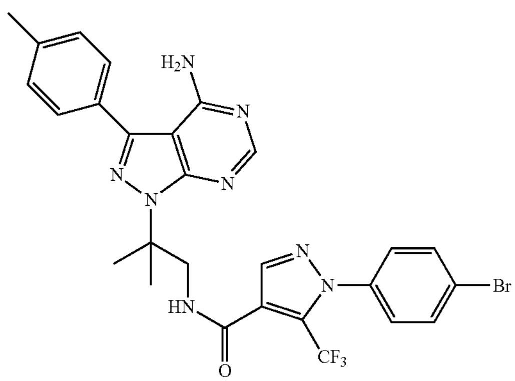 [SMILES: Cc1ccc(-c2nn(C(C)(C)CNC(=O)c3cnn(-c4ccc(Br)cc4)c3C(F)(F)F)c3ncnc(N)c23)cc1] | LCMS (+esi): 613.2 (M + H⁺) |
| 30 | 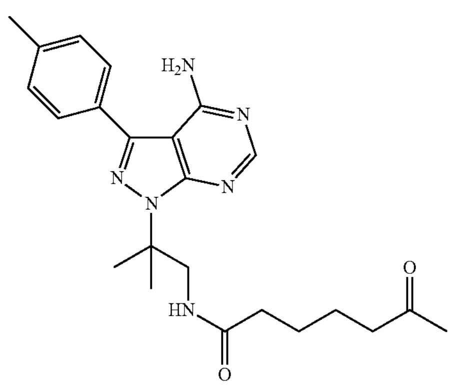 [SMILES: CC(=O)CCCCC(=O)NCC(C)(C)n1nc(-c2ccc(C)cc2)c2c(N)ncnc21] | LCMS (+esi): 423.0 (M + H⁺) |
| 31 | 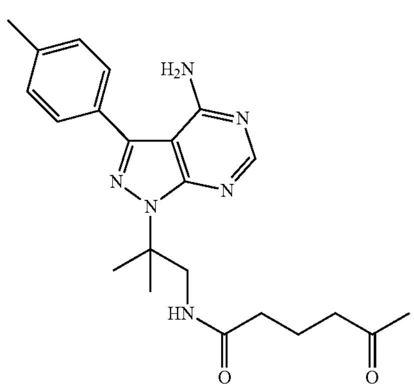 [SMILES: CC(=O)CCCC(=O)NCC(C)(C)n1nc(-c2ccc(C)cc2)c2c(N)ncnc21] | LCMS (+esi): 409.1 (M + H⁺) |

-continued

| Example | Structure | Characterisation Data |
|---|---|---|
| 32 | 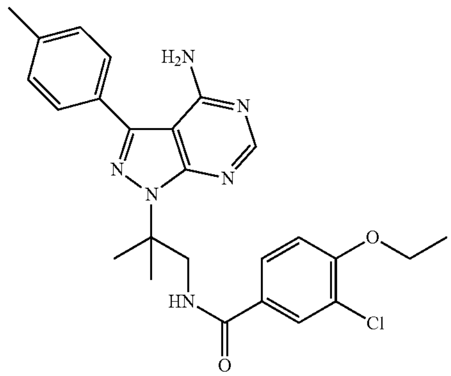 [SMILES: CCOc1ccc(C(=O)NCC(C)(C)n2nc(-c3ccc(C)cc3)c3c(N)ncnc32)cc1Cl] | LCMS (+esi): 479.2 (M + H$^+$) |
| 33 | 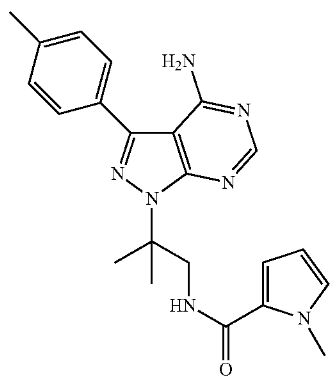 [SMILES: Cc1ccc(-c2nn(C(C)(C)CNC(=O)c3cccn3C)c3ncnc(N)c23)cc1] | LCMS (+esi): 404.2 (M + H$^+$) |
| 34 | 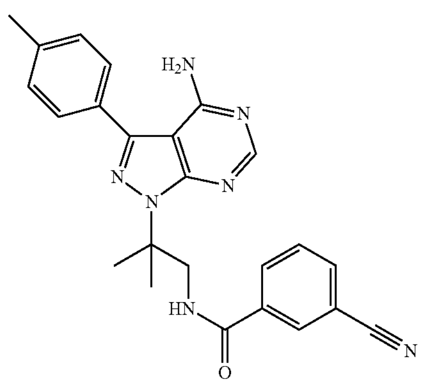 [SMILES: Cc1ccc(-c2nn(C(C)(C)CNC(=O)c3cccc(C#N)c3)c3ncnc(N)c23)cc1] | LCMS (+esi): 426.4 (M + H$^+$) |
| 35 | 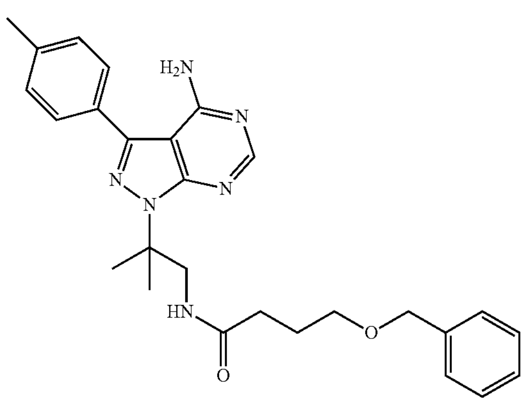 [SMILES: Cc1ccc(-c2nn(C(C)(C)CNC(=O)CCCOCc3ccccc3)c3ncnc(N)c23)cc1] | LCMS (+esi): 473.2 (M + H$^+$) |

-continued

| Example | Structure | Characterisation Data |
|---|---|---|
| 36 | 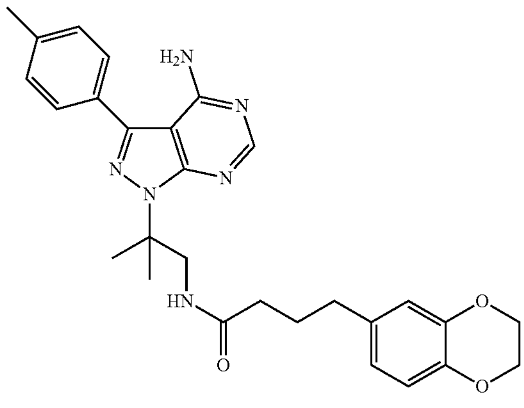 [SMILES: Cc1ccc(-c2nn(C(C)(C)CNC(=O)CCCc3ccc4c(c3)OCCO4)c3ncnc(N)c23)cc1] | LCMS (+esi): 501.3 (M + H⁺) |
| 37 | 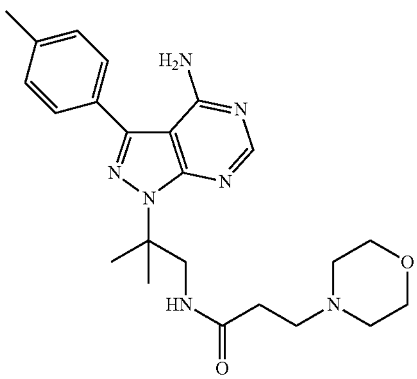 [SMILES: Cc1ccc(-c2nn(C(C)(C)CNC(=O)CCN3CCOCC3)c3ncnc(N)c23)cc1] | LCMS (+esi): 438.1 (M + H⁺) |
| 38 | 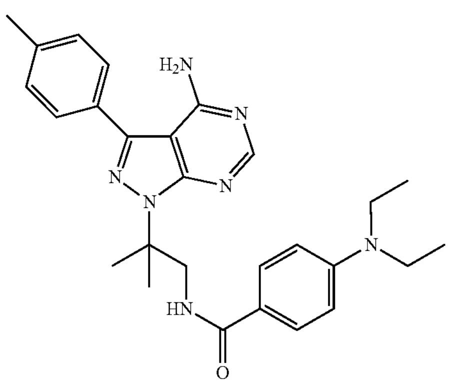 [SMILES: CCN(CC)c1ccc(C(=O)NCC(C)(C)n2nc(-c3ccc(C)cc3)c3c(N)ncnc32)cc1] | LCMS (+esi): 472.1 (M + H⁺) |
| 39 | 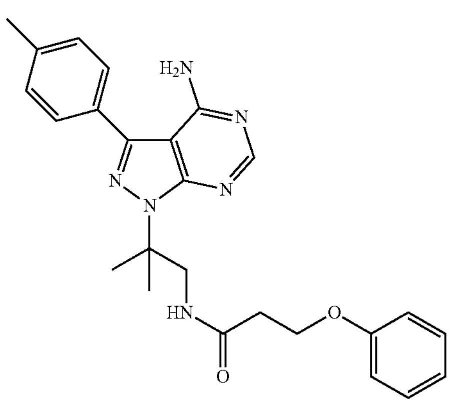 [SMILES: Cc1ccc(-c2nn(C(C)(C)CNC(=O)CCOc3ccccc3)c3ncnc(N)c23)cc1] | LCMS (+esi): 444.9 (M + H⁺) |

Example 40

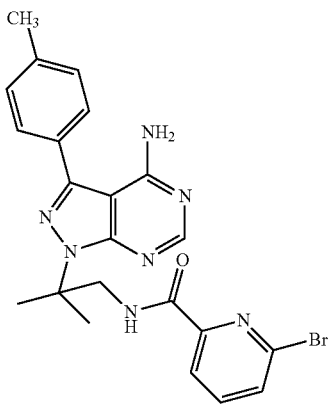 [SMILES: Cc1ccc(-c2nn(C(C)(C)CNC(=O)c3cccc(Br)n3)c3ncnc(N)c23)cc1]

Compound 40 was prepared according to the procedure described for example 11 using 6-bromopicolinic acid (17.9 mg, 88.7/mot). A white solid was obtained (3.4 mg, 8%). ¹H NMR (ppm, CDCl₃): δ 9.35 (s, 1H), 8.43-8.12 (m, 3H), 7.79-7.22 (m, 5H), 5.61 (br s, 2H), 4.18 (d, J=6.5 Hz, 1H), 2.42 (s, 3H), 1.78 (s, 6H). LCMS (+esi): 482.0 (M+H⁺), RT=6.96 min.

Example 41

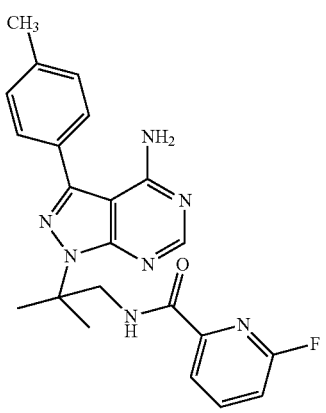 [SMILES: Cc1ccc(-c2nn(C(C)(C)CNC(=O)c3cccc(F)n3)c3ncnc(N)c23)cc1]

Compound 41 was prepared according to the procedure described for example 11 using 6-fluoropicolinic acid (12.5 mg, 88.7 μmol). A cream solid was obtained (19.9 mg, 54%). ¹H NMR (ppm, CDCl₃): δ 9.27 (s, 1H), 8.38-7.06 (m, 8H), 5.82 (br s, 2H), 4.16 (d, J=6.5 Hz, 1H), 2.49 (s, 3H), 1.89 (s, 6H). LCMS (+esi): 420.1 (M+H⁺), RT=6.71 min.

Example 42

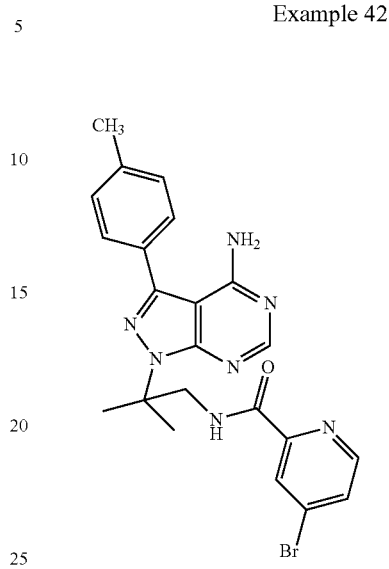

Example 42 was prepared according to the procedure described for example 11 using 4-bromopicolinic acid (17.9 mg, 88.7 μmol). A dark cream solid was obtained (18.6 mg, 43%). ¹H NMR (ppm, CDCl₃): δ 9.02 (s, 1H), 8.41-8.30 (m, 3H), 7.68-7.36 (m, 5H), 5.30 (s, 2H), 4.16 (d, J=6.6 Hz, 1H), 2.45 (s, 3H), 1.75 (s, 6H). LCMS (+esi): 482.0 (M+H⁺), RT=7.05 min.

Example 43

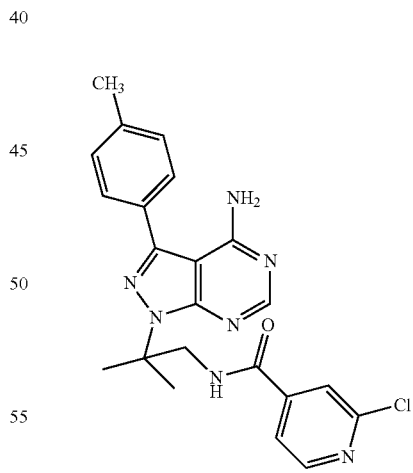

Compound 43 was prepared according to the procedure described for example 11 using 2-chloroisonicotinic acid (12.7 mg, 88.7 μmol) A yellow solid was obtained (27.5 mg, 75%). ¹H NMR (ppm, CDCl₃): δ 9.03 (s, 1H), 8.50-8.39 (m, 3H), 7.76-7.27 (m, 5H), 5.89 (s, 2H), 4.09 (d, J=6.7 Hz, 1H), 2.47 (s, 3H), 1.83 (s, 6H). LCMS (+esi): 436.1 (M+H⁺), RT=6.36 min.

Example 44

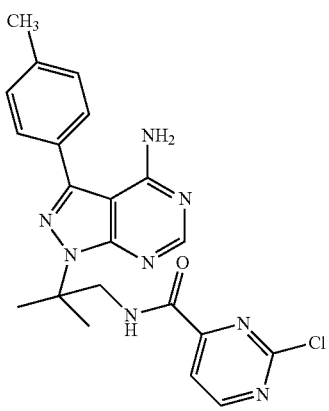 [SMILES: Cc1ccc(-c2nn(C(C)(C)CNC(=O)c3ccnc(Cl)n3)c3ncnc(N)c23)cc1]

Compound 44 was prepared according to the procedure described for example 11 using 2-chloropyrimidine-4-carboxylic acid (14.1 mg, 88.7 μmol). A cream solid was obtained (18.4 mg, 50%). $^1$H NMR (ppm, CDCl$_3$): δ 9.62 (s, 1H), 8.85-7.38 (m, 7H), 5.60 (br s, 2H), 4.16 (d, J=6.8 Hz, 2H), 2.49 (s, 3H), 1.88 (s, 6H). LCMS (+esi): 437.0 (M+H$^+$), RT=6.64 min.

Example 45

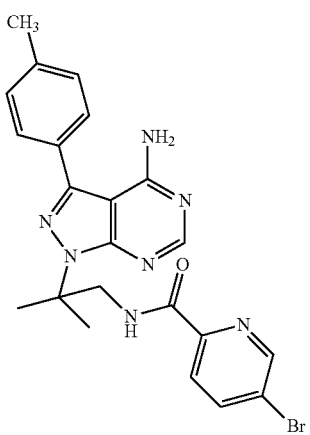 [SMILES: Cc1ccc(-c2nn(C(C)(C)CNC(=O)c3ccc(Br)cn3)c3ncnc(N)c23)cc1]

Compound 45 was prepared according to the procedure described for example 11 using 5-bromopicolinic acid (17.9 mg, 88.7 μmol). A white solid was obtained (10 mg, 25%). LCMS (+esi): 482.0 (M+H$^+$), RT=6.28 min.

Example 46

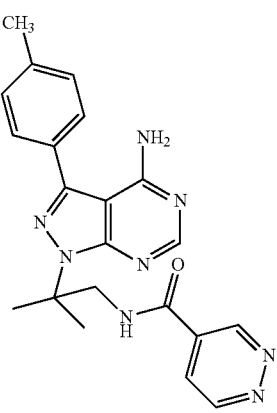 [SMILES: Cc1ccc(-c2nn(C(C)(C)CNC(=O)c3ccnnc3)c3ncnc(N)c23)cc1]

Compound 46 was prepared according to the procedure described for example 11 using pyridazine-4-carboxylic acid (11.0 mg, 88.7 μmol). A cream solid was obtained (18.0 mg, 53%). $^1$H NMR (ppm, CDCl$_3$): δ 9.58 (s, 1H), 8.39-7.28 (m, 8H), 5.25 (br s, 2H), 4.16 (d, J=6.6 Hz, 2H), 2.45 (s, 3H), 1.77 (s, 6H). LCMS (+esi): 403.1 (M+H$^+$), RT=5.68 min.

Example 47

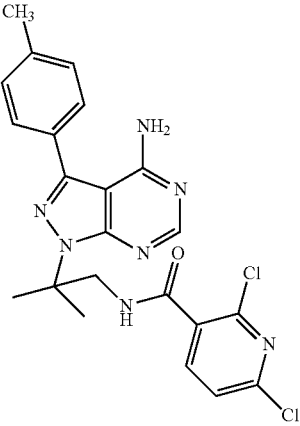 [SMILES: Cc1ccc(-c2nn(C(C)(C)CNC(=O)c3ccc(Cl)nc3Cl)c3ncnc(N)c23)cc1]

Compound 47 was prepared according to the procedure described for example 11 using 2,6-dichloronicotinic acid (16.9 mg, 88.7 μmol). A cream solid was obtained (19.7 mg, 49%). $^1$H NMR (ppm, CDCl$_3$): δ 8.30-8.09 (m, 2H), 8.18 (s, 1H), 7.54-7.26 (m, 5H), 7.26 (s, 2H), 4.20 (d, J=6.4 Hz, 2H), 2.44 (s, 3H), 1.88 (s, 6H). LCMS (+esi): 470.0 (M+H$^+$), RT=6.49 min.

Example 48

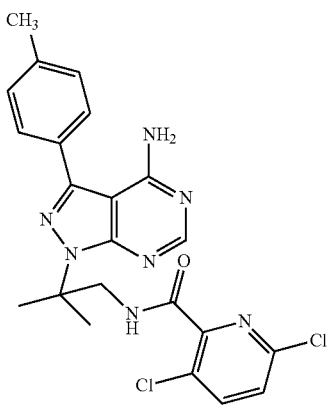 [SMILES: Cc1ccc(-c2nn(C(C)(C)CNC(=O)c3nc(Cl)ccc3Cl)c3ncnc(N)c23)cc1]

Compound 48 was prepared according to the procedure described for example 11 using 3,6-dichloropicolinic acid (16.2 mg, 88.7 μmol). A cream solid (17.9 mg, 45%) was obtained. $^1$H NMR (ppm, CDCl$_3$): δ 9.16 (s, 1H), 8.40-8.19 (m, 2H), 7.76-7.57 (m, 5H), 5.57 (s, 2H), 4.12 (d, J=6.3 Hz, 2H), 2.16 (s, 3H), 1.76 (s, 6H). LCMS (+esi): 470.0 (M+H$^+$), RT=6.76 min.

Example 49

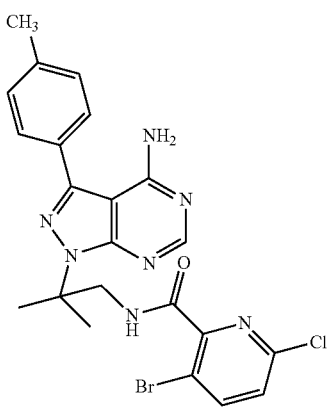 [SMILES: Cc1ccc(-c2nn(C(C)(C)CNC(=O)c3nc(Cl)ccc3Br)c3ncnc(N)c23)cc1]

Compound 49 was prepared according to the procedure described for example 11 using 3-bromo-6-chloropicolinic acid (20.0 mg, 88.7 μmol). A white solid was obtained (24.6 mg, 56%). $^1$H NMR (ppm, CDCl$_3$): δ 8.95 (s, 1H), 8.35-7.33 (m, 7H), 5.71 (s, 2H), 4.12 (d, J=6.6 Hz, 2H), 2.44 (s, 3H), 1.85 (s, 6H). LCMS (+esi): 516.0 (M+H$^+$), RT=6.90 min.

Example 50

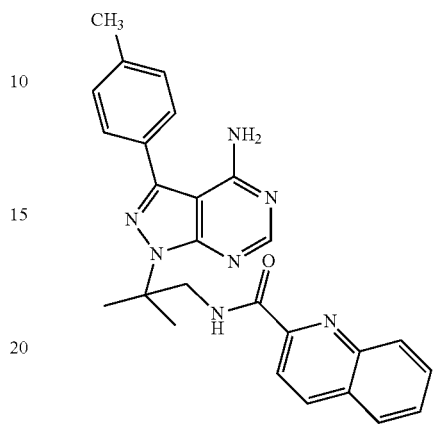

To a stirred solution of lithium hydroxide (20.0 mg, 0.84 mmol) in water (1 mL), methyl quinoline-2-carboxylate (20.0 mg, 0.11 mmol) in methanol (3 mL) was added. The solution was left to stir at room temperature for 2 h. The solution was then concentrated in vacuo. The yellow solid residue was dissolved in water and made acidic with concentrated hydrochloric acid. The organic material was extracted with ethyl acetate. The organic layers were dried with anhydrous sodium sulphate, filtered, and concentrated in vacuo to yield quinoline-2-carboxylic acid as a white solid.

Compound 50 was prepared according to the procedure described for example 11 using quinoline-2-carboxylic acid (16.6 mg, 88.7 μmol). A white solid was obtained (23.4 mg, 61%). $^1$H NMR (ppm, CDCl$_3$): δ 8.32 (d, 1H), 7.58 (s, 1H), 7.58 (s, 1H), 7.56 (d, 1H), 7.55 (d, 1H), 7.34 (m, 1H), 7.31 (m, 1H), 5.50 (s, 1H), 5.30 (s, 4H), 3.38 (s, 2H), 2.43 (s, 6H), 2.17 (s, 2H), 1.73 (s, 3H). LCMS (+esi): 440.1 (M+H$^+$), RT=5.78 min.

Example 51

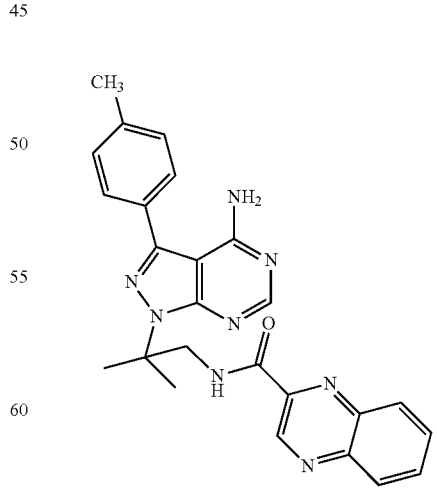

To a stirred solution of lithium hydroxide (20.0 mg, 0.84 mmol) in water (1 mL), ethyl quinoxaline-2-carboxylate (20.0 mg, 0.99 mmol) in methanol (3 mL) was added. The solution was left to stir at room temperature for 2 h. The solution was concentrated in vacuo. This cream solid residue was dissolved in water and made acidic with concentrated hydrochloric acid. The organic material was extracted into ethyl acetate. The organic layers were dried with anhydrous sodium sulphate, filtered, and concentrated in vacuo to yield quinoxaline-2-carboxylic acid as a white solid.

Compound 51 was prepared according to the procedure described for example 11 using quinoxaline-2-carboxylic acid (15.4 mg, 88.7 μmol). A white solid was obtained (25.2 mg, 66%). $^1$H NMR (ppm, CDCl$_3$): δ 9.66 (s, 1H), 8.30-7.26 (m, 10H), 5.62 (br s, 2H), 3.94 (d, J=6.3 Hz, 2H), 2.43 (s, 3H), 1.78 (s, 6H). LCMS (+esi): 453.1 (M+H$^+$), RT=5.75 min.

Example 52

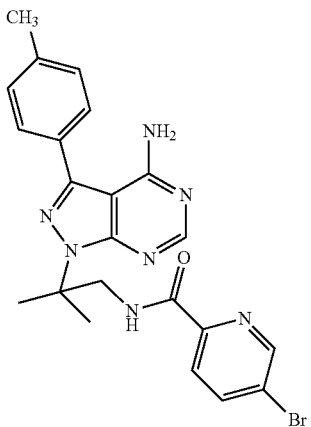 [SMILES: Cc1ccc(-c2nn(C(C)(C)CNC(=O)c3ccc(Br)cn3)c3ncnc(N)c23)cc1]

Compound 52 was prepared according to the procedure described for example 11 using 5-bromopicolinic acid (17.9 mg, 88.7 μmol). A white solid was obtained (0.3 mg, 0.7%). LCMS (+esi): 482.0 (M+H$^+$), RT=7.08 min.

Example 53

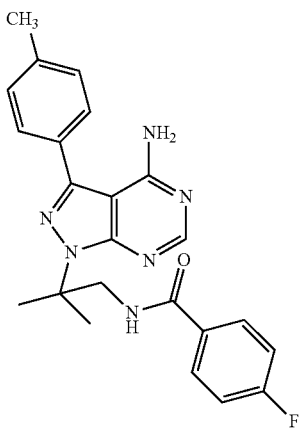 [SMILES: Cc1ccc(-c2nn(C(C)(C)CNC(=O)c3ccc(F)cc3)c3ncnc(N)c23)cc1]

Compound 53 was prepared according to the procedure described for example 11 using 4-fluorobenzoic acid (12.4 mg, 88.7 μmol). A white solid was obtained (28.7 mg, 81%). $^1$H NMR (ppm, CDCl$_3$): δ 8.35 (s, 1H), 8.18-7.05 (m, 9H), 5.90 (br s, 2H), 4.11 (d, J=6.2 Hz, 2H), 2.45 (s, 3H), 1.84 (s, 6H). LCMS (+esi): 419.1 (M+H$^+$), RT=7.64 min.

Example 54

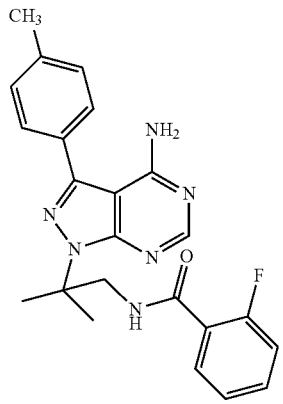 [SMILES: Cc1ccc(-c2nn(C(C)(C)CNC(=O)c3ccccc3F)c3ncnc(N)c23)cc1]

Compound 54 was prepared according to the procedure described for example 11 using 2-fluorobenzoic acid (12.4 mg, 88.7 μmol). A white solid was obtained (14.8 mg, 42%). $^1$H NMR (ppm, CDCl$_3$): δ 8.33 (s, 1H), 7.59-7.03 (m, 9H), 5.29 (br s, 2H), 4.11 (d, J=7.2 Hz, 2H), 2.44 (s, 3H), 1.82 (s, 6H). LCMS (+esi): 419.1 (M+H$^+$), RT=7.70 min.

Example 55

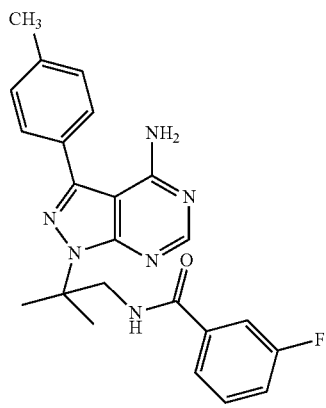 [SMILES: Cc1ccc(-c2nn(C(C)(C)CNC(=O)c3cccc(F)c3)c3ncnc(N)c23)cc1]

Compound 55 was prepared according to the procedure described for example 11 using 3-fluorobenzoic acid (12.4 mg, 88.7 μmol). A white solid was obtained (22.8 mg, 65%). $^1$H NMR (ppm, CDCl$_3$): δ 8.37 (s, 1H), 7.60-7.15 (m, 8H), 5.29 (br s, 2H), 4.12 (d, J=6.2 Hz, 2H), 2.45 (s, 3H), 1.85 (s, 6H). LCMS (+esi): 419.1 (M+H⁺), RT=7.63 min.

Example 56

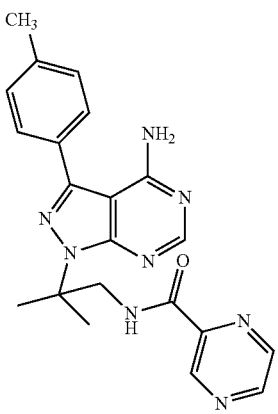 [SMILES: Cc1ccc(-c2nn(C(C)(C)CNC(=O)c3cnccn3)c3ncnc(N)c23)cc1]

Compound 56 was prepared according to the procedure described for example 11 using pyrazine-2-carboxylic acid (12.2 mg, 88.7 µmol). A beige solid was obtained (2.8 mg, 8%). LCMS (+esi): 403.1 (M+H⁺), RT=7.16 min.

Example 57

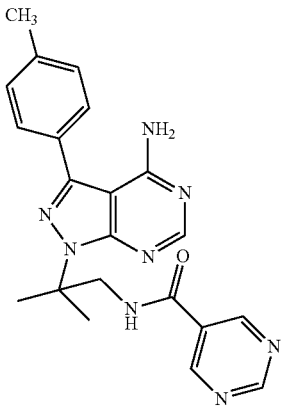 [SMILES: Cc1ccc(-c2nn(C(C)(C)CNC(=O)c3cncnc3)c3ncnc(N)c23)cc1]

Compound 57 was prepared according to the procedure described for example 11 using pyrimidine-2-carboxylic acid (12.2 mg, 88.7 µmol). A beige solid was obtained (12.5 mg, 37%). $^1$H NMR (ppm, CDCl$_3$): δ 9.31 (s, 1H), 9.17 (s, 2H), 8.38 (s, 1H), 7.37 (s, 4H), 5.66 (s, 1H), 5.29 (s, 2H), 2.45 (s, 3H), 2.43 (s, 3H), 1.73 (s, 6H). LCMS (+esi): 403.1 (M+H⁺), RT=6.76 min.

Example 58

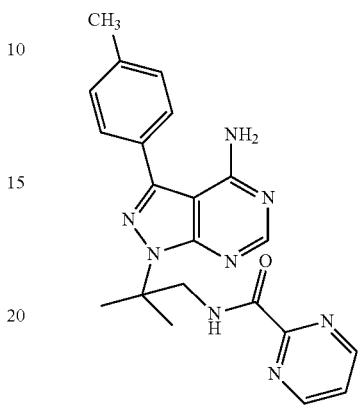

Saturated sodium hydrogen carbonate (10 mL) was added to compound 1E (106 mg, 0.29 mmol) in dichloromethane (10 mL) and left to stir at room temperature for 5 min. The organic material was extracted into dichloromethane (3×10 mL), dried with anhydrous potassium carbonate, and concentrated in vacuo. This was combined with pyrimidine-2-carboxylic acid (45 mg, 0.38 mmol), HBTU (164 mg, 0.43 mmol) and DIPEA (77.8 µL, 0.45 mmol) in DMF (6 mL) and placed in the orbital shaker overnight. The resulting solution was diluted with dichloromethane and washed with a saturated aqueous solution of sodium hydrogen carbonate and water. The organic layer was dried with anhydrous magnesium sulphate, filtered, and concentrated in vacuo to yield a yellow oil. This oil was purified using HPLC to yield compound 58 as a yellow solid (3.7 mg, 3.2%). LCMS (+esi): 403.1 (M+H⁺), RT=6.80 min.

Example 59

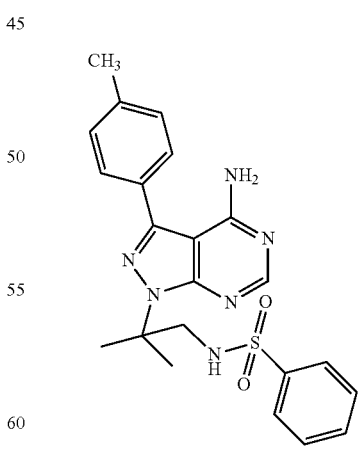

To a stirring solution of 1E (58.4 mg, 0.16 mmol) in dichloromethane (6 mL) at 0° C., triethylamine (64.5 µL, 0.46 mmol) was added. A solution of benzenesulfonyl chloride (27.4 mg, 0.15 mmol) in dichloromethane (2 mL) was then added dropwise. After 20 min at 0° C., the reaction mixture was stirred at room temperature for 24 h. The solution was then hydrolysed with saturated ammonium chloride, and extracted with dichloromethane. The combined organic layers were washed with water, dried with anhydrous magnesium sulfate, and concentrated in vacuo to yield compound 59 as a white powder (46.7 mg, 69%). LCMS (+esi): 437.1 (M+H$^+$), RT=7.57 min.

Example 60

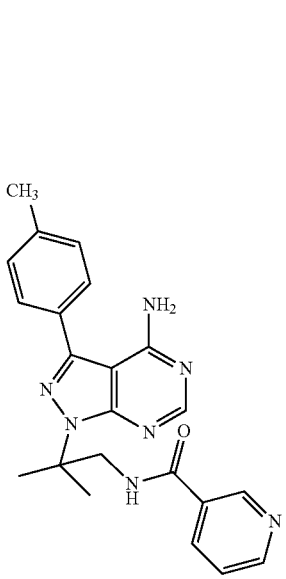 [SMILES: Cc1ccc(-c2nn(C(C)(C)CNC(=O)c3cccnc3)c3ncnc(N)c23)cc1]

Compound 60 was prepared according to the procedure described for example 11 using nicotinic acid (10.9 mg, 88.7 µmol). A beige solid was obtained (26.8 mg, 79%). LCMS (+esi): 402.1 (M+H$^+$), RT=7.04 min.

Example 61

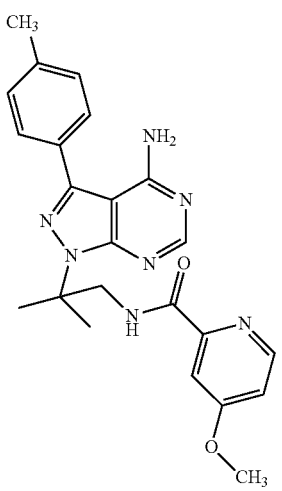 [SMILES: COc1ccnc(C(=O)NCC(C)(C)n2nc(-c3ccc(C)cc3)c3c(N)ncnc32)c1]

Compound 61 was prepared according to the procedure described for example 11 using 4-methoxypicolinic acid (13.7 mg, 88.7 µmol). A cream solid was obtained (14.6 mg, 40%). LCMS (+esi): 432.3 (M+H$^+$), RT=8.80 min.

Example 62

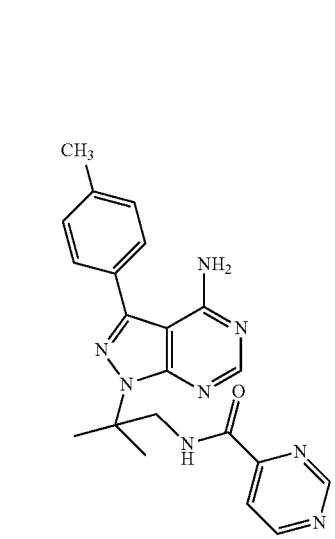 [SMILES: Cc1ccc(-c2nn(C(C)(C)CNC(=O)c3ccncn3)c3ncnc(N)c23)cc1]

Compound 62 was prepared according to the procedure described for example 11 using pyrimidine-4-carboxylic acid (10.6 mg, 88.7 µmol). A yellow solid was obtained (5.8 mg, 17%). LCMS (+esi): 403.3 (M+H$^+$), RT=7.93 min.

Example 63

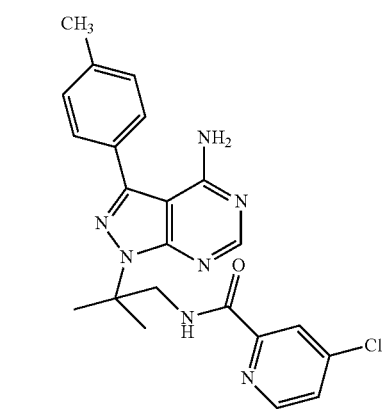 [SMILES: Cc1ccc(-c2nn(C(C)(C)CNC(=O)c3cc(Cl)ccn3)c3ncnc(N)c23)cc1]

Compound 63 was prepared according to the procedure described for example 11 using 4-chloropicolinic acid (12.7 mg, 88.7 μmol). A white solid was obtained (7.8 mg, 21%). LCMS (+esi): 436.3 (M+H⁺), RT=9.38 min.

Example 64

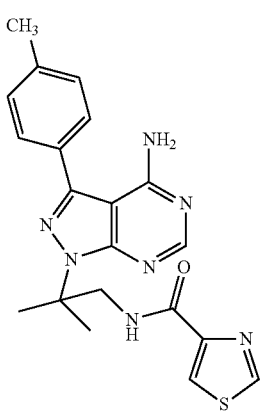 [SMILES: Cc1ccc(-c2nn(C(C)(C)CNC(=O)c3cscn3)c3ncnc(N)c23)cc1]

Compound 64 was prepared according to the procedure described for example 11 using thiazole-4-carboxylic acid (11.5 mg, 88.7 μmol). A white solid was obtained (4.8 mg, 14%). LCMS (+esi): =408.1 (M+H⁺), RT=8.05 min.

Example 65

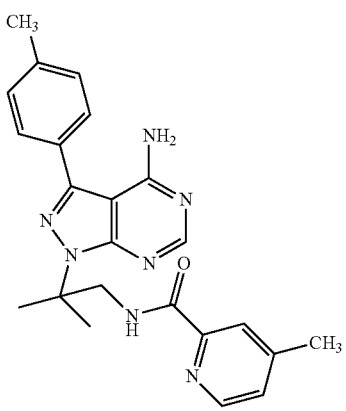 [SMILES: Cc1ccc(-c2nn(C(C)(C)CNC(=O)c3cc(C)ccn3)c3ncnc(N)c23)cc1]

Compound 65 was prepared according to the procedure described for example 11 using 4-methylpicolinic acid (11.5 mg, 88.7 μmol). A brown solid was obtained (17.2 mg, 49%). LCMS (+esi): 416.3 (M+H⁺), RT=8.84 min.

Example 66

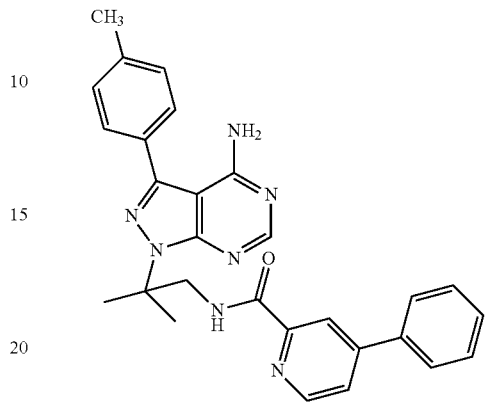

Compound 66 was prepared according to the procedure described for example 11 using 4-phenylpicolinic acid (17.7 mg, 88.7 μmol). A white solid was obtained (9.6 mg, 24%). LCMS (+esi): 478.3 (M+H⁺), RT=9.91 min.

Example 67

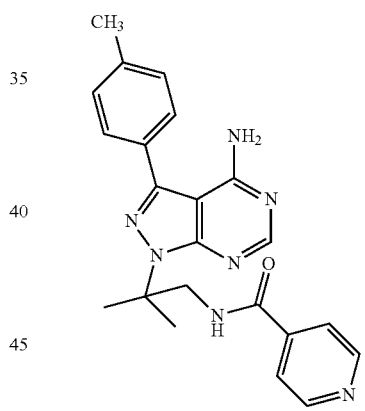

Compound 67 was prepared according to the procedure described for example 11 using isonicotinic acid (10.4 mg, 88.7 μmol). A white solid was obtained (4.9 mg, 14%). LCMS (+esi): 402.1 (M+H⁺), RT=6.70 min.

Example 68

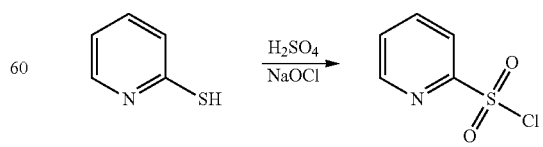

68A: A solution of 2-Mercaptopyridine (100 mg, 0.9 mmol) in 2.5 mL of concentrated sulfuric acid cooled at 0° C. was treated with 5.6 mL of 12.5% sodium hydrochloric solution added dropwise. The mixture was stirred at room temperature for 30 minutes, then poured on ice and water, extracted three times with dichloromethane, dried over magnesium sulfate and concentrated. Compound 68A was obtained as a colourless oil (110 mg, 70% yield). $^1$H NMR (ppm, CDCl$_3$): δ 7.69 (t, J=5.9 Hz, 1H), 8.09 (m, 2H), 8.80 (d, J=3.9 Hz, 1H).

organic layers were dried over sodium sulfate and concentrated in vacuo. Compound 69A was obtained as a white crystalline solid (210 mg, 96% yield). $^1$H NMR (ppm, CDCl$_3$): δ 4.01 (s, 3H), 7.50 (dd, J=2.0 Hz and 5.3 Hz, 1H), 8.13 (d, J=2.1 Hz, 1H), 8.67 (d, J=5.3 Hz, 1H). LCMS (+esi): 171.9 (M+H$^+$).

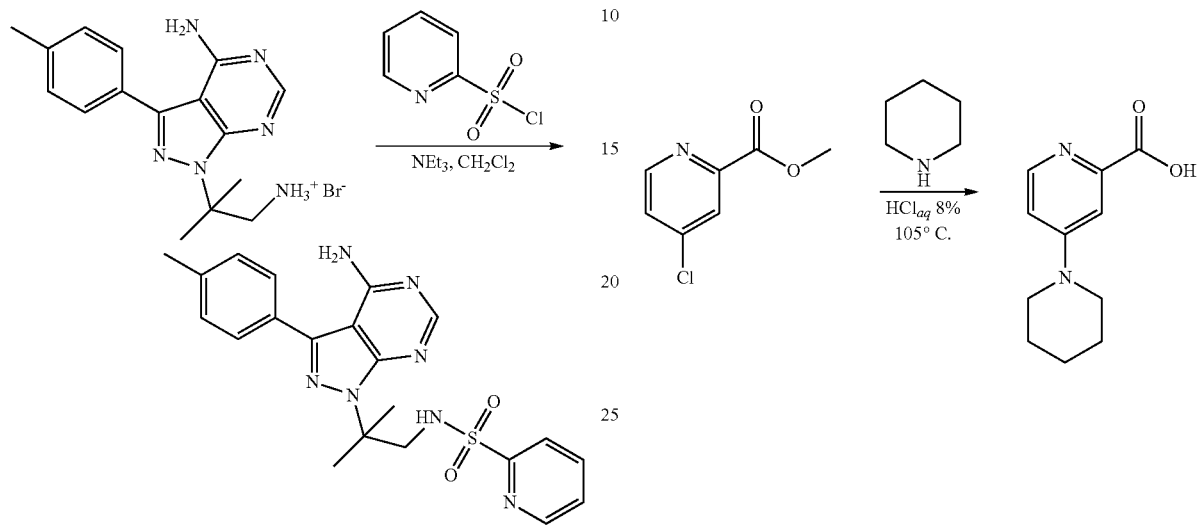

68B: A solution of compound 1E (59 mg, 0.16 mmol) in 3 mL of dichloromethane was treated with triethylamine (65 μL, 0.47 mmol). This solution was stirred for 6 hours. 68A (28 mg, 0.16 mmol) in 3 mL of dichloromethane was then added dropwise at 0° C. The mixture was stirred 20 minutes at 0° C. and 24 hours at room temperature. After 24 hours, the solution was treated with a saturated solution of ammonium chloride and extracted 3 times with dichloromethane. The combined organic layers were dried over magnesium sulfate and concentrated. Compound 68B was obtained as white crystal (53 mg, 78% yield). $^1$H NMR (ppm, CDCl$_3$): δ 1.78 (s, 6H), 2.42 (s, 3H), 3.82 (s, 2H), 5.81 (br s, 2H), 7.26-7.29 (m, 2H), 7.46-7.48 (m, 3H), 7.86 (td, J=1.7 and 7.7 Hz, 1H), 7.97 (dt, J=7.8 and 1.1 Hz, 1H), 8.11 (s, 1H), 8.64 (d, J=3.9 Hz, 1H). LCMS (+esi): 438.1 (M+H$^+$). Purity: 94.2%.

Example 69

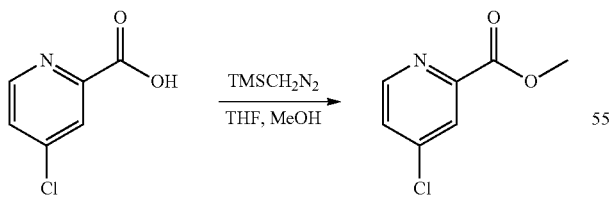

69A: 4-Chloropicolinic acid (200 mg, 1.27 mmol) was dissolved in a mixture of 2 mL of THF and 600 μL of methanol and cooled to 0° C. Trimethylsilyldiazomethane (552 μL, 1.1 mmol) were added dropwise (strong gas evolution). The solution was stirred for 3 hours at 0° C., then overnight at room temperature. After that time, a few drops of acetic acid were added, followed by water. The aqueous solution was extracted three times with ethyl acetate. The combined 69B: compound 69A (100 mg, 0.58 mmol) and piperidine (171 μL, 1.7 mmol) were heated at 110° C. overnight. 776 μL of an 8% aqueous hydrochloric acid solution (1.7 mmol) were then added and the brown solution was stirred at 110° C. for 2 hours. The solution was then cooled at 0° C. and concentrated in vacuo. The residue was dissolved in boiling water and heated at 110° C. for 5 minutes then kept at −20° C. for 1 hour and at 4° C. for 72 hours. Filtration afforded compound 69B as brown crystals (18 mg, 9% yield). $^1$H NMR (ppm, MeOD): δ 1.78 (s, 6H), 3.77 (s, 4H), 7.21 (dd, J=3.1 and 7.4 Hz, 1H), 7.67 (d, J=3.1 Hz, 1H), 8.07 (d, J=7.4 Hz, 1H). LCMS (+esi): 207.1 (M+H$^+$).

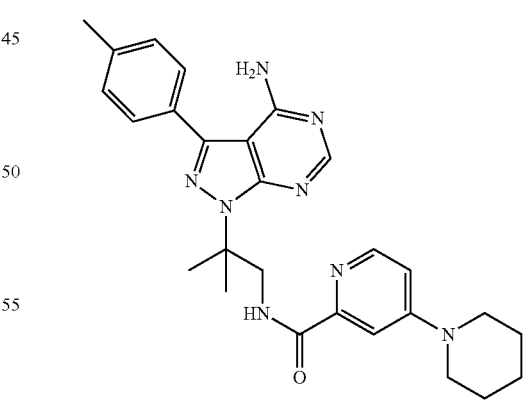

69C: Compound 69C was prepared according to the procedure described for example 11 using acid 69B (31.4 mg, 0.08 mmol). Compound 69C was obtained as a white solid (24 mg, 71% yield). $^1$H NMR (ppm, CDCl$_3$): δ 1.65 (s, 6H), 1.85 (s, 6H), 2.44 (s, 3H), 3.40 (s, 4H), 4.18 (d, J=6.0 Hz, 2H), 5.57 (br s, 2H), 6.67 (dd, J=2.8 and 5.9 Hz, 1H), 7.35 (d, J=7.8 Hz, 2H), 7.61 (d, J=2.7 Hz, 1H), 7.71 (d, J=8.1 Hz, 2H), 8.14

(d, J=5.9 Hz, 1H), 8.36 (s, 1H), 9.21 (t, J=6.3 Hz, 1H). LCMS (+esi): 485.2 (M+H⁺). Purity: 98.8%.

Example 70

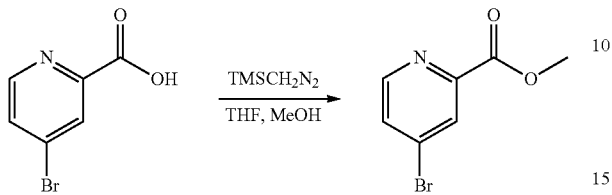

70A: 4-Bromopicolinic acid (127.5 mg, 0.63 mmol) was dissolved in a mixture of 1 mL of THF and 300 µL of methanol and cooled at 0° C. Trimethylsilyldiazomethane (276 µL, 1.87 mmol) was added dropwise at 0° C. (strong gas evolution). The solution was stirred for 2 hours at 0° C., then over night at room temperature. A few drop of acetic acid were then added followed by water. The aqueous solution was extracted three times with ethyl acetate. The combined organic layers were dried over sodium sulfate and concentrated in vacuo. Compound 70A was obtained as a yellow oil (71 mg, 60% yield). $^1$H NMR (ppm, CDCl$_3$): δ 3.98 (s, 3H), 7.64 (dd, J=1.9 and 5.2 Hz, 1H), 8.27 (d, J=1.9 Hz, 1H), 8.54 (d, J=5.2 Hz, 1H).

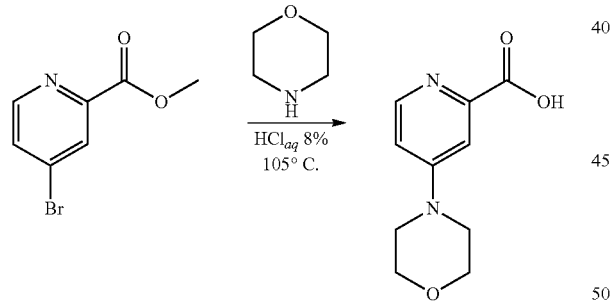

70B: compound 70A (120 mg, 0.56 mmol) was dissolved in morpholine (146 µL, 1.68 mmol) and the red solution was stirred at 110° C. overnight. 381.6 µL of an 8% aqueous hydrochloric acid solution (1.68 mmol) were added and this solution was stirred at 110° C. for 7 hours. The dark solution was concentrated in vacuo and the brown oil was crystallized in water. Compound 70B was obtained as brown crystals (35.2 mg, 30% yield). $^1$H NMR (ppm, MeOD): δ 3.86-3.76 (m, 8H), 7.28 (dd, J=3.1 and 7.4 Hz, 1H), 7.72 (d, J=3.0 Hz, 1H), 8.18 (d, J=7.4 Hz, 1H). LCMS (+esi): 209.1 (M+H⁺).

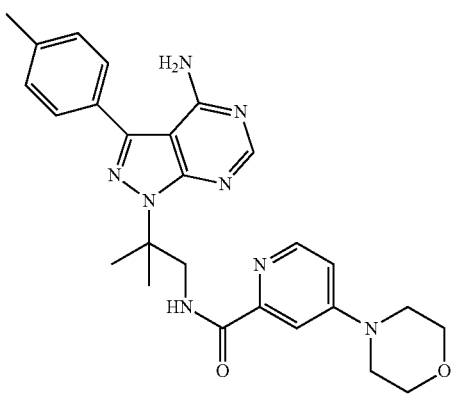 [SMILES: Cc1ccc(-c2nn(C(C)(C)CNC(=O)c3cc(N4CCOCC4)ccn3)c3ncnc(N)c23)cc1]

70C: compound 70C was prepared according to the procedure described for example 11 using acid 70B (35 mg, 0.17 mmol). A colourless oil was obtained (22 mg, 30% yield). $^1$H NMR (ppm, CDCl$_3$): δ 1.85 (s, 6H), 2.45 (s, 3H), 3.36 (t, J=5.0 Hz, 4H), 3.83 (t, J=5.0 Hz, 4H), 4.18 (d, J=6.6 Hz, 2H), 6.64 (dd, J=2.7 and 6.1 Hz, 1H), 6.70 (br m, 2H), 7.36 (d, J=7.9 Hz, 2H), 7.64 (d, J=2.5 Hz, 1H), 7.71 (d, J=7.9 Hz, 2H), 8.22 (d, J=6.0 Hz, 1H), 8.38 (s, 1H), 9.23 (t, J=6.4 Hz, 1H). LCMS (+esi): 487.2 (M+H⁺). Purity: 92%.

Example 71

Compound 1E (50 mg, 0.14 mmol) was treated with a saturated aqueous solution of NaHCO$_3$ solution and dichloromethane. The two layers were stirred at room temperature for 1 hour. The aqueous layer was then extracted 3 times with dichloromethane. The combined organic layers are dried over K$_2$CO$_3$ and concentrated in vacuo to yield a white solid. To the neutral from of 1E were added methylpicolinic acid (19.8 mg, 0.15 mmol), then 1-ethyl-3-(3-dimethylaminopropyl) carbodiimide (34.4 mg, 0.18 mmol) and 4-dimethylaminopyridine (10 mg, 0.08 mmol). 2 mL of dimethylformamide were then added and the colourless solution was stirred for 18 hours. A further 10 mg of 4-dimethylaminopyridine (0.08 mmol) was added and the solution was stirred overnight. Dichloromethane was added and the yellow mixture was extracted 3 times with HCl 4M. The combined aqueous layers were basified with a saturated Na$_2$CO$_3$ aqueous solution, and a white precipitate appears. Filtration and rinsing with water afforded compound 71 as a white solid (20.2 mg, 37% yield). $^1$H NMR (ppm, CDCl$_3$): δ 1.86 (s, 6H), 2.44 (s, 3H), 2.73 (s, 3H), 4.16 (d, J=6.6 Hz, 2H), 5.53 (br s, 2H), 7.27 (dd, J=4.6 and 7.8 Hz, 1H), 7.35 (d, J=7.9 Hz, 2H), 7.56 (d, J=7.0 Hz, 1H), 7.67 (d, J=8.0 Hz, 2H), 8.36 (s, 1H), 8.37 (s, 1H), 9.19 (t, J=6.5 Hz, 1H). LCMS (+esi): 438.2 (M+Na⁺). Purity: 98.6%.

8.00 (d, J=7.7 Hz, 1H), 8.37 (s, 1H), 9.31 (br s, 1H). LCMS (m/z): 416.1 (M+H⁺). Purity: 94.1%.

Example 72

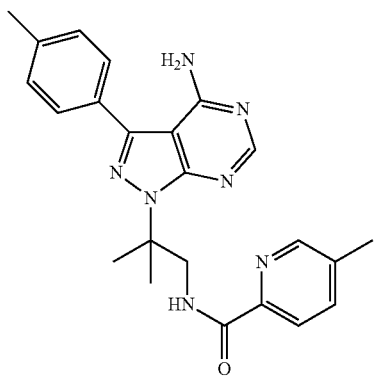

Compound 72 was prepared according to the procedure described for example 71 using 5-methylpicolinic acid (20 mg, 0.15 mmol). A white solid is obtained (28.2 mg, 51% yield). ¹H NMR (ppm, CDCl₃): δ 1.85 (s, 6H), 2.38 (s, 3H), 2.45 (s, 3H), 4.19 (d, J=6.6 Hz, 2H), 5.59 (br s, 2H), 7.37 (d, J=7.8 Hz, 2H), 7.61 (d, J=7.9 Hz, 1H), 7.70 (d, J=8.0 Hz, 2H), 8.09 (d, J=8.0 Hz, 1H), 8.36 (s, 1H), 8.37 (s, 1H), 9.19 (t, J=6.0 Hz, 1H). LCMS (+esi): 438.2 (M+Na⁺). Purity: 98.5%.

Example 73

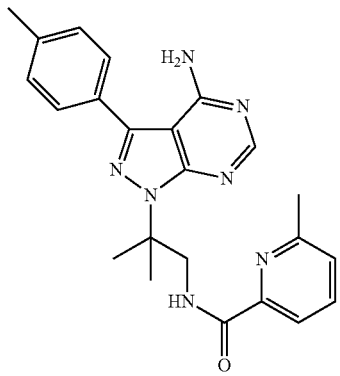 [SMILES: Cc1ccc(-c2nn(C(C)(C)CNC(=O)c3cccc(C)n3)c3ncnc(N)c23)cc1]

Compound 73 was prepared according to the procedure described for example 72 using 6-methylpicolinic acid (20 mg, 0.15 mmol). A white solid is obtained (24.1 mg, 44% yield). ¹H NMR (ppm, CDCl₃): δ 1.85 (s, 6H), 2.45 (s, 3H), 2.50 (s, 3H), 4.18 (d, J=6.7 Hz, 2H), 5.61 (br s, 2H), 7.23 (d, J=6.7 Hz, 1H), 7.35 (d, J=7.9 Hz, 2H), 7.67-7.71 (m, 3H),

Example 74

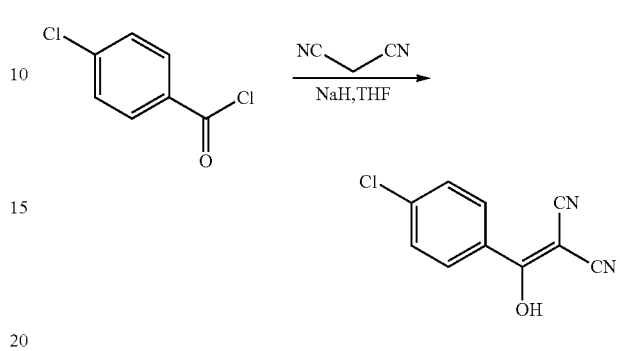

74A: NaH (725 mg, 30 mmol) was added to a suspension of malononitrile (1 g, 15.1 mmol) in 15 mL of THF at 0° C. After the addition was complete, 4-chlorobenzoyl chloride (1 g, 5.75 mmol) was added dropwise at 0° C. The reaction mixture was stirred at room temperature for 30 mins. HCl 1N was added and the acid aqueous layer was extracted three times with ethyl acetate. The combine organic layers were washed with brine, dried over sodium sulfate, filtered and concentrated in vacuo to obtain compound 74A as pale yellow solid (1.12 g, 95%). ¹H NMR (ppm, MeOD): δ 7.69 (d, J=8.7 Hz, 2H), 7.55 (d, J=8.9 Hz, 2H), 4.12 (s, 3H).

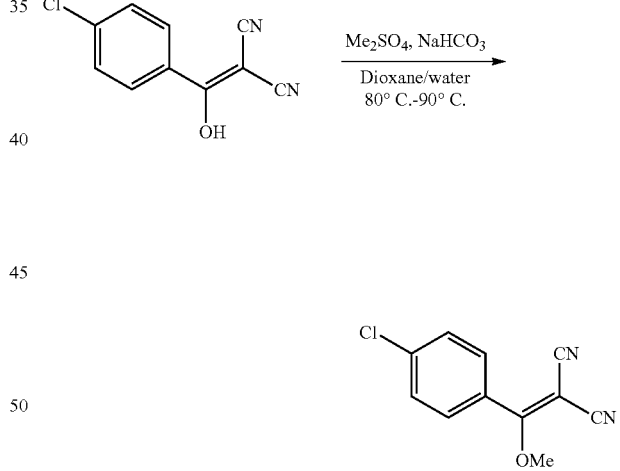

74B: Compound 74A (1.92 g, 9.4 mmol) was dissolved in a mixture of dioxane (15 mL) and water (2 mL) in a two-neck flask. Sodium bicarbonate (6.2 g, 74.3 mmol) was added to the mixture followed by dimethylsulfate (8.3 g, 65.9 mmol). The reaction was stirred at 84° C. for 2 hr 30 mins. Water was added and the aqueous layer was extracted with tert-Butylmethyl ether followed by diethyl ether. The combine organic phases were dried over anhydrous sodium sulphate, filtered and concentrated in vacuo. The resulting mixture was recrystallised with methanol to yield compound 74B as white solid (1.3 g, 65%). ¹H NMR (ppm, MeOD): δ 7.56 (d, J=8.6 Hz, 2H), 7.47 (d, J=8.7 Hz, 2H), 3.98 (s, 3H). LCMS (+esi): 219 (M+H⁺).

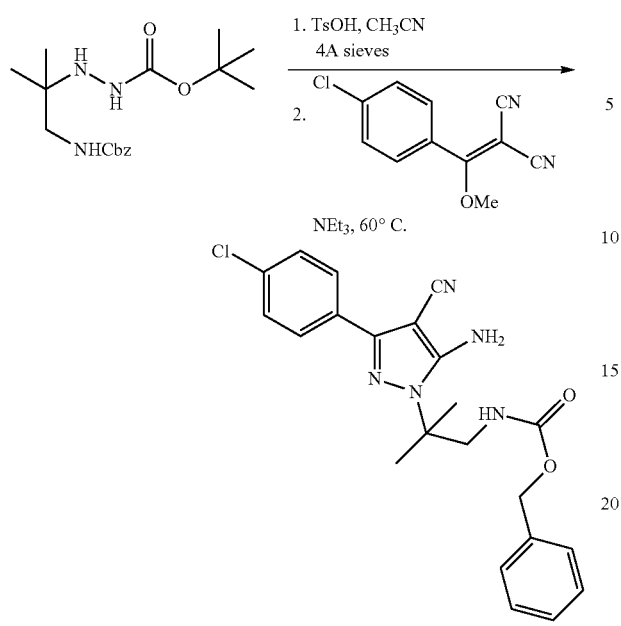

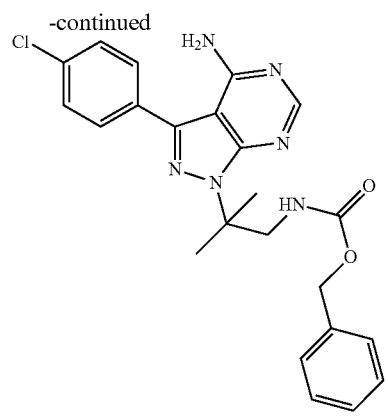

74C: Compound 1B (1 g, 4.2 mmol) was dissolved in 4.3 mL of dry acetonitrile. Tosic acid (4 g, 21.1 mmol) was dissolved in 29 mL of dry acetonitrile. Molecular sieves were added to both solutions and stood for 30 minutes. The solution of Tosic acid was then added to the solution of 1B and the reaction was stirred at room temperature for 2 hours. The reaction was filtered and the solid washed with acetonitrile and dichloromethane. The filtrate was concentrated in vacuo to afford a thick and colourless oil. The colourless oil was dissolved in 5 mL of ethanol. Triethylamine (696 mg, 6.9 mmol) and compound 74A (300 mg, 1.4 mmol) were successively added. The reaction was then stirred at 60° C. for 3 hours. After cooling down, the reaction was concentrated. Water and ethyl acetate were then added and the aqueous phase was extracted three times with ethyl acetate. The combine organic layers were dried over sodium sulphate and concentrated. The oily residue obtained was purified by flash chromatography on SiO$_2$ using 100% DCM then MeOH/DCM 1:99 to afford compound 74C as a semi solid (387 mg, 67%). $^1$H NMR (ppm, CDCl$_3$): δ 7.83 (d, J=8.8 Hz, 2H), 7.37 (d, J=2.6 Hz, 2H), 7.33 (m, 5H), 5.52 (t, J=6.3 Hz, 1H), 5.10 (s, 2H), 4.48 (s, 2H), 3.78 (d, J=6.7 Hz, 2H), 1.60 (s, 6H). LCMS (+esi): 423 (M+H$^+$).

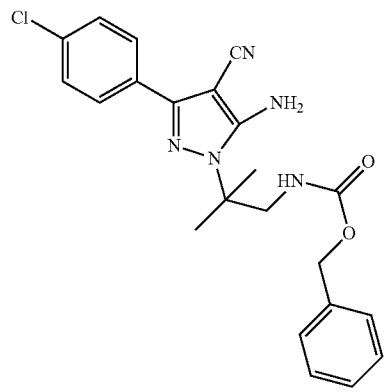

74D: Compound 74C (372 mg, 0.88 mmol) and formamidine acetate (366 mg, 3.52 mmol) were reacted at 150° C. in 1.5 mL of 2-methoxyethanol. 3 more portions of formamidine acetate were added to the reaction mixture within 1 hour interval. The reaction mixture was refluxed at 150° C. overnight. The reaction mixture was then cooled to room temperature; water and ethyl acetate were added. The aqueous phase was extracted three times with ethyl acetate. The combine organic phases were washed two times with water and brine, dried over anhydrous sodium sulphate, filtered and concentrated in vacuo. The yellow oil obtained was purified by flash chromatography eluted with 30%-50% EtOAc/Petroleum spirit to yield compound 74D as clear oil, which solidified overnight (241 mg, 61%). $^1$H NMR (ppm, CDCl$_3$): δ 8.34 (s, 1H), 7.60 (d, J=8.7 Hz, 2H), 7.52 (d, J=8.6 Hz, 2H), 7.34 (m, 5H), 5.94 (t, J=6.2 Hz, 1H), 5.44 (s, 2H), 5.09 (s, 2H), 3.96 (d, J=6.6 Hz, 2H), 1.78 (s, 6H). LCMS (+esi): 452 (M+H$^+$).

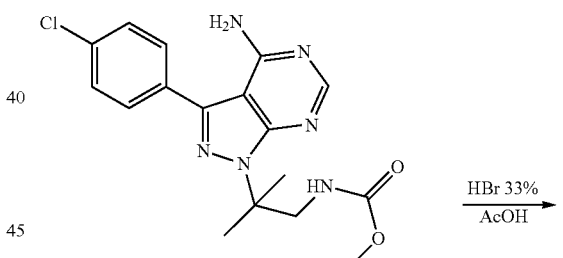

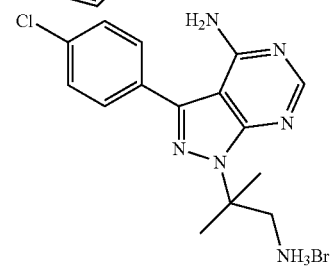

74E: Compound 74D (240 mg, 0.53 mmol) was treated with 2.7 mL of a 33% solution of HBr in glacial acetic acid. The reaction was stirred at room temperature for one hour. Dry ether was then added to the reaction mixture leading to yellow precipitate. It was collected by filtration and rinsed thoroughly with ether and dried for a day to afford compound 74E as white solid (140 mg, 84%). $^1$H NMR (ppm, DMSO-$d_6$): δ 8.32 (s, 1H), 7.94 (s, 2H), 7.69 (d, J=8.6 Hz, 2H), 7.61 (d, J=8.4 Hz, 2H), 3.65 (d, J=5.5 Hz, 2H), 1.76 (s, 6H). LCMS (+esi): 317 (M+H$^+$).

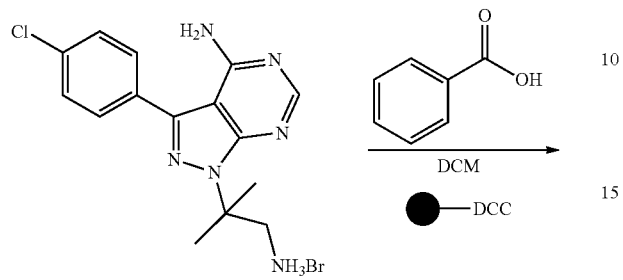

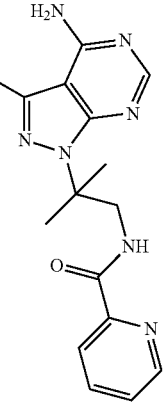

74F: Compound 74F was obtained following the procedure used to prepare compound 11 using compound 74E (50 mg, 0.16 mmol) and benzoic acid (19 mg, 0.16 mmol). Compound 74F was obtained as white solid (40 mg, 61%). $^1$H NMR (ppm, CDCl$_3$): δ 8.41 (s, 1H), 8.36 (t, J=6.1 Hz, 1H), 7.81 (d, J=8.6 Hz, 2H), 7.63 (d, J=8.3 Hz, 2H), 7.46 (m, 5H), 5.61 (s, 2H), 5.29 (s, 1H), 4.15 (d, J=5.5 Hz, 2H), 1.85 (s, 6H). LCMS (+esi): 421 (M+H$^+$).

Example 75

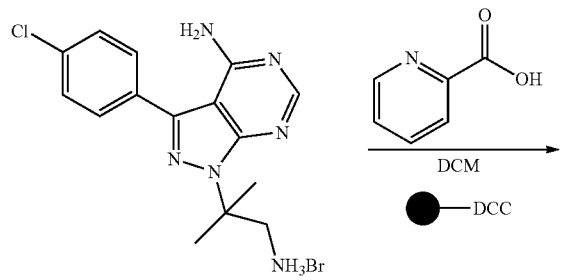

Compound 75 was obtained following the procedure used to prepare compound 11 using compound 74E (50 mg, 0.16 mmol) and picolinic acid (19 mg, 0.16 mmol). Compound 75 was obtained as white solid (32 mg, 48%). $^1$H NMR (ppm, CDCl$_3$): δ 9.20 (s, 1H), 8.2-8.53 (m, 3H), 7.29-7.86 (m, 5H), 5.54 (s, 2H), 4.2 (d, J=6.6 Hz, 2H), 1.86 (s, 6H). LCMS (+esi): 422 (M+H$^+$).

Example 76

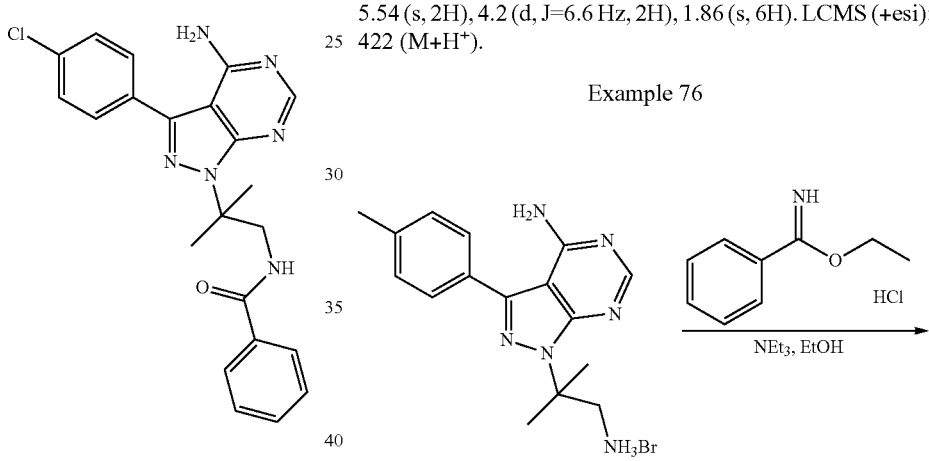

Compound 1E (73 mg, 0.19 mmol) was neutralised (suspended in CH$_2$Cl$_2$ and treated with saturated sodium bicarbonate aqueous solution, dried over potassium carbonate and concentrated). The residue dissolved in 0.7 mL of EtOH was added to a solution of ethyl benzimidate hydrochloride (36 mg, 0.19 mmol) in 0.1 mL of EtOH followed by triethylamine (60 mg, 0.58 mmol). The reaction mixture was stirred at room temperature for 16 hours. The reaction mixture was concentrated in vacuo to remove excess EtOH. It was then purified by preparative HPLC to afford compound 76 as white solid (12 mg, 16%). ¹H NMR (ppm, MeOD): δ 8.32 (s, 1H), 7.67 (s, 1H), 7.47-7.7.58 (m, 6H), 7.37 (d, J=7.8 Hz, 2H), 5.48 (s, 1H), 4.20 (s, 2H), 2.43 (s, 3H), 2.00 (s, 6H). LCMS (+esi): 400 (M+H⁺)

7.71 (s, 1H), 7.61 (d, J=7.0 Hz, 2H), 7.39 (d, J=7.2 Hz, 2H), 4.24 (s, 2H), 2.45 (s, 3H), 1.96 (s, 6H). LCMS (+esi): 401 (M+H⁺).

Example 77

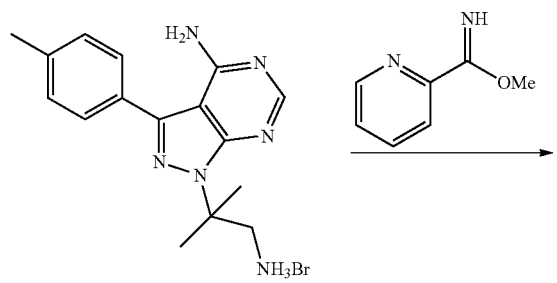

Example 78

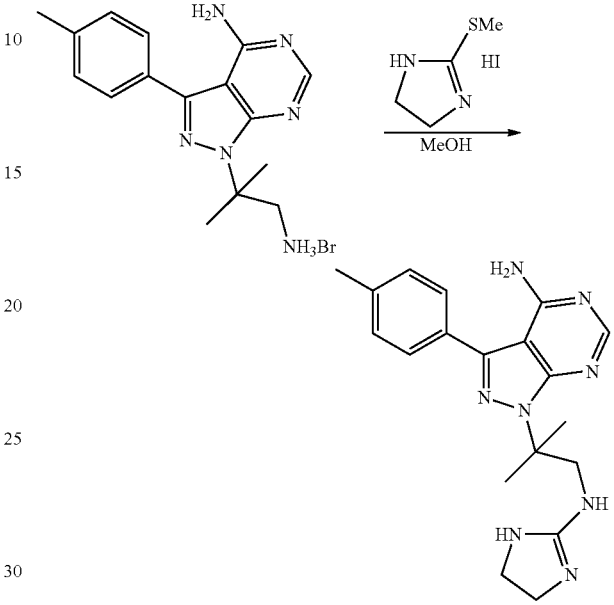

Compound 1E (22.7 mg, 0.06 mmol) was neutralised (suspended in CH₂Cl₂ and treated with saturated sodium bicarbonate aqueous solution, dried over potassium carbonate, filtered and concentrated). The residue and 4,5-dihydro-2-(methylthio)-1H-imidazole hydroiodide (30 mg, 0.12 mmol) in 0.4 mL of dry methanol were refluxed for 1 day under nitrogen. Another equivalent of 4,5-hydro-2-(methylthio)-1H-imidazole hydroiodide was added to the reaction mixture and stirred at reflux for another day. The reaction mixture was concentrated in vacuo to remove methanol. The mixture was purified using preparative HPLC to afford compound 78 as semi-white solid (5 mg, 20%). ¹H NMR (ppm, CDCl₃): δ 8.33 (s, 1H), 7.59 (d, J=7.3 Hz, 2H), 7.34 (d, J=7.7 Hz, 2H), 6.91 (s, 2H), 5.43 (t, J=3.9 Hz, 2H), 4.15 (s, 4H), 3.65 (d, J=2.3 Hz, 2H), 3.53 (s, 3H), 2.44 (s, 3H), 1.90 (s, 6H). LCMS (+esi): 364 (M+H⁺).

Example 79

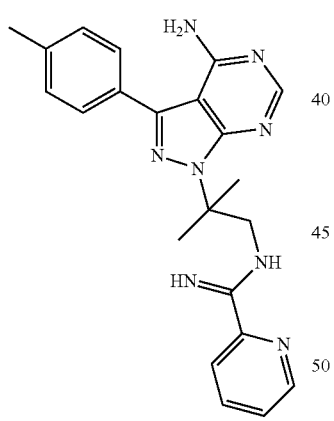

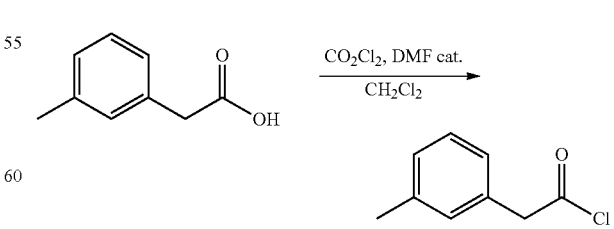

To a stirred suspension of 2-cyanopyridine (50 mg, 0.49 mmol) in 1.4 mL of dry methanol was added a 0.5 M sodium methoxide solution in methanol (0.35 mL, 0.18 mmol). The reaction mixture was stirred at room temperature for two days to allow the imidate ester to form. To this solution of imidate ester (0.1 mL, 0.08 mmol) was added compound 1E (30 mg, 0.08 mmol). The resulting mixture was stirred at room temperature until all the starting material had reacted. A white precipitate formed while stirring overnight. The reaction mixture was stopped and concentrated in vacuo to remove methanol. The mixture was purified by preparative HPLC to afford compound 77 as white solid (7.5 mg, 23%). ¹H NMR (ppm, MeOD): δ 8.75 (s, 1H), 8.24 (s, 1H), 8.07 (d, J=5.3 Hz, 2H), 79A: To a solution of 2-m-tolylacetic acid (1 g, 6.7 mmol) in 10 mL of dichloromethane were added oxalyl chloride (887 mg, 7 mmol) and one drop of DMF. The resulting solution was stirred for 1 h at room temperature. The solvent was removed in vacuo, and the resulting product was directly used in the next step without further purification.

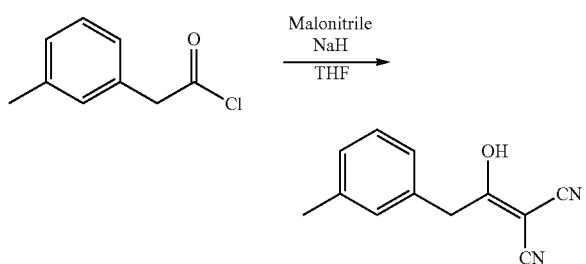

79B: malonitrile (440 mg, 6.6 mmol) in 5 mL of THF was treated with sodium hydride (320 mg, 13.3 mmol). Compound 79A in solution in THF was then added dropwise. The solution was stirred at room temperature for 1 hr. Aqueous 1N HCl solution was then added, and the mixture was extracted three times with ethyl acetate. The combined organic layers were then dried over $MgSO_4$ and concentrated. The resulting crude material was purified by column chromatography on $SiO_2$ using ethyl acetate/cyclohexane (50:50). Compound 79B was obtained as a brown oil (477 mg, 36% yield). $^1$H NMR ($CDCl_3$): δ 7.03 (m, 4H), 3.63 (s, 2H), 2.23 (s, 3H).

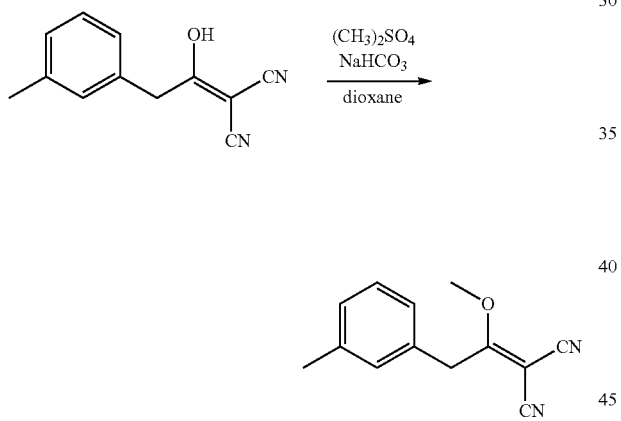

79C: To sodium hydrogen carbonate (1.62 g, 19 mmol) in 3.9 mL of 1,4-dioxane were slowly added compound 79B (477 mg, 2.4 mmol) and dimethyl sulphate (2.1 g, 17 mmol). After stirring at 80° C. for 3 h, water was added, and the mixture was extracted three times with tert-butylmethyl ether. The combined organic layers were then dried over $Na_2SO_4$ and concentrated. Purification by column chromatography on $SiO_2$ using methanol/dichloromethane (1:99) led to compound 79C as a pale yellow oil (235 mg, 46% yield). $^1$H NMR ($CDCl_3$): δ 7.27 (t, J=7.5 Hz, 1H), 7.15 (d, J=9 Hz, 1H), 7.05 (m, 2H), 3.99 (s, 3H), 3.99 (s, 2H), 2.37 (s, 3H).

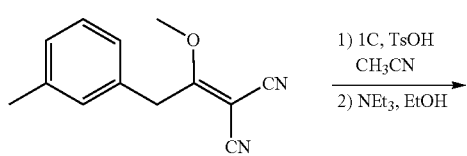

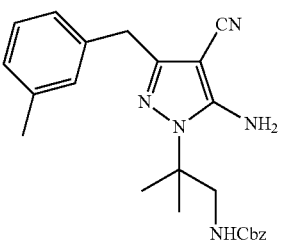

79D: the procedure used to prepare compound 1D was followed using 1C (126 mg, 0.64 mmol) and 79C (135 mg, 0.64 mmol). Purification by column chromatography on $SiO_2$ using methanol/dichloromethane (1:99) afforded compound 79D as a pale yellow oil (210 mg, 79% yield). $^1$H NMR ($CDCl_3$): δ 7.34 (m, 6H), 7.04 (m, 3H), 5.65 (br s, 1H), 5.10 (s, 2H), 4.4 (br s, 2H), 3.81 (s, 2H), 3.69 (m, 2H), 2.27 (s, 3H), 1.51 (s, 6H).

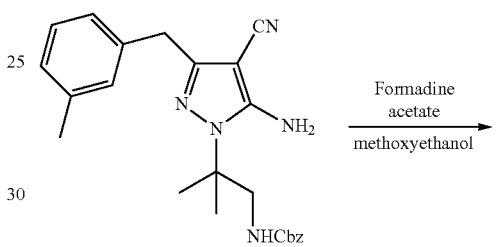

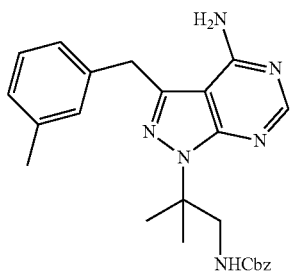

79E: compound 79D (210 mg, 0.5 mmol) and formamidine acetate (209 mg, 2 mmol) were stirred in 2.7 mL of methoxyethanol. The reaction mixture was refluxed for 4 h and 4 additional portions of formamidine acetate (209 mg each, 2 mmol) were added in the reaction mixture every hour. The reaction mixture was then cooled to room temperature and the solvent was evaporated in vacuo. The crude product was then dissolved in dichloromethane, and the brown precipitate was filtered off. The filtrate was concentrated and purified by column chromatography on $SiO_2$ using methanol/dichloromethane (2:98) to afford compound 79C (116 mg, 52% yield). $^1$H NMR ($CDCl_3$): δ 8.21 (s, 1H), 7.33 (m, 6H), 7.20 (t, J=6.0 Hz, 1H), 7.07 (d, J=6.0 Hz, 1H), 6.98 (d, J=9 Hz, 1H), 6.01 (br t, 1H), 5.09 (d, J=6.0 Hz, 2H), 5.05 (br s, 2H), 4.23 (s, 2H), 3.62 (d, J=6 Hz, 2H), 2.29 (s, 3H), 1.59 (s, 6H). LCMS (+esi): 444.9 (M+H$^+$), RT=6.46 min.

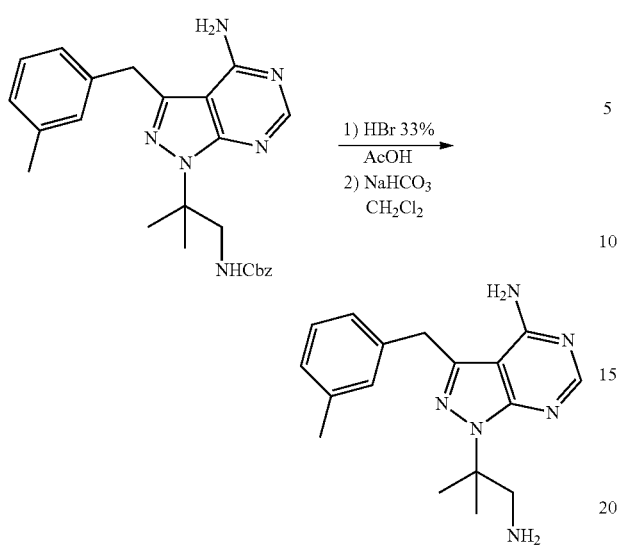

79D: Compound 79C (116 mg, 0.26 mmol) was treated with 2 mL of a 33% solution of hydrobromic acid in acetic acid. The reaction mixture was stirred at room temperature for 5 h (monitored by TLC). The solvent was then removed in vacuo and the crude product was dried in a vacuum oven. Dichloromethane was added and the precipitate was filtered off and dried in vacuo. This precipitate was then stirred in dichloromethane and saturated NaHCO$_3$ solution for 30 min for neutralization. The reaction mixture was then extracted three times with dichloromethane, dried over Na$_2$SO$_4$ and concentrated, to give compound 79D as an orange powder (28 mg, 35% yield). LCMS (+esi): 311.2 (M+H$^+$), RT=4.51 min.

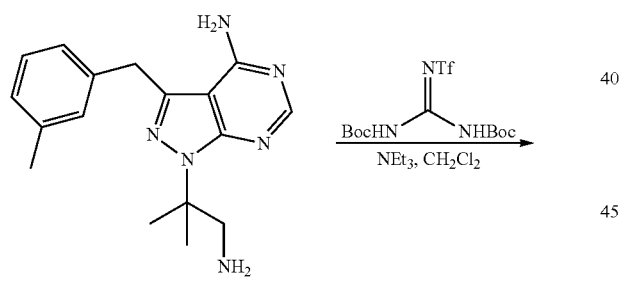

79E: Compound 79D (28 mg, 0.09 mmol), N,N'-diBoc-N''-trifluoromethanesulfonylguanidine (32 mg, 0.08 eq) and triethylamine (12 μL, 0.09 mmol) were dissolved in 0.7 mL of dry dichloromethane. The reaction mixture was stirred at room temperature overnight. Dichloromethane was then added and this organic layer was washed successively with a 0.2 M sodium bisulphate aqueous solution, saturated sodium bicarbonate aqueous solution and brine. The combined organic layers were dried over Na$_2$SO$_4$ and concentrated, to give compound 79E as yellow oil (57 mg, quantitative). LCMS (+esi): 353.1 (M-Boc$^+$), RT=5.68 min.

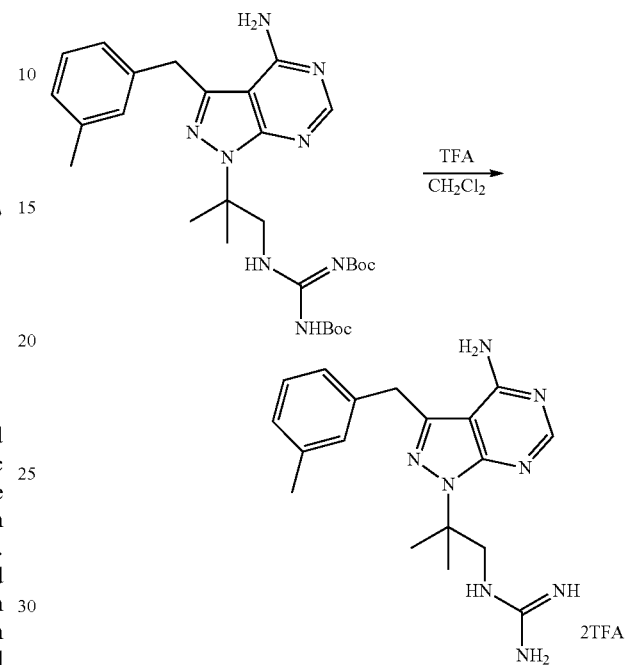

79F: Compound 79E (57 mg, 0.13 mmol) was dissolved in 1.8 mL of dry dichloromethane and cooled to 0° C. 0.7 mL of Trifluoroacetic acid was then added dropwise. The reaction mixture was allowed to warm to room temperature and stirred overnight. The solvent was removed in vacuo, and toluene was then added and evaporated to remove the remaining TFA. The brown oil that was obtained was dissolved in water and acetonitrile and placed into the freeze dryer to afford a white solid. Preparative HPLC afforded compound 79F as a white powder. NMR (CDCl$_3$): δ 8.53 (br s, 1H), 8.15 (s, 1H), 7.19 (t, J=7.7 Hz, 1H), 7.08 (s, 1H), 7.04-7.00 (m, 2H), 4.31 (s, 2H), 3.96 (s, 2H), 2.29 (s, 3H), 1.78 (s, 6H). LCMS (+esi): 353.3 (M+H$^+$), RT=4.62 min.

Example 80

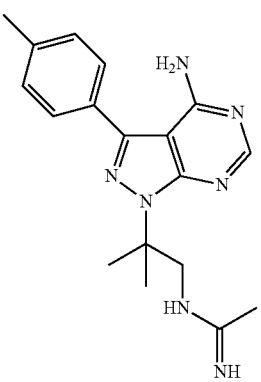 [SMILES: CC(=N)NCC(C)(C)n1nc(-c2ccc(C)cc2)c2c(N)ncnc21]

To a solution of compound 1E (10 mg, 0.03 mmol) in 1 mL of dichloromethane was added a saturated aqueous solution of NaHCO$_3$ and the mixture was stirred for 2 hours at room temperature. The reaction mixture was then extracted three times with dichloromethane, dried over anhydrous K$_2$CO$_3$ and concentrated to give the free amine. A mixture of this amine and ethylacetamidate hydrochloride (3.3 mg, 0.03 mmol) in 200 μL of methanol was stirred at room temperature for 25 h. The solution was then evaporated under reduced pressure and 1 mL of acetonitrile was added to the residue. The mixture was then alkalized with a 0.1 M aqueous solution of NaOH and extracted thrice with dichloromethane. The solution was then dried over anhydrous Na$_2$SO$_4$, filtered, concentrated in vacuo, and purified by preparative HPLC to give compound 80 as white powder (1.5 mg, 17% yield). $^1$H NMR (ppm, CDCl$_3$): δ 8.27 (s, 1H), 7.53 (d, J=7.4 Hz, 2H), 7.36 (d, J=7.6 Hz, 2H), 3.82 (s br, 2H), 2.40-2.44 (m, 6H), 1.85 (s, 6H). LCMS (+esi): 338.2 (M+H$^+$), RT=4.37 min.

Example 81

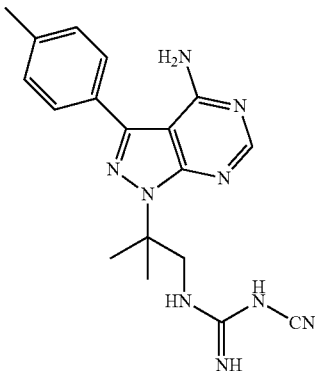 [SMILES: Cc1ccc(-c2nn(C(C)(C)CNC(=N)NC#N)c3ncnc(N)c23)cc1]

To a solution of Compound 1E (30 mg, 0.08 mmol) in 0.5 mL of 1-butanol was added sodium dicyanamide (7.1 mg, 0.08 mmol). The mixture was stirred at 140° C. overnight. The mixture was concentrated and the residue purified by preparative HPLC to give compound 81 as a white powder (12 mg, 41% yield). $^1$H NMR (ppm, CDCl$_3$): δ 8.29 (s, 1H), 7.55 (d, J=6.9 Hz, 2H), 7.36 (d, J=7.6 Hz, 2H), 3.87 (s, 2H), 2.43 (s, 3H), 1.83 (s, 6H). LCMS (+esi): 364.4 (M+H$^+$), RT=4.31 min.

Example 82

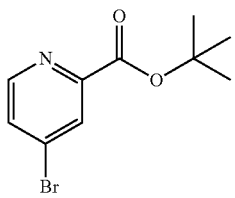

82A: To a solution of 4-Bromopicolinic acid (0.5 g, 3.2 mmol) in 5 mL of t-butanol was added pyridine (1.5 mL, 19 mmol) and cooled to 0° C. Toluene sulfonyl chloride (1.8 g, 9.5 mmol) was then added portion-wise. The reaction was stirred at 0° C. for 10 minutes and at room temperature overnight. The mixture was slowly poured into saturated sodium hydrogen carbonate and extracted three times with dichloromethane. The combined organic layers were washed with brine and concentrated in vacuo. The crude product was purified via flash chromatography on SiO$_2$ using methanol/dichloromethane (2:98). Compound 82A was obtained as a white solid (735 mg, 89%). $^1$H NMR (ppm, CDCl$_3$): δ 8.53 (d, J=4 Hz, 1H), 8.18 (s, 1H), 7.58 (d, J=4 Hz, 1H), 1.63 (s, 9H). LCMS (+esi): 259 (M+H$^+$).

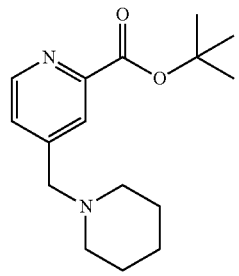 [SMILES: CC(C)(C)OC(=O)c1cc(CN2CCCCC2)ccn1]

82B: in an oven dried Schlenk tube were added palladium acetate (13 mg, 0.02 mmol), butyl di-1-adamantyl phosphine (14 mg, 0.04 mmol), potassium (piperidin-1-yl)-methyltrifluoroborate (0.08 g, 0.4 mmol), compound 82A (0.1 g, 0.4 mmol) and cesium carbonate (0.38 g, 1.2 mmol). The tube was filled with nitrogen and evacuated three times. 2 mL of anhydrous toluene were added and the mixture stirred for 5 minutes, followed by the addition of 200 μL of water. The mixture was heated up to 95° C. and left stirring for 24 hours. The reaction was concentrated in vacuo and the residue was re-dissolved in ethyl acetate and washed with water, brine and dried over sodium sulphate. The product was purified via flash chromatography on SiO$_2$ using methanol/dichloromethane (5:95). A clear oil was obtained (104 mg, 94%). $^1$H NMR (ppm, CDCl$_3$): δ 8.63 (d, J=9 Hz, 1H), 7.97 (s, 1H), 7.47 (d, J=9 Hz, 1H), 3.54 (s, 2H), 2.3-2.41 (m, 4H), 1.58-1.66 (m, 11H), 1.38-1.46 (m, 4H). LCMS (+esi): 277 (M+H$^+$).

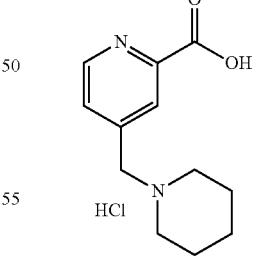

82C: Compound 82B (0.06 g, 0.22 mmol) was dissolved in methanol (1 mL) and 0.5 mL of a 2M solution of sodium hydroxide was added. The reaction was stirred at room temperature overnight. The methanol was concentrated down and the remaining aqueous layer was acidified to pH 2 with 1M aqueous hydrogen chloride. The aqueous layer was placed on freeze drier overnight. The sodium salt was used in the next reaction without further purification.

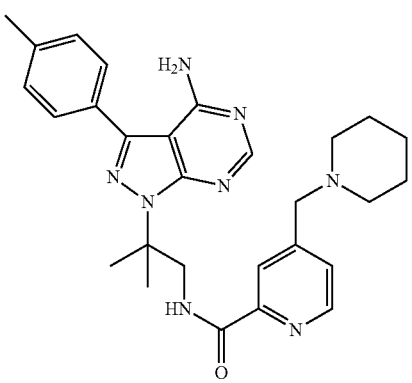 [SMILES: Cc1ccc(-c2nn(C(C)(C)CNC(=O)c3cc(CN4CCCCC4)ccn3)c3ncnc(N)c23)cc1]

82D: to compound 1E (64 mg, 0.17 mmol) dissolved in 2 mL of dichloromethane was added saturated sodium carbonate. The mixture was stirred at room temperature for 1 hour. The aqueous layer was extracted with dichloromethane. The combined organic layers were dried over $K_2CO_3$ and concentrated in vacuo. The neutralized product (50 mg, 0.17 mmol), compound 82C (40 mg 0.17 mmol), 1-ethyl-3-(3-dimethyl aminopropyl)carbodiimide (40 g, 0.22 mmol) and 4-dimethylaminopyridine (62 mg, 0.51 mmol) were dissolved in 2 mL of anhydrous dimethylformamide. The reaction was stirred for 24 hours at room temperature. After this time, water was added to the reaction. The aqueous layer was extracted three times with ethyl acetate; the combined organic layers were washed with brine, dried over sodium sulphate and concentrated. The crude mixture was purified via flash chromatography on $SiO_2$ using methanol/dichloromethane (2:98). Compound 82D was obtained as a white solid (41 mg, 49%). $^1$H NMR (ppm, $CDCl_3$): δ 9.23 (t, J=6 Hz, 1H), 8.44 (d, J=5 Hz, 1H), 8.36 (s, 1H), 8.11 (d, J=1 Hz, 1H), 7.68 (d, J=8 Hz, 2H), 7.37 (m, 1H), 7.26 (d, J=8 Hz, 2H), 5.60 (br s, 2H), 4.18 (d, J=7 Hz, 2H), 3.5 (s, 2H), 2.99 (s, 3H), 2.34-2.37 (m, 4H), 1.85 (s, 6H), 1.53-1.60 (m, 4H), 1.42-1.44 (m, 2H). LCMS (+esi): 499 (M+H$^+$).

Example 83

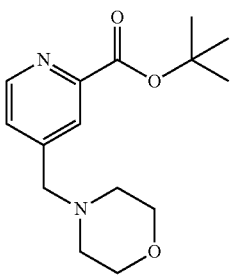 [SMILES: CC(C)(C)OC(=O)c1cc(CN2CCOCC2)ccn1]

83A: In an oven dried Schlenk tube were added palladium acetate (13 mg, 0.02 mmol), butyl di-1-adamantyl phosphine (14 mg, 0.04 mmol), potassium (morpholin-4-yl)methyltrifluoroborate (80 mg, 0.4 mmol), compound 82A (100 mg, 0.4 mmol) and cesium carbonate (380 mg, 1.2 mmol). The tube was filled with nitrogen and evacuated three times. 2 mL of anhydrous toluene were added and the mixture was stirred for 5 minutes. 200 μL of water were then added. The mixture was heated up to 95° C. and stirred for 24 hours. After this time, the reaction was concentrated in vacuo. The residue was redissolved in ethyl acetate. The organic layer was washed with water, brine and dried over sodium sulphate. The crude material was purified via flash chromatography on $SiO_2$ using methanol/dichloromethane (5:95). Compound 83A was obtained as a clear oil (95 mg, 85%). $^1$H NMR (ppm, $CDCl_3$): δ 8.62 (d, J=5 Hz, 1H), 7.97 (s, 1H), 7.42 (d, J=5 Hz, 1H), 3.68-3.71 (m, 4H), 3.53 (s, 2H), 2.42-2.45 (m, 4H), 1.59 (s, 9H). LCMS (+esi): 279 (M+H$^+$).

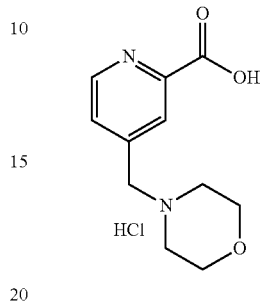

83B: compound 83B was obtained following the procedure described for the preparation of compound 82C using compound 83A (50 mg, 0.18 mmol).

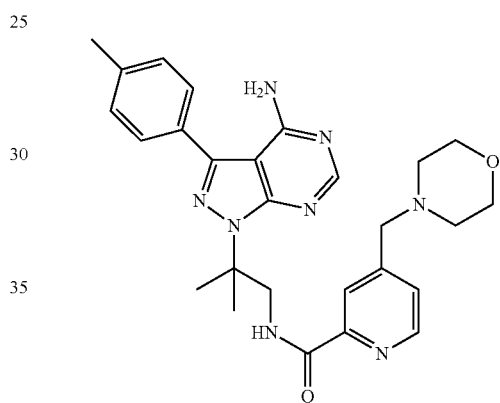

83C: Compound 83C was obtained following the procedure described for the preparation of compound 82D using compound 1E (67 mg, 0.17 mmol) and compound 83B (40 mg, 0.17 mmol). Purification via flash chromatography on $SiO_2$ using methanol/dichloromethane (2:98) afforded compound 83C as a white solid (45 mg, 53%). $^1$H NMR (ppm, $CDCl_3$): δ 9.25 (t, J=6 Hz, 1H), 8.47 (d, J=5 Hz, 1H), 8.35 (s, 1H), 8.17 (s, 1H), 7.69 (d, J=8 Hz, 2H), 7.42 (d, J=4 Hz, 1H), 7.27 (d, J=8 Hz, 2H), 5.80 (br s, 2H), 4.19 (d, J=7 Hz, 2H), 3.69-3.72 (m, 4H), 3.55 (s, 2H), 2.45 (s, 7H), 1.86 (s, 6H). LCMS (+esi): 501 (M+H$^+$).

Example 84

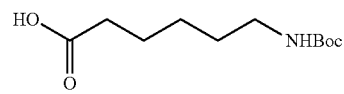 [SMILES: CC(C)(C)OC(=O)NCCCCCC(=O)O]

84A: Compound 84A was prepared according to the procedure described for the preparation of compound 10A using caproic acid (200 mg, 1.32 mmol). A white solid was obtained (296 mg, 97%). $^1$H NMR (ppm, $CDCl_3$): δ 1.44 (s, 9H), 1.52-1.37 (m, 4H), 1.65 (quint., J=7.59 Hz, 2H), 2.35 (t, J=7.35 Hz, 2H), 3.11 (br q, J=6.06 Hz, 2H), 4.54 (br s, 1H).

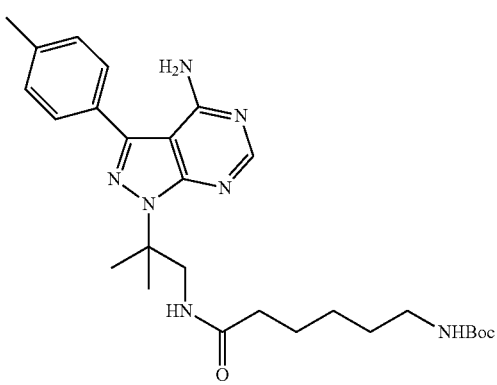 [SMILES: Cc1ccc(-c2nn(C(C)(C)CNC(=O)CCCCCNC(=O)OC(C)(C)C)c3ncnc(N)c23)cc1]

84B: Compound 84B was prepared according to the procedure described for compound 82D using compound 84A (41 mg 0.17 mmol). Purification via flash chromatography on SiO$_2$ using methanol/dichloromethane (2:98) afforded compound 84B as a clear oil (63 mg, 73%). $^1$H NMR (ppm, CDCl$_3$): δ 8.28 (s, 1H), 7.52 (d, J=8 Hz, 2H), 7.31 (d, J=8 Hz, 2H), 7.05 (s, 1H), 5.89 (br s, 2H), 4.62 (s, 1H), 3.92 (d, J=6 Hz, 2H), 2.99-3.05 (m, 2H), 2.41 (s, 3H), 2.12 (t, J=7 Hz, 2H), 1.74 (s, 6H), 1.57-1.62 (m, 2H), 1.39-1.44 (m, 11H), 1.22-1.29 (m, 2H). LCMS (+esi): 510 (M+H$^+$).

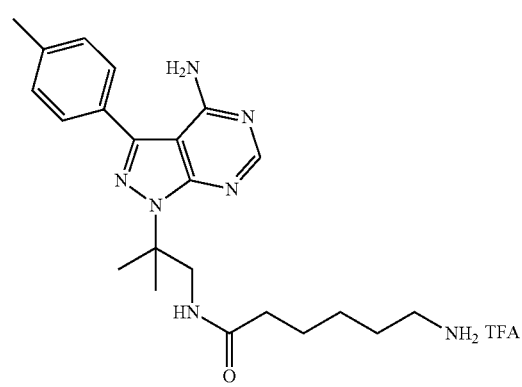 [SMILES: Cc1ccc(-c2nn(C(C)(C)CNC(=O)CCCCCN)c3ncnc(N)c23)cc1]

84C: compound 84B (24 mg, 0.05 mmol) was dissolved in 1 mL of dichloromethane and 0.5 mL of trifluoroacetic acid was added. The mixture was stirred at room temperature for 12 hours. The solvents were concentrated in vacuo and the residue was redissolved in toluene and concentrated again. This process was repeated three times. Compound 84C was obtained as a glassy solid (22 mg, 100%). $^1$H NMR (ppm, CDCl$_3$): δ 8.34 (s, 1H), 7.55 (d, J=8 Hz, 2H), 7.39 (d, J=8 Hz, 2H), 3.88 (s, 2H), 3.29-3.34 (m, 1H), 2.78 (t, J=7 Hz, 2H), 2.44 (s, 3H), 2.05 (t, J=7 Hz, 2H), 1.85 (s, 6H), 1.41-1.59 (m, 4H), 1.28-1.31 (m, 2H). LCMS (+esi): 410 (M+H$^+$).

Example 85

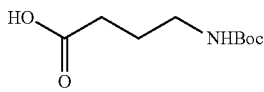

85A: Compound 85A was prepared according to the procedure described for the synthesis of compound 10A using butyric acid (200 mg, 1.52 mmol). A white solid was obtained (206 mg, 67%). $^1$H NMR (ppm, CDCl$_3$): δ 1.44 (s, 9H), 1.82 (quint, J=6.96 Hz, 2H), 2.40 (t, J=6.33 Hz, 2H), 3.18 (br q, J=6.33 Hz, 2H), 4.67 (br s, 1H).

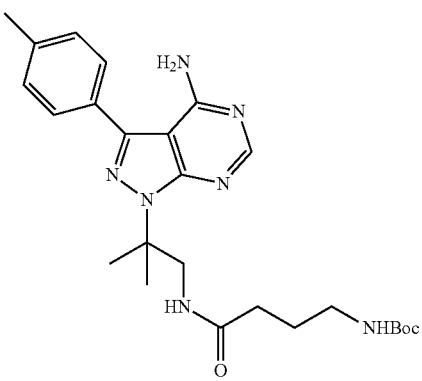 [SMILES: Cc1ccc(-c2nn(C(C)(C)CNC(=O)CCCNC(=O)OC(C)(C)C)c3ncnc(N)c23)cc1]

85B: Compound 85B was prepared according to the procedure described for the synthesis of compound 82D using compound 85A (36 mg 0.17 mmol). Purification via flash chromatography on SiO$_2$ using methanol/dichloromethane (2:98) afforded compound 84B as a clear oil (46 mg, 56%). $^1$H NMR (ppm, CDCl$_3$): δ 8.31 (s, 1H), 7.53 (d, J=8 Hz, 2H), 7.32 (d, J=8 Hz, 2H), 7.19 (s, 1H), 5.74 (br s, 2H), 4.82 (s, 1H), 3.95 (d, J=6 Hz, 2H), 3.08-3.14 (m, 2H), 2.43 (s, 3H), 2.18 (t, J=7 Hz, 2H), 1.75-1.81 (m, 8H), 1.38 (s, 9H). LCMS (+esi): 482 (M+H$^+$).

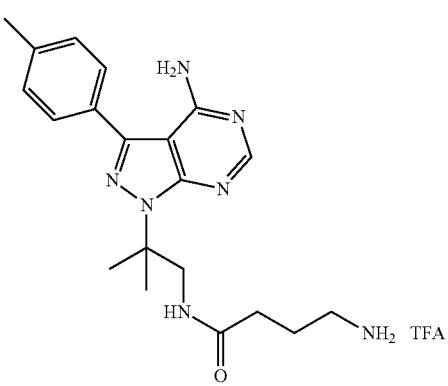 [SMILES: Cc1ccc(-c2nn(C(C)(C)CNC(=O)CCCN)c3ncnc(N)c23)cc1]

85C: Compound 85C was prepared according to the procedure described for the synthesis of compound 84C using compound 85B (24 mg 0.04 mmol). A glassy solid was obtained (26 mg, 100%). $^1$H NMR (ppm, CDCl$_3$): δ 6.86 (s, 1H), 6.06 (d, J=8 Hz, 2H), 5.88 (d, J=8 Hz, 2H), 2.42 (s, 2H), 1.79-1.81 (m, 2H), 2.10 (t, J=7 Hz, 2H), 0.94 (s, 3H), 0.71 (t, J=7 Hz, 2H), 0.24-0.34 (m, 8H). LCMS (+esi): 382 (M+H⁺).

Example 86

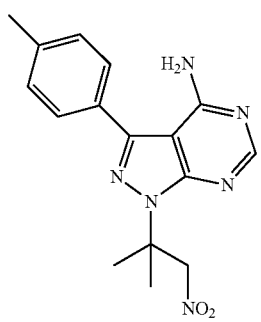 [SMILES: Cc1ccc(-c2nn(C(C)(C)C[N+](=O)[O-])c3ncnc(N)c23)cc1]

86A: 3-p-Tolyl-1H-pyrazolo[3,4-d]pyrimidin-4-amine (100 mg, 0.44 mmol) and 2-methyl-1-nitroprop-1-ene (90 mg, 0.88 mmol) were dissolved in 2 mL of dimethylformamide. The reaction vessel was sealed and the mixture was stirred at 95° C. for 48 hours. The reaction mixture was cooled to room temperature and diluted with water. The aqueous layer was extracted twice with ethyl acetate. The combined organic layers were washed with brine and dried over sodium sulphate. The product was purified via flash chromatography on SiO₂ using methanol/dichloromethane (2:98). Compound 86A was obtained as yellow solid (99 mg, 69%). ¹H NMR (ppm, CDCl₃): δ 8.33 (s, 1H), 7.54 (d, J=8 Hz, 2H), 7.31 (d, J=8 Hz, 2H), 5.72 (br s, 2H), 5.29 (s, 2H), 2.43 (s, 3H), 1.96 (s, 9H). LCMS (+esi): 327 (M+H⁺).

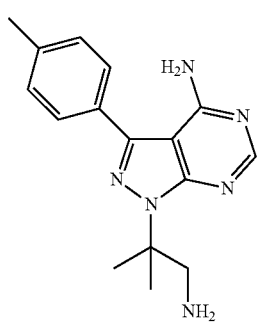

86B: compound 86A (20 mg, 0.06 mmol) was dissolved in 2 mL of ethanol. Next, 589 µL of 6M of hydrogen chloride was added followed by zinc dust (60 mg, 0.92 mmol). The reaction was stirred at room temperature for 2 hours. The excess zinc was removed by filtration and the ethanol was concentrated in vacuo. Saturated sodium hydrogen carbonate was added until ph 9 and dichloromethane was added to the aqueous layer and was stirred for 30 minutes. The aqueous layer was further extracted with dichloromethane and the crude compound 86B was obtained. LCMS (+esi): 297 (M+H⁺).

Example 87

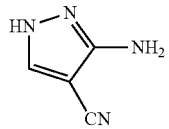

87A: To a solution of hydrazine in water (65%, 2.5 g, 50 mmol) was added portionwise ethoxymethylene malonitrile (3.35 g, 28 mmol). An exothermic reaction occurred during the addition. After the addition was complete, the brown solution was heated to 90° C. for 5 hours. The resulting solution was placed in a refrigerator for 2 days. Light brown crystals were collected by filtration, washed with cold water and ether and dried under vacuum to give compound 87A as brown crystals (1.78 g, 60% yield). ¹H NMR (ppm, DMSO): δ 7.70 (s, 1H), 5.99 (s, 2H).

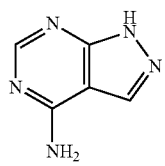

87B: Compound 87A (800 mg, 7.4 mmol) was dissolved in 8 mL of formamide and the resulting solution was heated at 180° C. overnight under nitrogen atmosphere. The reaction was cooled and water was added. The resulting solid was filtered and rinsed with cold water. The solid was dried in vacuo to give compound 87B as a pale yellow powder (790 mg, 79% yield). ¹H NMR (ppm, DMSO): δ 8.13 (s, 1H), 8.07 (s, 1H) 7.57 (s, 2H).

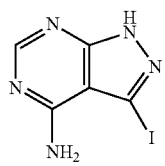 [SMILES: Nc1ncnc2[nH]nc(I)c12]

87C: Compound 87B (700 mg, 5.18 mmol) and N-iodosuccinimide (1.75 g, 7.77 mmol) were dissolved in 12 mL of N,N-dimethylformamide and stirred at 80° C. overnight under nitrogen atmosphere. The mixture was cooled and 30 mL of water were added. The resulting solid was filtered and rinsed with cold ethanol. The product was dried in vacuo. Compound 87C was obtained as a brown powder (935 mg, 69% yield). ¹H NMR (ppm, DMSO): δ 8.17 (s, 1H). LCMS (+esi): 262.0 (M+H⁺).

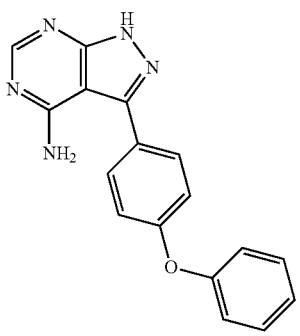 [SMILES: Nc1ncnc2[nH]nc(-c3ccc(Oc4ccccc4)cc3)c12]

87D: Compound 87C (200 mg, 0.77 mmol), K₃PO₄ (488 mg, 2.30 mmol), 4-phenoxybenzene boronic acid (491 mg, 2.32 mmol) and Tetrakis-(triphenylphosphine)palladium (124 mg, 0.11 mmol) were dissolved in 2.5 mL of dioxane in a microwave vial. The vial was sealed and the reaction mixture was heated to 180° C. for 10 min under microwave irradiation. The reaction mixture was partitioned between water and ethylacetate and the organic layer was separated, dried over anhydrous Na₂SO₄, filtered and concentrated. The residue was purified by column chromatography on SiO₂ using MeOH/CH₂Cl₂ (0:100 to 10:90). Compound 87D was obtained as a white powder (92 mg, 41% yield). ¹H NMR (ppm, DMSO): δ 8.21 (s, 1H), 7.66 (d, J=8.8 Hz, 2H), 7.43 (t, J=7.9 Hz, 2H), 7.21-7.11 (m, 5H). LCMS (+esi): 304.2 (M+H⁺).

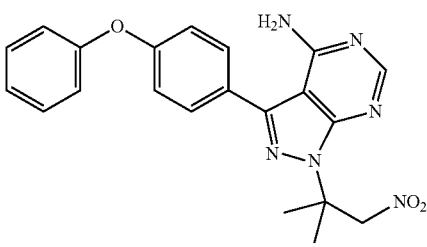

87E: Compound 87D (80 mg, 0.26 mmol) was dissolved in 2 mL of DMF. 2-methyl-1-nitroprop-1-ene (53 mg, 0.52 mmol) was added to the solution and the resulting mixture was stirred at 95° C. for 2 days. The reaction mixture was poured into water and extracted three times with ethylacetate. The combined organic layers were dried over anhydrous Na₂SO₄, filtered and concentrated. The crude product was purified by column chromatography on SiO₂ using MeOH/CH₂Cl₂ (0:100 to 5:85). Compound 87EA was obtained as a brown oil (33 mg, 31% yield). ¹H NMR (ppm, CDCl₃): δ 8.33 (s, 1H), 7.61 (d, J=8.8 Hz, 2H), 7.41-7.37 (m, 2H), 7.17-7.04 (m, 5H), 5.26 (s, 2H), 1.97 (s, 6H).

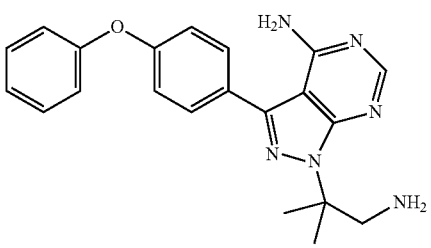 [SMILES: CC(C)(C[N+](=O)[O-])n1nc(-c2ccc(Oc3ccccc3)cc2)c2c(N)ncnc21]

87D: Compound 87E (10 mg, 0.025 mmol) was placed into an oven dried round bottom flask. 1 mL of anhydrous methanol and glacial acetic acid (5 μL, 0.09 mmol) were then added followed by 20% palladium hydroxyde (16 mg, 0.022 mmol). The round bottom flask was filled with hydrogen gas and evacuated three times. The reaction was stirred at room temperature overnight under hydrogen atmosphere. The mixture was then filtered through a plug of celite and concentrated. Compound 87D was used in the next step without further purification. LCMS (+esi): 375.1 (M+H⁺).

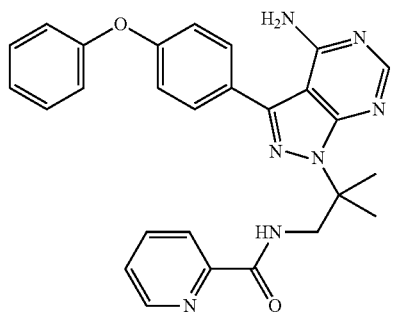 [SMILES: CC(C)(CNC(=O)c1ccccn1)n1nc(-c2ccc(Oc3ccccc3)cc2)c2c(N)ncnc21]

87E: Compound 87C (8 mg, 0.021 mmol) was dissolved in 1.5 mL of N,N-dimethylformamide. 1-ethyl-3-(3-dimethylaminopropyl) carbodiimide hydrochloride (4.7 mg, 0.025 mmol), 4-Dimethylaminopyridine (7.8 mg, 0.064 mmol) and picolinic acid (2.7 mg, 0.022 mmol) were added to the solution. The resulting mixture was stirred at room temperature overnight. Water was added to the solution and the mixture was extracted three times with ethylacetate. The combined organic layers were dried over anhydrous Na₂SO₄, filtered and concentrated. The crude product was purified by preparative HPLC. Compound 87E was obtained as a white powder (1.6 mg, 16% yield). ¹H NMR (ppm, CDCl₃): δ 8.51 (s, 1H), 8.25 (s, 1H), 8.21-8.14 (m, 1H), 7.85-7.82 (m, 1H), 7.65 (d, J=8.7 Hz, 1H), 7.43-7.36 (m, 3H), 7.23-7.08 (m, 6H), 4.17 (d, J=4.7 Hz, 1H), 4.15 (d, J=4.7 Hz, 1H), 1.90 (s, 4H), 1.82 (s, 2H). LCMS (+esi): 480.2 (M+H⁺).

Example 88

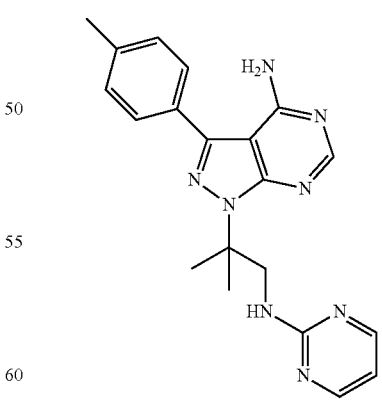

Compound 1E (75 mg, 0.2 mmol), 2-chloropyrimidine (25 mg, 0.22 mmol), Cs₂CO₃ (196 mg, 0.6 mmol) were stirred at 80° C. in 250 mL of DMF for 12 hours. After this time, water was added. The white solid that precipitated was collected by filtration and rinsed with water. It was then further purified by preparative HPLC. A white solid was obtained (m=12 mg, 16%). ¹H NMR (ppm, CDCl₃): δ 8.3 (s, 1H), 8.21 (d, J=4.7 Hz, 2H), 7.55 (d, J=8.0 Hz, 2H), 7.34 (d, J=8.4 Hz, 2H), 6.48 (t, J=4.8 Hz, 1H), 6.15 (br t, J=6.0 Hz, 1H), 4.34 (d, J=6.6 Hz, 2H), 2.44 (s, 3H), 1.84 (s, 6H). LCMS (+esi): 375.1 (M+H⁺).

Example 89

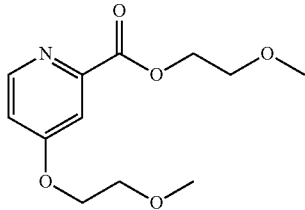 [SMILES: COCCOC(=O)c1cc(OCCOC)ccn1]

89A: Sodium (54 mg, 2 mmol) was placed into an oven dried Schlenk tube. 5 mL of anhydrous tetrahydrofuran were then added followed by 2-methoxy-ethanol (0.18 mL, 2 mmol). A gas evolution occurred. The reaction was stirred at room temperature for 30 minutes. It was then heated to 50° C. until all the sodium had disappeared. In another flask 4-chloropicolinic tert-butyl ester (0.5 g, 2 mmol) was dissolved in 5 mL of anhydrous tetrahydrofuran. The solution of the alkoxide was then added to the reaction mixture and the reaction was stirred at reflux for 5 hours. Another solution of alkoxide was prepared and was added to the reaction mixture. The reaction was stirred for a further 15 hours at reflux. The reaction was then cooled to room temperature and the solvent was removed in vacuo. The residue was taken up into ethyl acetate and washed several times with water. The organic layer was dried over sodium sulphate and concentrated. The crude product was purified via flash chromatography on SiO₂ using methanol/dichloromethane (5:95). Compound 89A was obtained as a brown oil (328 mg, 55%). ¹H NMR (CDCl₃, 300 MHz): δ 8.54 (d, J=8 Hz, 1H), 7.69 (s, 1H), 6.98 (d, J=8 Hz, 1H), 4.53 (t, J=5 Hz, 2H), 4.21 (t, J=5 Hz, 2H), 3.74 (m, 4H), 3.43 (s, 3H), 3.41 (s, 3H). LCMS (+esi): 256 (M+H⁺).

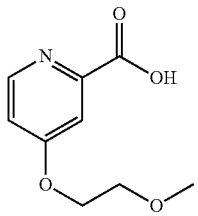

89B: Compound 89A (50 g, 0.18 mmol) was dissolved in 1 mL of methanol and 0.5 mL of 2M sodium hydroxide was added. The reaction was stirred at room temperature overnight. The methanol was concentrated down and the aqueous layer was acidified to pH 2 with 2 mL of 1M hydrogen chloride. The aqueous layer was placed on a freeze drier overnight. Compound 89B was used in the next step without further purification.

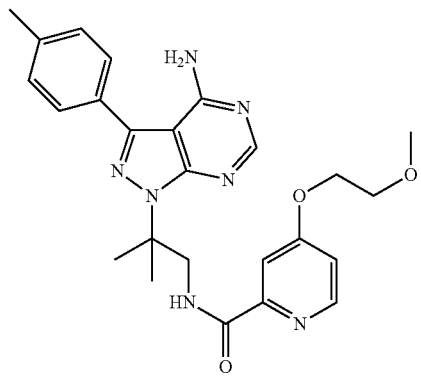

89C: Compound 89C was obtained following the procedure described for the preparation of compound 82D using compound 1E (67 mg, 0.17 mmol) and compound 89B (37 mg 0.19 mmol). Purification via flash chromatography on SiO₂ using methanol/dichloromethane (2:98) afforded compound 89C as a white solid (54 mg, 67%). ¹H NMR (CDCl₃, 300 MHz): δ 9.24 (s, 1H), 8.31 (m, 2H), 7.73 (s, 1H), 7.68 (d, J=7 Hz, 2H), 7.26 (d, J=7 Hz, 2H), 6.91 (d, J=8 Hz, 1H), 5.82 (br s, 2H), 4.16 (m, 4H), 3.74 (m, 2H), 3.39 (s, 3H), 2.43 (s, 3H), 1.84 (s, 6H). LCMS (+esi): 476.6 (M+H⁺).

Biological Data

Protocol for SRC Kinase Inhibition Assay.

Compounds of the invention were tested for in vitro activity in the following assay: A biotin labeled peptide was used as substrate (amino acid sequence: Biotin-Glu-Gly-Pro-Trp-Leu-Glu-Glu-Glu-Glu-Glu-Ala-Tyr-Gly-Trp-Met-Asp-Phe-NH₂). Src recombinant enzyme was purchased as N-terminally His₆ tagged full-length human protein. The 15 µL assay reactions were run in Greiner brand white 384-well low volume plates. All reactions contained 10 mM HEPES pH 7.4, 25 mM NaCl, 10 mM MgCl₂, 0.01% (v/v) Tween-20, 50 µM Na₃VO₄, 0.01% (w/v) albumin from chicken egg white, 111 nM peptide substrate, 80 µM ATP, and 0.3 ng/reaction Src enzyme, with the enzyme being omitted from negative control reactions. Compounds were added in a volume of 100 nL from dilution series made up in DMSO, positive and negative control reactions receiving the same volume DMSO without compounds. The plates were sealed with adhesive seals and incubated for 90 minutes at 30 degree Celsius. The reactions were stopped with the detection reagents added at the same time. Product formation was quantified as photochemiluminescence between PerkinElmer AlphaScreen™ beads, using Streptavidin-coated donor and anti-phosphotyrosine (P-Tyr-100) acceptor beads. To each reaction, 5 µL containing 10 mM HEPES pH 7.4, 25 mM NaCl, 100 mM EDTA, 0.01% (v/v) Tween-20, and 6.25 µg/mL of each bead type were added. Plates were incubated for 5 hours before being read on a PerkinElmer EnVision™ plate reader in HTS Alphascreen™ mode. IC₅₀ values were obtained by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC₅₀ value, and D is the slope factor.

| Example No | IC50 (SRC) |
|---|---|
| 1 (compound 1E) | B |
| 2 | B |
| 3 | C |
| 4 (compound 4C) | B |
| 5 (compound 5B) | A |
| 6 (compound 6B) | A |
| 7 | A |
| 8 | B |
| 9 | C |
| 10 (compound 10C) | A |
| 11 | B |
| 12 | A |
| 13 (compound 13C) | A |
| 14 | B |
| 15 | B |
| 16 | C |
| 17 | A |
| 18 | B |
| 19 | A |
| 20 | B |
| 21 | B |
| 22 | B |
| 23 | A |
| 24 | C |
| 25 | C |
| 26 | A |
| 27 | B |
| 28 | A |
| 29 | B |
| 30 | B |
| 31 | B |
| 32 | B |
| 33 | B |
| 34 | B |
| 35 | B |
| 36 | B |
| 37 | B |
| 38 | B |
| 39 | B |
| 40 | B |
| 41 | B |
| 42 | A |
| 43 | B |
| 44 | B |
| 45 | C |
| 46 | B |
| 47 | B |
| 48 | B |
| 49 | C |
| 50 | B |
| 51 | B |
| 52 | C |
| 53 | B |
| 54 | B |
| 55 | C |
| 57 | C |
| 56 | A |
| 58 | A |
| 59 | B |
| 60 | B |
| 61 | A |
| 62 | A |
| 63 | B |
| 64 | A |
| 65 | B |
| 66 | A |
| 67 | C |
| 68 (compound 68B) | B |
| 69 (compound 69C) | A |
| 70 (compound 70C) | B |
| 72 | A |
| 73 | C |
| 71 | D |
| 74 (compound 74E) | B |
| 75 | A |
| 76 | C |
| 77 | A |
| 78 | B |
| 80 | B |
| 81 | A |
| 82 | A |
| 83 | A |
| 84 (compound 84C) | B |
| 85 (compound 85C) | B |
| 88 | B |
| 89 | A |

A: 0.001 µM–0.10 µM
B: 0.10 µM–1.0 µM
C: 1.0 µM–10 µM
D: >10 µM

Example of Cellular Activity
A. Cells, Inhibitors and Incubation
1. Cell Lines
LIM 1899 colon carcinoma derived epithelial cells were grown in RPMI+Adds[1]+10% FCS.

[1] Additives for culture of LIM cell lines: 10 µM thioglycerol, 0.025 U/mL insulin, 1 µg/mL hydrocortisone 2. Cell Plating in 96 Well Plate.
Assay medium: RPMI+Adds+5% FCS
Cells are trypsinized, washed once in assay medium and brought to the required concentration as described below:
Need $10^4$ cells per well in 100 µL per well=$10^5$ per mL for plating
After washing, cells were resuspended in 5 mL and counted (1×T75 flask gives approx 2–3×10 eg$^6$ per mL).
Cells were then diluted to $10^5$ cells/mL (need 10 mL minimum per plate).
Eg. Cell count in 5 mL is 25×$10^5$/mL
For $10^5$/mL, dilute 1 mL to 25 mL
100 µL per well cells were plated with multistepper pipette, over the whole plate. Plates were incubated overnight at 37° C.+5% $CO_2$ incubator.
3. Inhibitor Stocks
Inhibitors were dissolved in DMSO for 10 mM stocks. MW and amount of compound given was used to calculate the volume required for each.
4× the highest concentration of the compound in the assay was calculated to prepare the working stocks.
eg $1^{st}$ well final concentration in assay was 10 µM.
Therefore working stock was 40 µM
Stock solution is 10 mM→40 µM=4 µl in 1.0 mL assay medium for working stock.
4. Plate Plan:
Rows A,B: Inhibitor 1
Rows C,D: Inhibitor 2
Rows E,F: Inhibitor 3
Row G: RPMI+Adds+5% FCS (=maximum growth)
Row H: RPMI+Adds serum free (=minimum growth)
5. Titration of Inhibitors
A 96 well plate was used to titrate the inhibitors for each assay plate:
150 µL assay medium was added to each well of a 96 well plate.
150 µL of Inhibitor 1 working stock was added wells A1 and B1.
Repeated with Inhibitor 2 to C1 and D1
Repeated with Inhibitor 3 to E1 and F1
Serial ½ dilutions were performed across the plate, rows A to F, left to right with 150 µL.

6. Transfer Titrated Inhibitors to Cell Assay Plate: Final Volume 200 μl
   Using a multichannel pipette, 100 μL was transferred from the corresponding wells of the titration plate to the cell assay plate, rows A to G.
   Row H: medium was carefully removed from the cell wells with a 200 μL tip, and replaced with 200 μL serum free medium.
7. Incubation
   Plates were incubated for 4 days at 37° C. with 5% $CO_2$.
B. Use of MTT to Measure Cell Growth
1. MTT Preparation and Storage
   MTT Sigma M-2128 5 g
   Dissolved in PBS, at 5 mg/mL
   5 g bottle dissolved in 1 liter PBS (some impurities remain)
   Filter sterilized and aliquoted in 50 mL tubes, stored at −20° C.
   As needed, 50 mL tube was thawed and aliquoted in 5 mL tubes, re-stored at −20° C.
   Stable at 4° C. for 1 month (unstable if left at 37° C. too long while thawing)
2. MTT Solvent
   a. 1M HCl:
      Mixed 44.6 mL conc HCl (11.2M) in 500 mL DDW
   b. Acidified isopropanol (Isopropanol with 0.04 N HCl):
      Mixed 20 mL 1M HCl with 480 mL isopropanol (Propan-2-ol, iso-Propyl Alcohol)
3. MTT Assay
   After cell incubation (above):
   Added 10 μL MTT to each well.
   Incubated 4 hrs in 37° C. incubator.
   Spun plates, 5 min, 1500 rpm.
   Carefully flicked out medium into the sink, without disturbing the crystals.
   Added 200 μL acidified isopropanol per well.
   Placed on plate shaker, RT, speed 6.5, for 10 min-30 min.
   Read OD of plates on Thermo Multiskan Ex, at 560/690 nm.

REFERENCE

Mosmann, T.
Rapid colorimetric assay for cellular growth and survival: application to proliferation and cytotoxic assays. *Journal of Immunological Methods* (1983), 65:55-63.
Table with Examples of Cellular Data

| Example | LIM1215 | LIM2537 | RasNIH3T3 | LIM1899 |
|---|---|---|---|---|
| 12 | 0.17 | 0.17 | 0.11 | 0.17 |
| 11 | | | | 1.7 |
| 1 (compound 1E) | 8.5 | | | |
| 42 | 0.9 | | 1.9 | |
| 57 | 1.6 | | >20 | |
| 56 | 0.4 | | 1.62 | |
| 59 | 3.1 | | >20 | |
| 60 | 1.9 | | 17 | |
| 61 | 0.8 | | 1.83 | 1.6 |
| 62 | 0.25 | | 0.35 | |
| 63 | 2.6 | | 6.29 | 1.7 |
| 64 | | 1.1 | 0.63 | 0.88 |
| 65 | 0.96 | | 1.67 | 0.9 |
| 66 | 0.52 | | 0.5 | 0.31 |
| 73 | | | | 1.1 |
| 71 | | | | 3.1 |
| 74 (compound 74F) | | >10 | | >20 |
| 75 | | 1.6 | | 0.9 |
| 76 | | >10 | | 19 |
| 77 | | >10 | | |
| PP1 | 0.25 | | 9.25 | |
| Dasatinib | 2 | 4 to above 10 | 9 to 12 | 1.2 |

The compounds in this invention display cellular activities against a range of tumour or transformed cell lines in particular colon cancer cell lines such as LIM1215, LIM2537 and LIM1899.

The invention claimed is:
1. A compound of the following Formula (I):

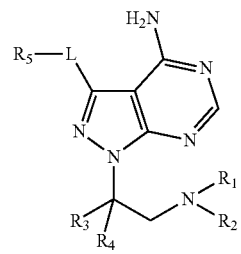

Formula (I)

or a salt thereof, wherein:
$R_1$ is selected from the group consisting of hydrogen, optionally substituted alkyl, —($SO_2$)-optionally substituted aryl, —($SO_2$)-optionally substituted heteroaryl, optionally substituted heteroaryl, optionally substituted heterocyclyl, optionally substituted aryl, and C(=X)—$R_6$;
$R_2$ is selected from the group consisting of hydrogen and $C_1$-$C_3$ alkyl;
$R_3$ and $R_4$ are independently $C_1$-$C_3$ alkyl;
L is selected from the group consisting of a bond, —O—, —S—, —N($R_9$)—, optionally substituted alkylene, and —N($R_9$)C(X')—N($R_{9'}$)—, where each of $R_9$ and $R_{9'}$ is independently hydrogen or $C_1$-$C_4$ alkyl;
$R_5$ is selected from the group consisting of optionally substituted aryl, optionally substituted heteroaryl, optionally substituted heterocyclyl, and optionally substituted cycloalkyl;
X and X' are independently selected from the group consisting of O, S and $NR_7$;
$R_6$ is selected from the group consisting of optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;
$R_7$ is selected from the group consisting of hydrogen, cyano, optionally substituted $C_1$-$C_6$ alkyl, optionally substituted aryl, $S(O)_2R_8$, and optionally substituted aminoacyl; and
$R_8$ is selected from the group consisting of optionally substituted $C_1$-$C_6$ alkyl and optionally substituted aryl.
2. The compound of claim 1, or a salt thereof, wherein L is a bond or $CH_2$.

3. The compound of claim 1, or a salt thereof, wherein L is a bond and $R_5$ is a phenyl group substituted one or two times with substituent groups independently selected from the group consisting of halo, hydroxyl, acyl, $C_1$-$C_8$ alkyl, $C_2$-$C_6$ alkenyl, $C_2$-$C_6$ alkenyloxy, amino, oxyacylamino, $C_1$-$C_8$ alkoxy, aryl, aryloxy, carboxyl, cycloalkyl, cycloalkyloxy, cyano, sulphate, phosphate, heterocyclyl, heterocyclyloxy, heteroaryl, heteroaryloxy, trihalomethyl, and trialkylsilyl.

4. The compound of claim 1, or a salt thereof, wherein -$LR_5$ is selected from the group consisting of

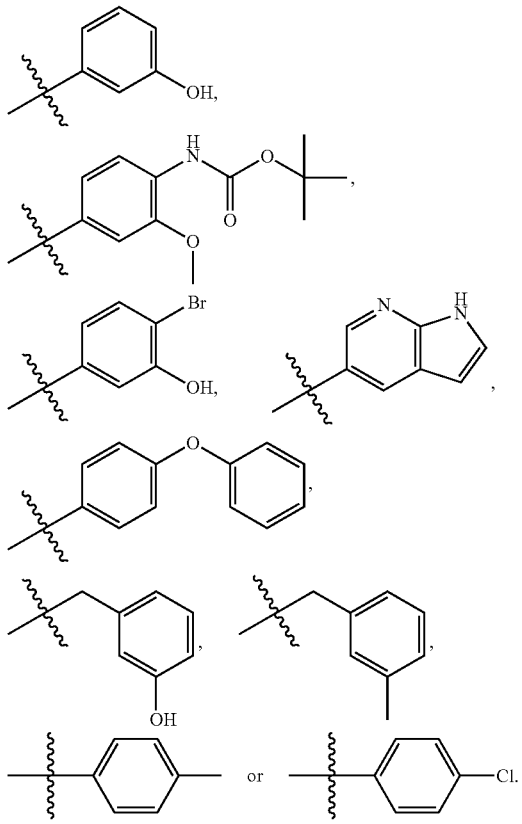

5. The compound of claim 1 of the following Formula (Ia):

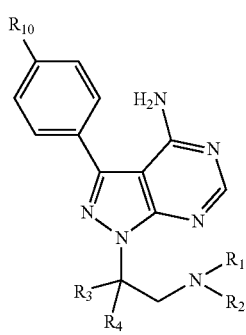

Formula (Ia)

or a salt thereof, wherein:

$R_1$ is selected from the group consisting of hydrogen, optionally substituted alkyl, —($SO_2$)-optionally substituted aryl, —($SO_2$)-optionally substituted heteroaryl, optionally substituted heteroaryl, optionally substituted heterocyclyl, optionally substituted aryl, and C(=X)—$R_6$;

$R_2$ is selected from the group consisting of hydrogen and $C_1$-$C_3$ alkyl;

$R_3$ and $R_4$ are independently $C_1$-$C_3$ alkyl;

$R_{10}$ is selected from the group consisting of hydrogen, halo, $C_1$-$C_4$ alkyl, $C_2$-$C_4$ alkynyl, $C_2$-$C_4$ alkenyl, arylalkyl, $OR^1$ (where $R^1$ is H, $C_1$-$C_3$ alkyl or aryl), $COOR^2$ (where $R^2$ is H, $C_1$-$C_3$ alkyl or aryl), nitro, cyano, amino, trihalomethyl, thio, and thio $C_1$-$C_3$ alkyl;

X is selected from the group consisting of O, S and $NR_7$;

$R_6$ is selected from the group consisting of optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;

$R_7$ is selected from the group consisting of hydrogen, cyano, optionally substituted $C_1$-$C_6$ alkyl, optionally substituted aryl, $S(O)_2R_8$, and optionally substituted aminoacyl; and $R_8$ is selected from the group consisting of optionally substituted $C_1$-$C_6$ alkyl and optionally substituted aryl.

6. The compound of claim 1 of the following Formula (Ib):

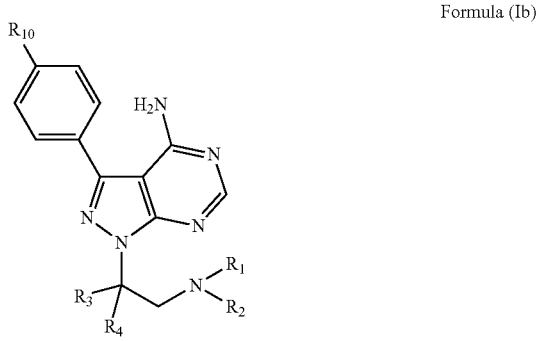

Formula (Ib)

or a salt thereof, wherein:

$R_1$ is selected from the group consisting of hydrogen, optionally substituted alkyl, —($SO_2$)-optionally substituted aryl, —($SO_2$)-optionally substituted heteroaryl, optionally substituted heteroaryl, optionally substituted heterocyclyl, optionally substituted aryl, and C(=X)—$R_6$;

$R_2$ is selected from the group consisting of hydrogen and $C_1$-$C_3$ alkyl;

$R_3$ and $R_4$ are independently $C_1$-$C_3$ alkyl;

$R_{10}$ is $C_1$-$C_4$ alkyl or halo;

X is selected from the group consisting of O, S and $NR_7$;

$R_6$ is selected from the group consisting of optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;

R$_7$ is selected from the group consisting of hydrogen, cyano, acyl, optionally substituted C$_1$-C$_6$ alkyl, optionally substituted aryl, S(O)$_2$R$_8$, and optionally substituted aminoacyl; and R$_8$ is selected from the group consisting of optionally substituted C$_1$-C$_6$ alkyl, and optionally substituted aryl.

7. The compound of claim 1 of the following Formula (Ic):

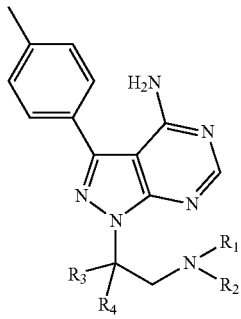

Formula (Ic)

or a salt thereof, wherein:
R$_1$ is selected from the group consisting of hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;

R$_2$ is selected from the group consisting of hydrogen and C$_1$-C$_3$ alkyl;

R$_3$ and R$_4$ are independently C$_1$-C$_3$ alkyl;

X is selected from the group consisting of O, S and NR$_7$;

R$_6$ is selected from the group consisting of optionally substituted C$_1$-C$_6$ alkyl, optionally substituted C$_1$-C$_6$ alkoxy, optionally substituted C$_2$-C$_6$ alkenyl, optionally substituted C$_2$-C$_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;

R$_7$ is selected from the group consisting of hydrogen, cyano, optionally substituted C$_1$-C$_6$ alkyl, optionally substituted aryl, S(O)$_2$R$_8$, and optionally substituted aminoacyl; and R$_8$ is selected from the group consisting of optionally substituted C$_1$-C$_6$ alkyl and optionally substituted aryl.

8. The compound of claim 1, or a salt thereof, wherein R$_3$ and R$_4$ are independently selected from C$_1$-C$_2$ alkyl.

9. The compound of claim 1, or a salt thereof, wherein R$_2$ is hydrogen or methyl.

10. The compound of claim 1 of the following Formula (Ie):

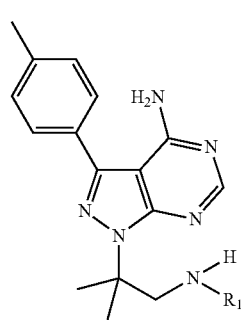

Formula (Ie)

or a salt thereof, wherein:
R$_1$ is selected from the group consisting of hydrogen, optionally substituted alkyl, —(SO$_2$)-optionally substituted aryl, —(SO$_2$)-optionally substituted heteroaryl, optionally substituted heteroaryl, optionally substituted heterocyclyl, optionally substituted aryl, and C(=X)—R$_6$;

X is selected from the group consisting of O, S and NR$_7$;

R$_6$ is selected from the group consisting of optionally substituted C$_1$-C$_6$ alkyl, optionally substituted C$_1$-C$_6$ alkoxy, optionally substituted C$_2$-C$_6$ alkenyl, optionally substituted C$_2$-C$_6$ alkynyl, optionally substituted heteroaryl, optionally substituted heterocyclyl, optionally substituted aryl, optionally substituted cycloalkyl, optionally substituted cycloalkenyl, optionally substituted amino, optionally substituted acylamino, optionally substituted arylacyl, optionally substituted heteroarylacyl, optionally substituted heterocyclylacyl, optionally substituted cycloalkylacyl, and trihalomethyl;

R$_7$ is selected from the group consisting of hydrogen, cyano, optionally substituted C$_1$-C$_6$ alkyl, optionally substituted aryl, S(O)$_2$R$_8$, and optionally substituted aminoacyl; and R$_8$ is selected from the group consisting of optionally substituted C$_1$-C$_6$ alkyl and optionally substituted aryl.

11. The compound of claim 1, or a salt thereof, wherein R$_1$ is selected from the group consisting of:
a) hydrogen;
b) optionally substituted C$_1$-C$_6$ alkyl;
c) —(SO$_2$)-optionally substituted aryl or —(SO$_2$)-optionally substituted heteroaryl; and
d) C(=X)—R$_6$ where X is O, S or NR$_7$, wherein R$_6$ is selected from the group consisting of optionally substituted alkyl, optionally substituted aryl, optionally substituted heteroaryl, optionally substituted aryl-C$_{1-3}$ alkyl, optionally substituted heteroaryl-C$_{1-3}$alkyl, optionally substituted aryl-C$_{1-3}$alkoxy, optionally substituted heteroaryl-C$_1$-C$_3$alkoxy, trifluoroalkyl, and NR'R" (where R' is hydrogen or C$_{1-3}$ alkyl, and R" is hydrogen, optionally substituted alkyl, or optionally substituted arylacyl) and R$_7$ is hydrogen, optionally substituted aryl, or optionally substituted C$_{1-3}$alkyl.

12. The compound of claim 1, or a salt thereof, wherein R$_1$ is selected from the group consisting of:

-continued

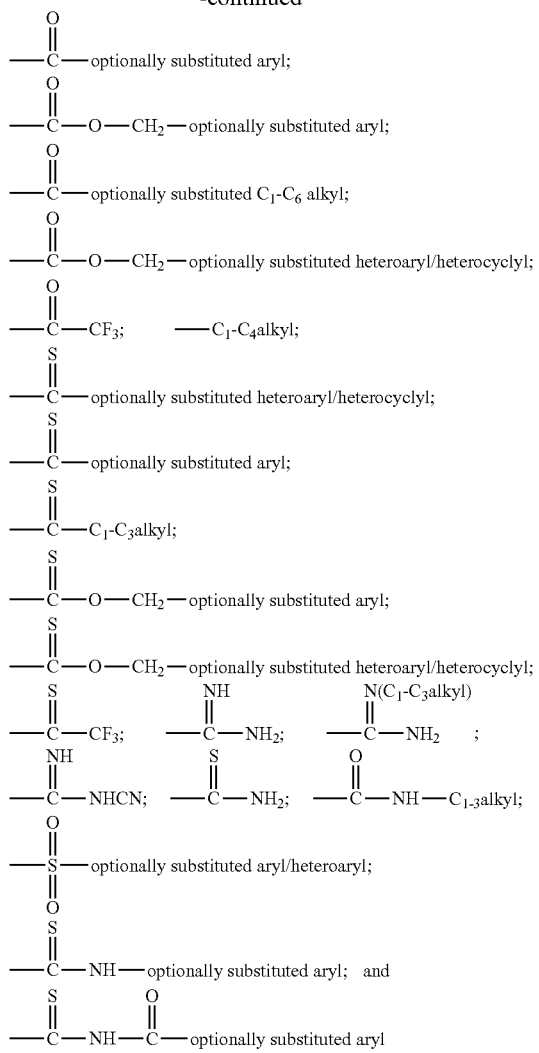

wherein heteroaryl represents:
(i) a 5-membered heteroaryl group selected from the group consisting of pyrrole, 2H-pyrrole, furan, pyrazole, thiophene, isothiazole, thiazole, 1,2,3-triazole, 1,2,4-triazole, 1,2,3-oxadiazole, 1,2,5-oxadiazole, 1,3,4-thiadiazole, tetrazole, imidazole, oxazole, and isoxazole; or
(ii) a 6-membered heteroaryl group selected from the group consisting of pyridine, pyrimidine, pyrazine, and 1,3,5-triazine;

wherein heterocyclyl represents:
(i) 5-membered heterocyclyl group selected from the group consisting of 1-pyrroline, 2-pyrroline, 3-pyrroline, pyrrolidine, tetrahydrofuran, tetrahydrothiophene, 2-pyrazoline, 3-pyrazoline, 2-imidazoline, pyrazolidine, imidazolidine, 3-dioxolane, thiazolidine, and isoxazolidine; or
(ii) a 6-membered heterocyclyl group selected from the group consisting of 2H-pyran, 4H-pyran, 3,4-dihydro-2H-pyran, piperidine, 1,4-oxazine, 1,4-dioxine, piperazine, morpholine, 1-4-dioxane, 1,4-thazine, thiomorpholine, 1,4-oxathane, 1,4-dithane, 1,3,5-trioxane, 6H-1,2,5-thiadiazine, 2H-1,5,2-dithiazine, and 1,3,5-trithiane;

wherein aryl is selected from the group consisting of phenyl, napthyl and anthracenyl;

wherein the heteroaryl, heterocyclyl or aryl group may be substituted from 1 to 4 times with substituent groups independently selected from the group consisting of hydroxyl, acyl, $C_1$-$C_4$ alkyl, $C_1$-$C_4$ alkoxy, $C_2$-$C_6$ alkenyl, $C_2$-$C_6$ alkenyloxy, $C_2$-$C_6$ alkynyl, $C_2$-$C_6$ alkynyloxy, —O—$(CH_2)_n$—OH, —O—$(CH_2)_n$—$OC_1$-$C_3$ alkyl, —$(CH_2)_n$-amino, —$(CH_2)_n$-di$C_1$-$C_3$ alkyl amino, —$(CH_2)_n$-aminoacyl, —$(CH_2)_n$-thio, arylalkyl, —$(CH_2)_n$-arylalkoxy, —$(CH_2)_n$-aryl, —$(CH_2)_n$-aryloxy, —$(CH_2)_n$-carboxyl, —$(CH_2)_n$-cycloalkyl, cyano, halogen, nitro, sulphate, phosphate, —$(CH_2)_n$-heterocyclyl, —$(CH_2)_n$-heteroaryl, —$(CH_2)_n$-trihalomethyl, and —$(CH_2)_n$-trialkylsilyl, wherein n is an integer from 0-6.

13. The compound of claim 1, or a salt thereof, wherein $R_1$ is $C(O)R_6$.

14. The compound of claim 1 of the following Formula (If):

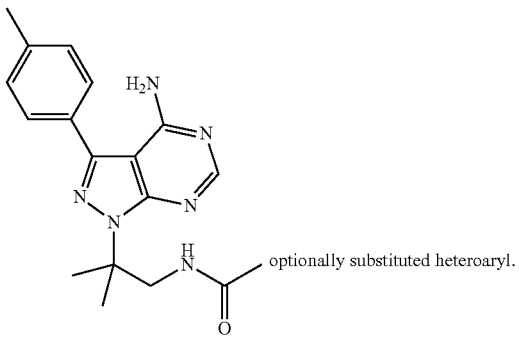

Formula (If)

15. The compound according to claim 14, or a salt thereof, wherein the optionally substituted heteroaryl group is pyridyl or thiazolyl.

16. A compound represented by one of the following formulae:

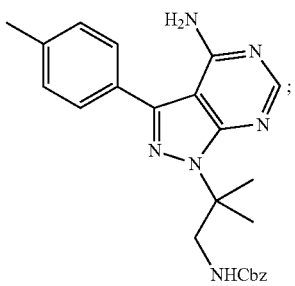

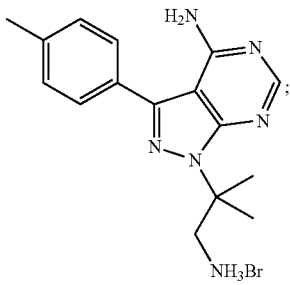

131
-continued
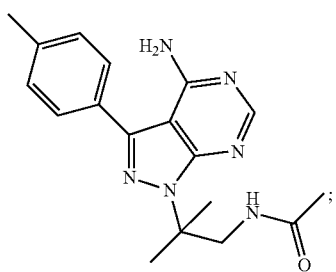
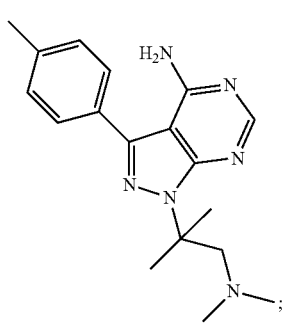
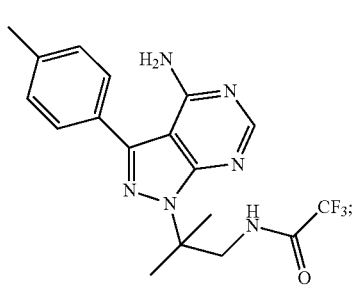
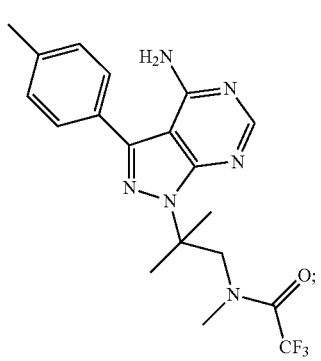
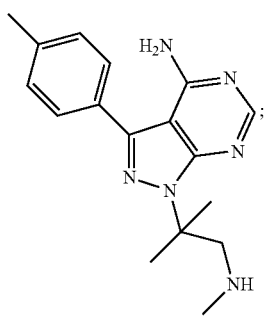
132
-continued
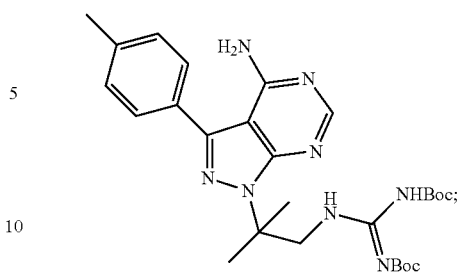
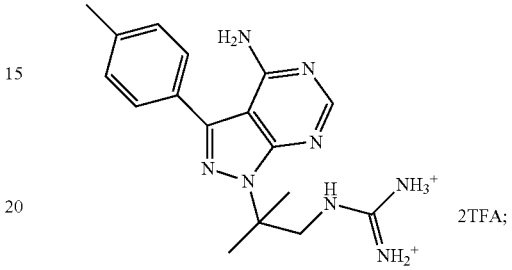
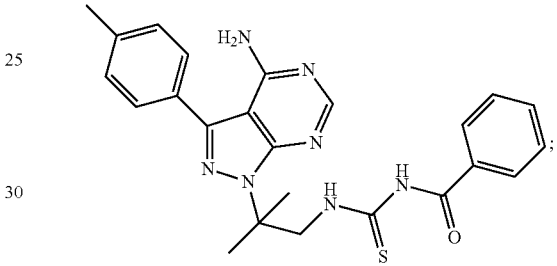
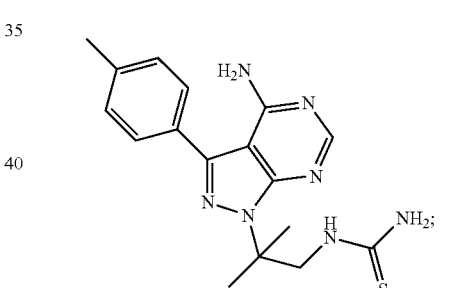
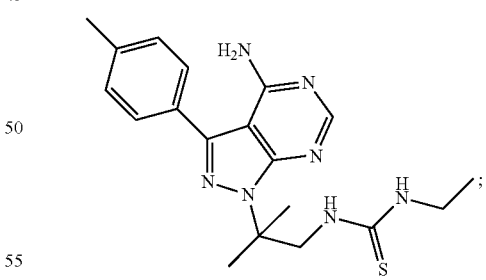
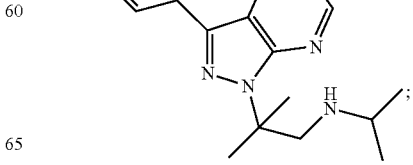

133
-continued
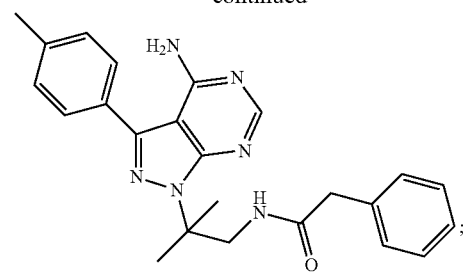
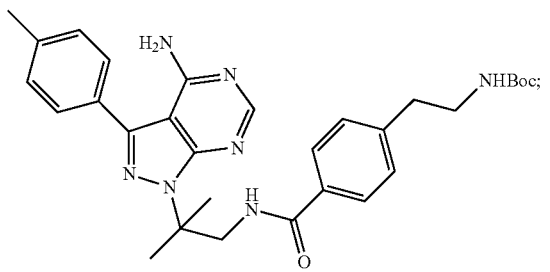
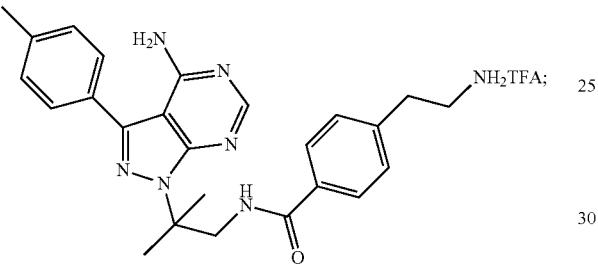
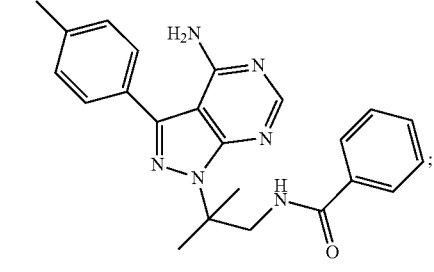
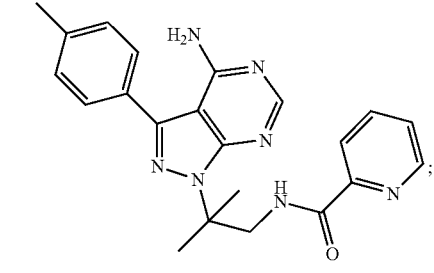
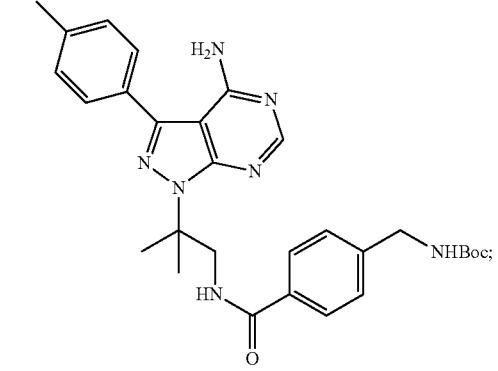
134
-continued
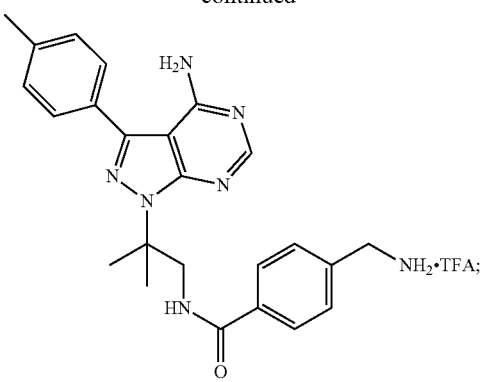
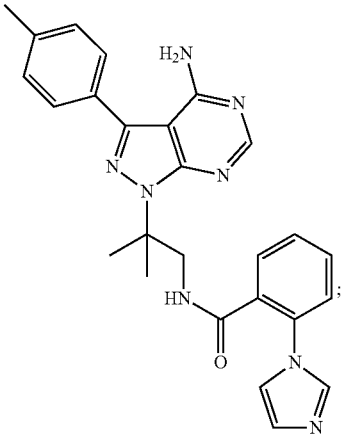
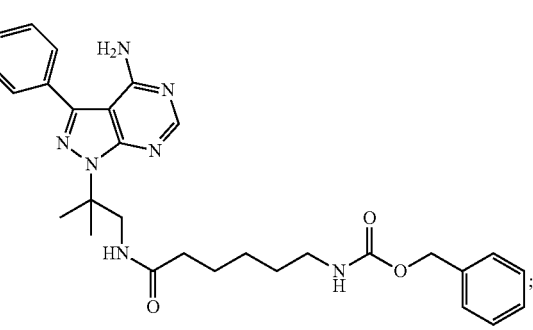
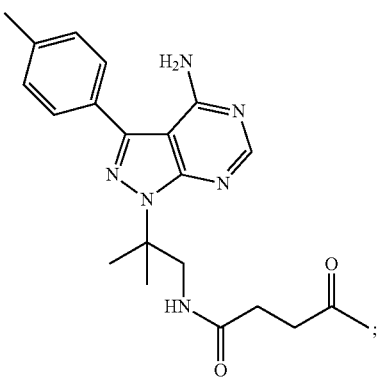

135
-continued
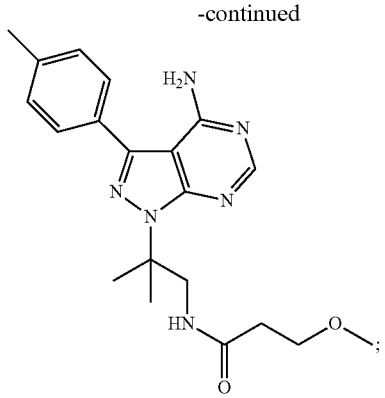
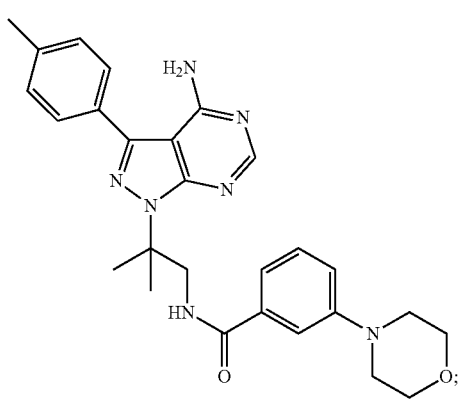
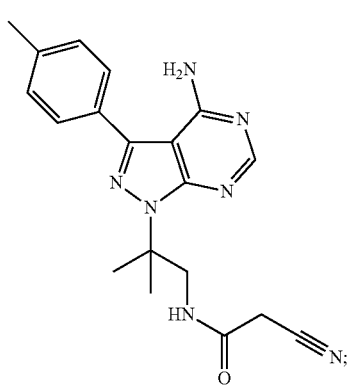
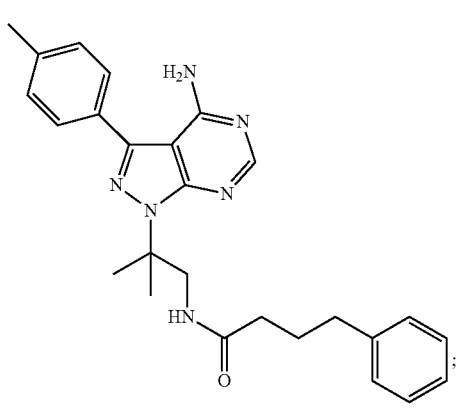
136
-continued
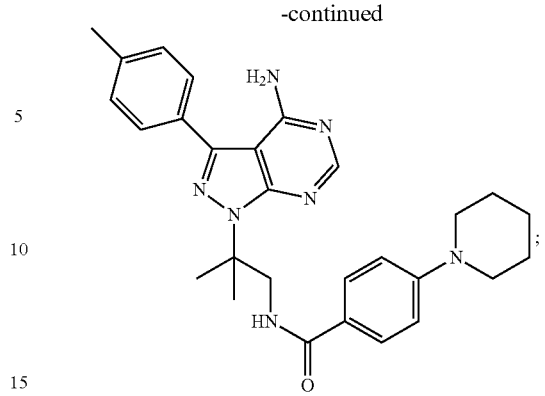
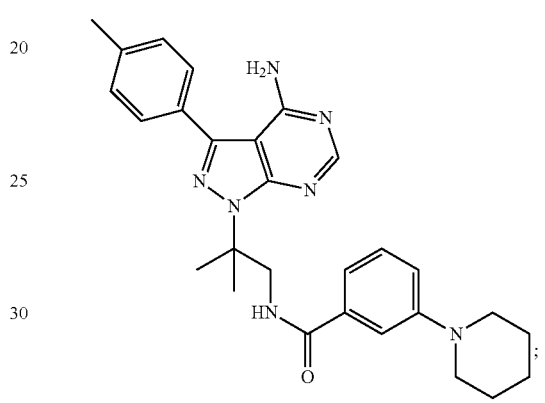
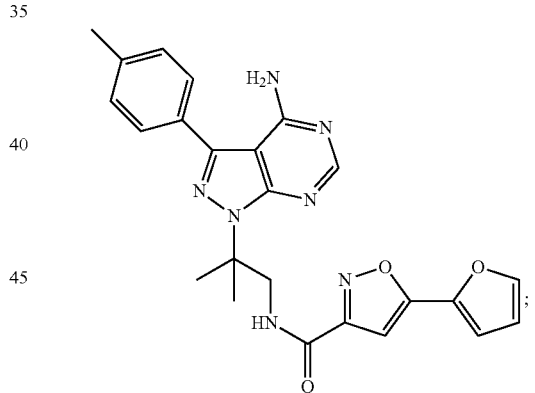
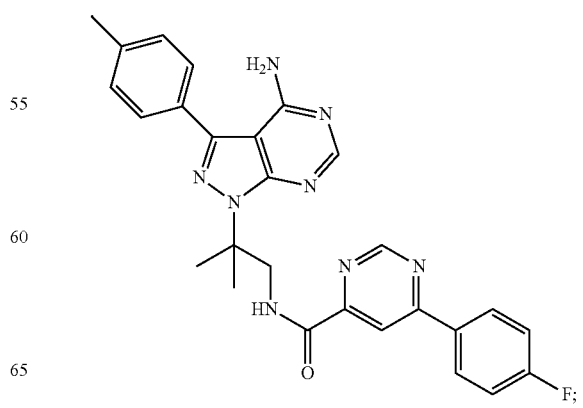

137
-continued
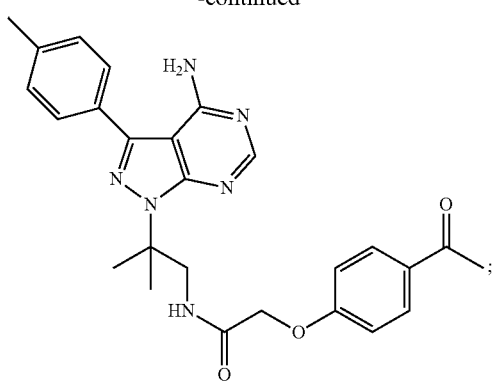
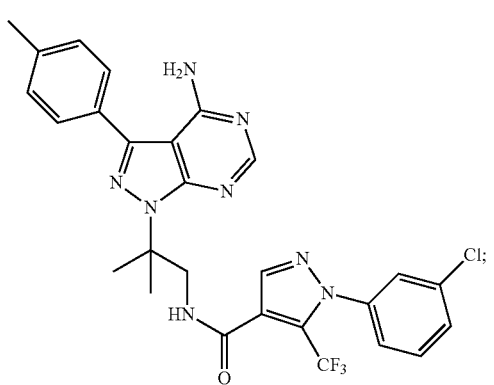
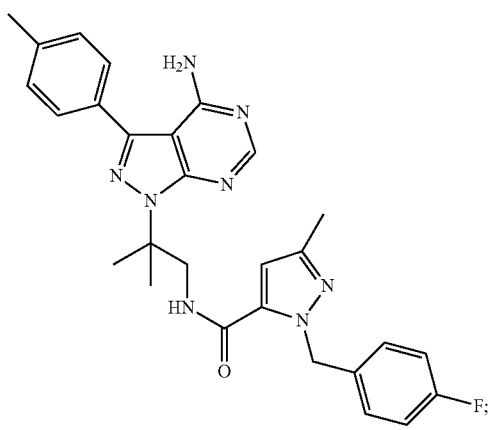
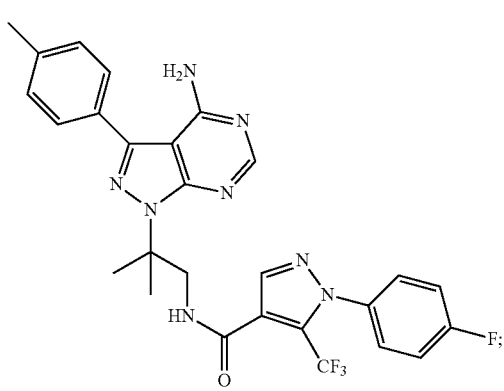
138
-continued
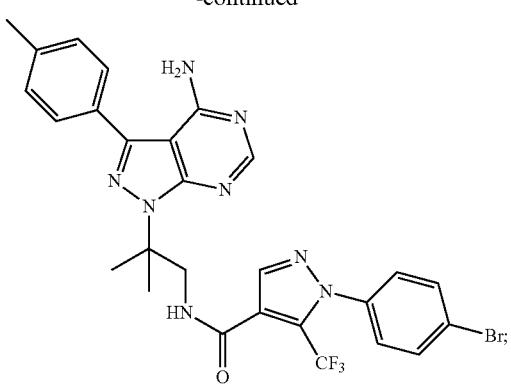
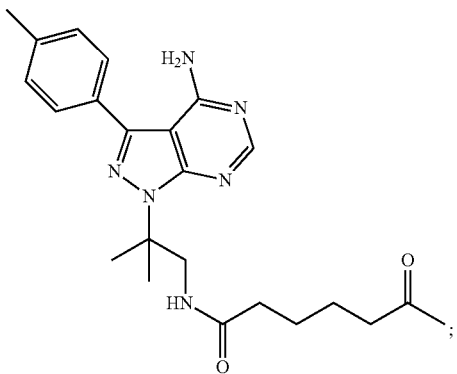
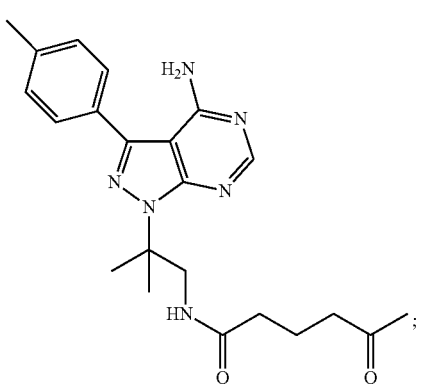
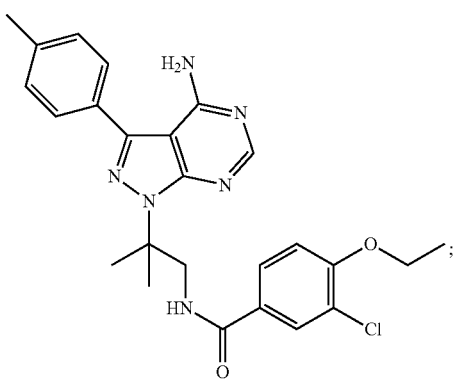

139
-continued
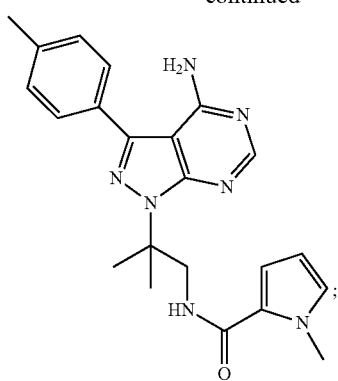
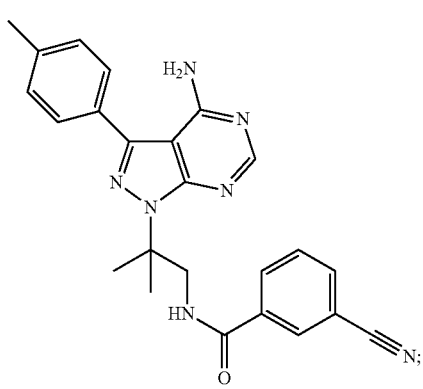
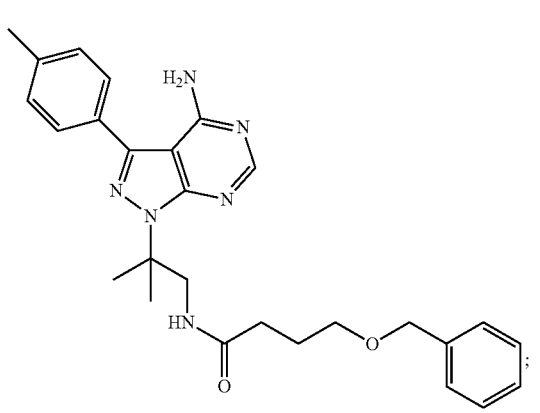
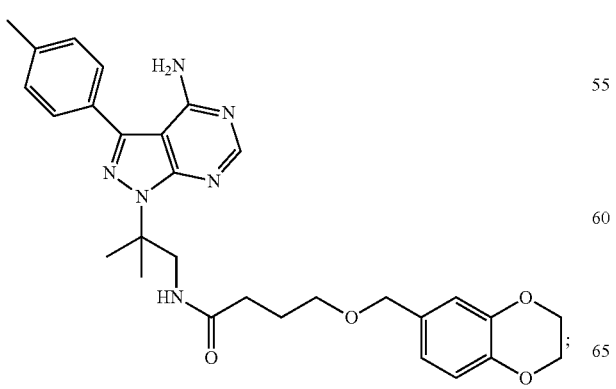
140
-continued
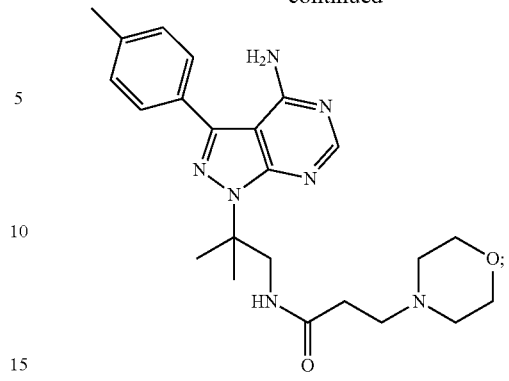
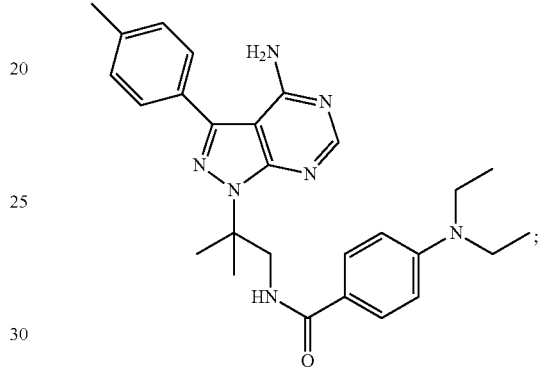
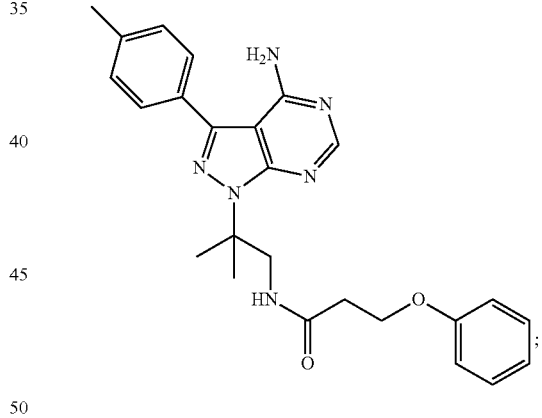
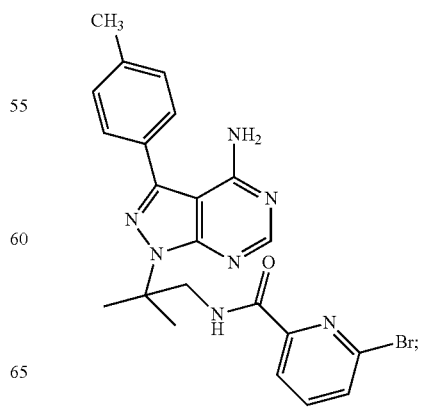

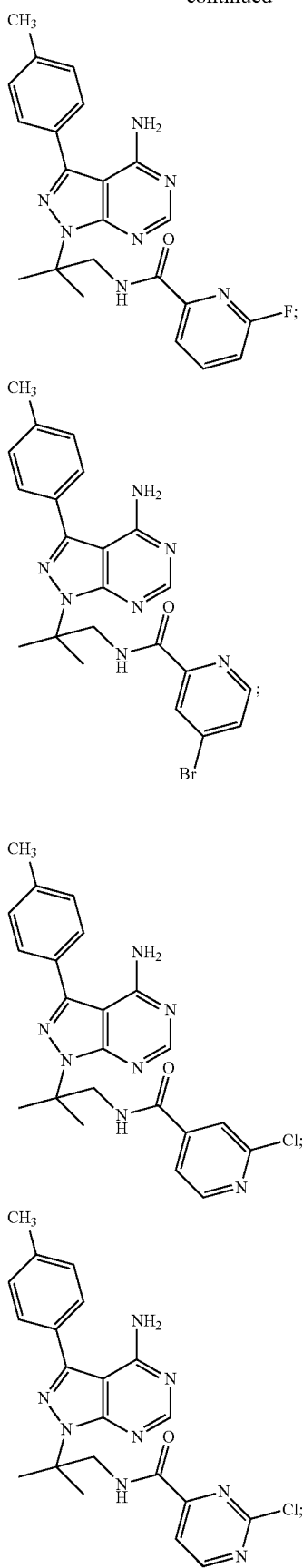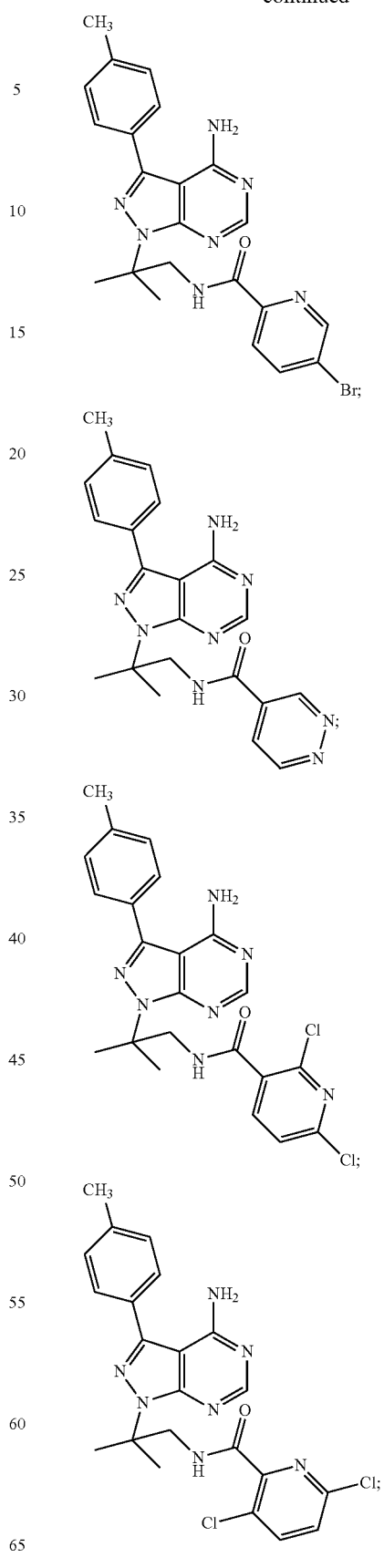

-continued
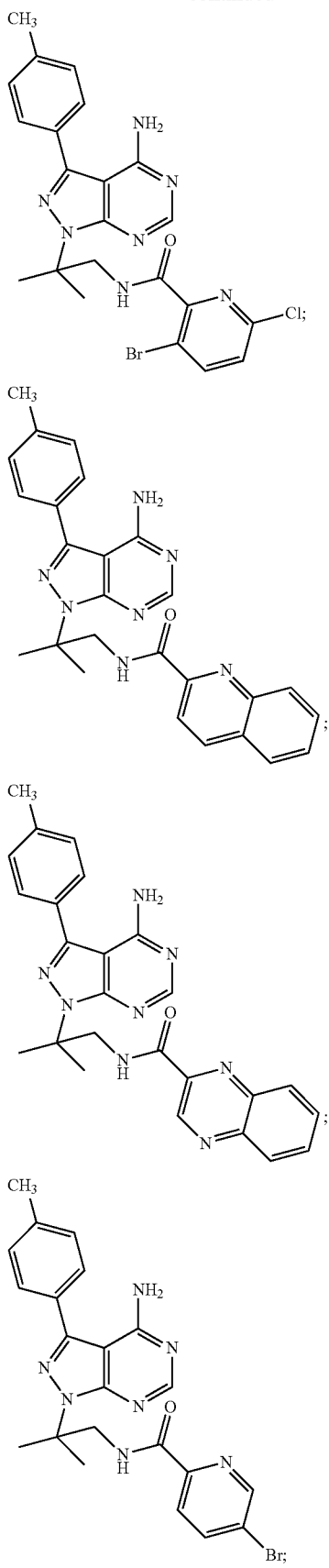
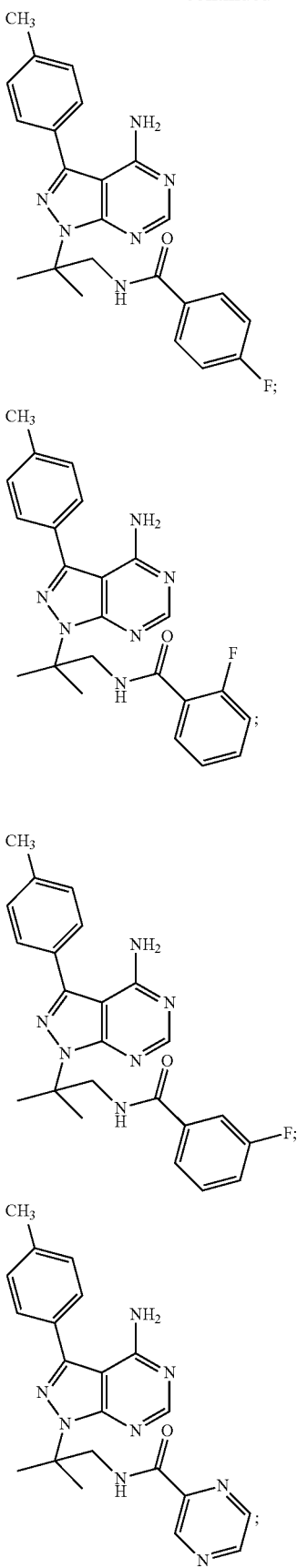

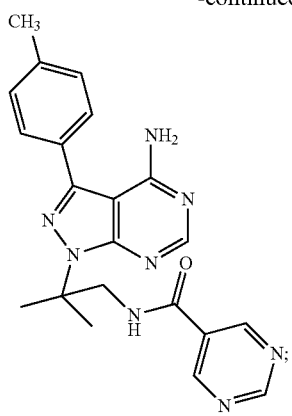
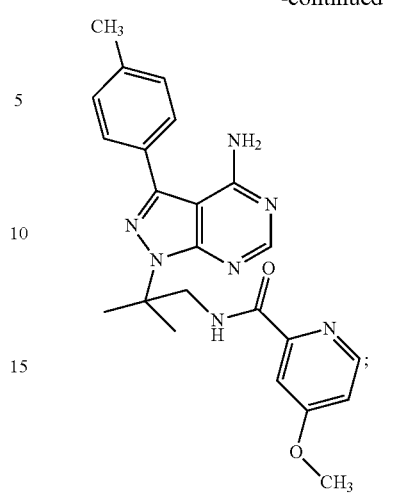
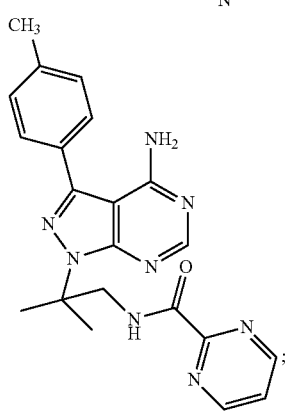
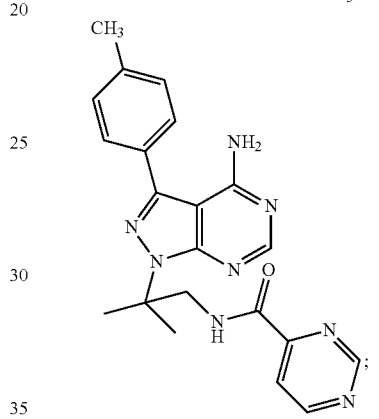
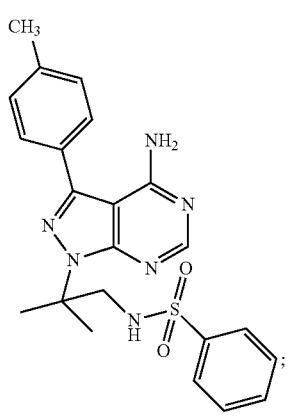
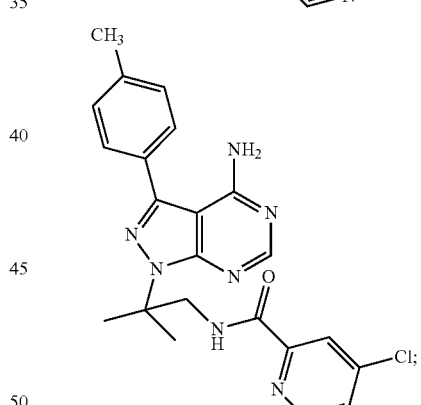
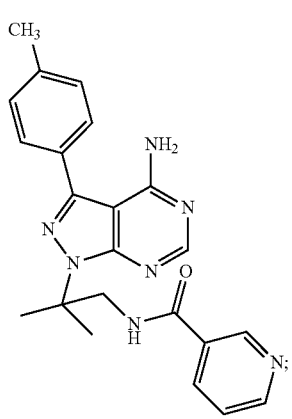
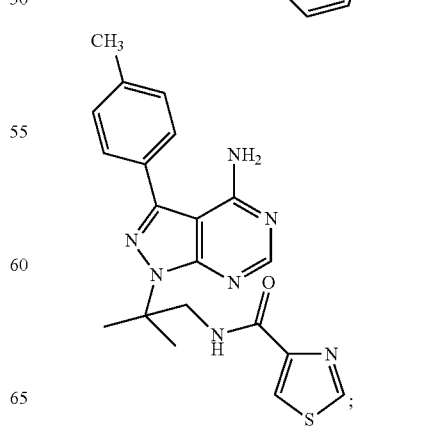

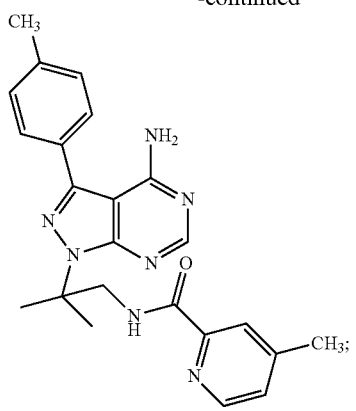
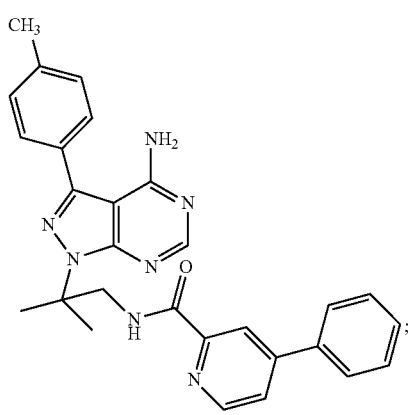
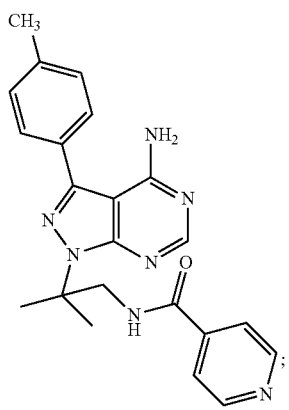
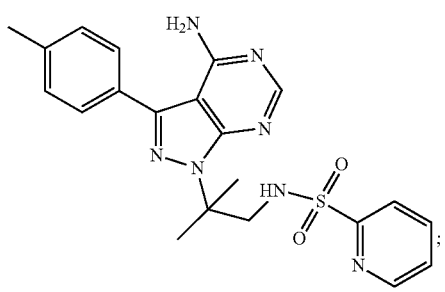
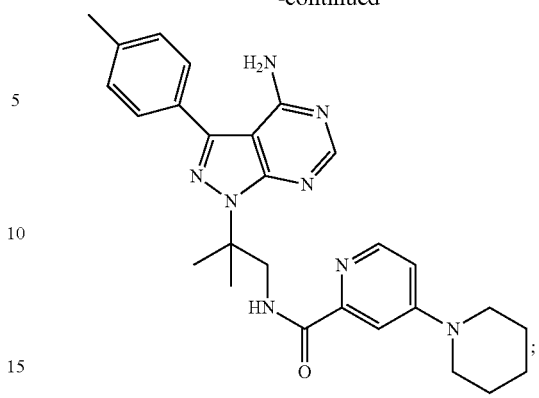
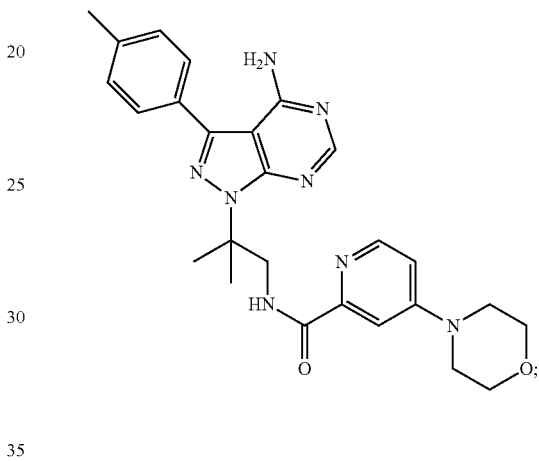
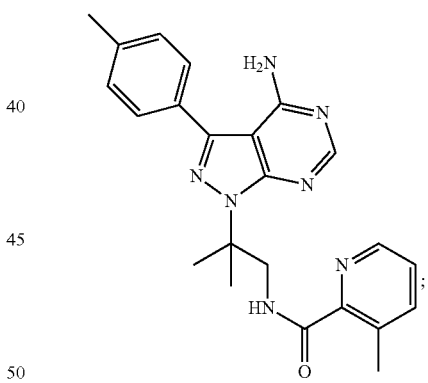
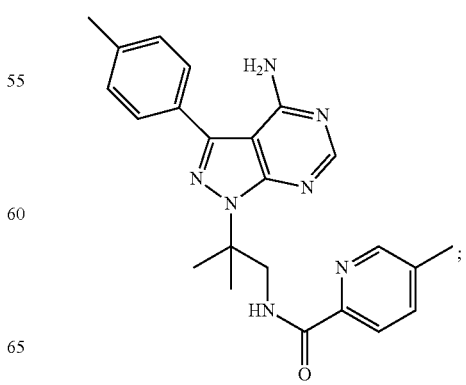

149
-continued
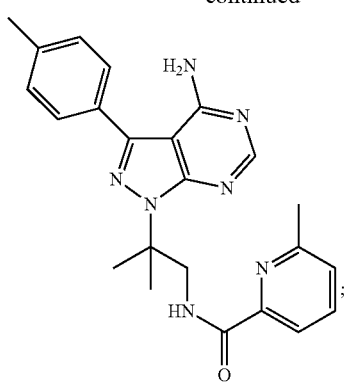
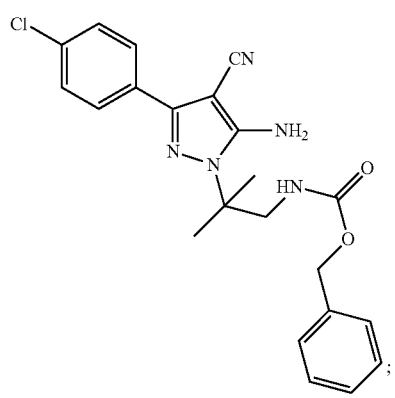
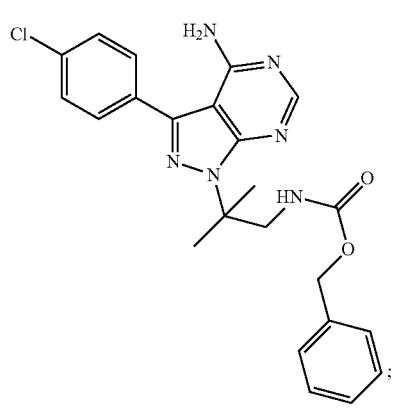
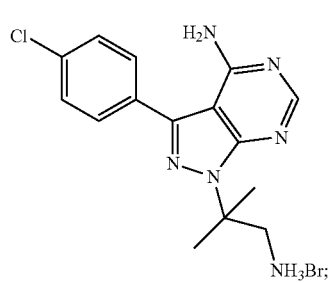
150
-continued
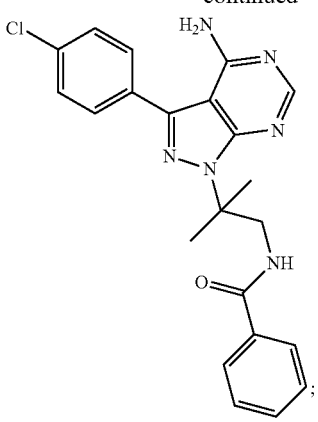
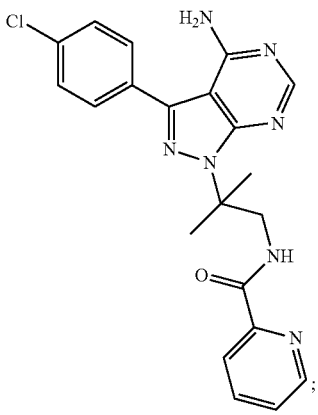
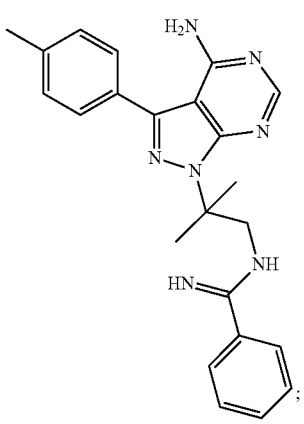
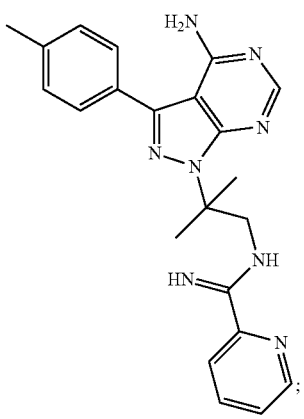

151
-continued
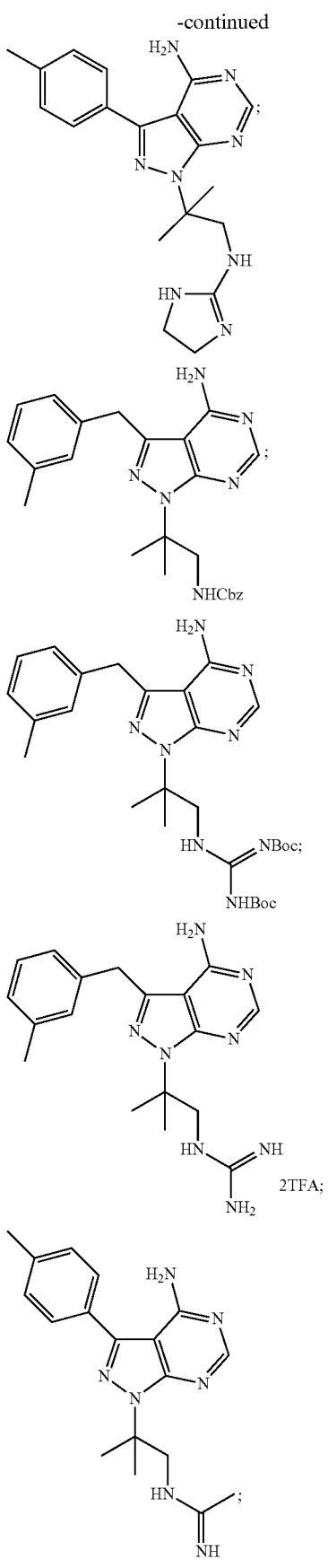
152
-continued
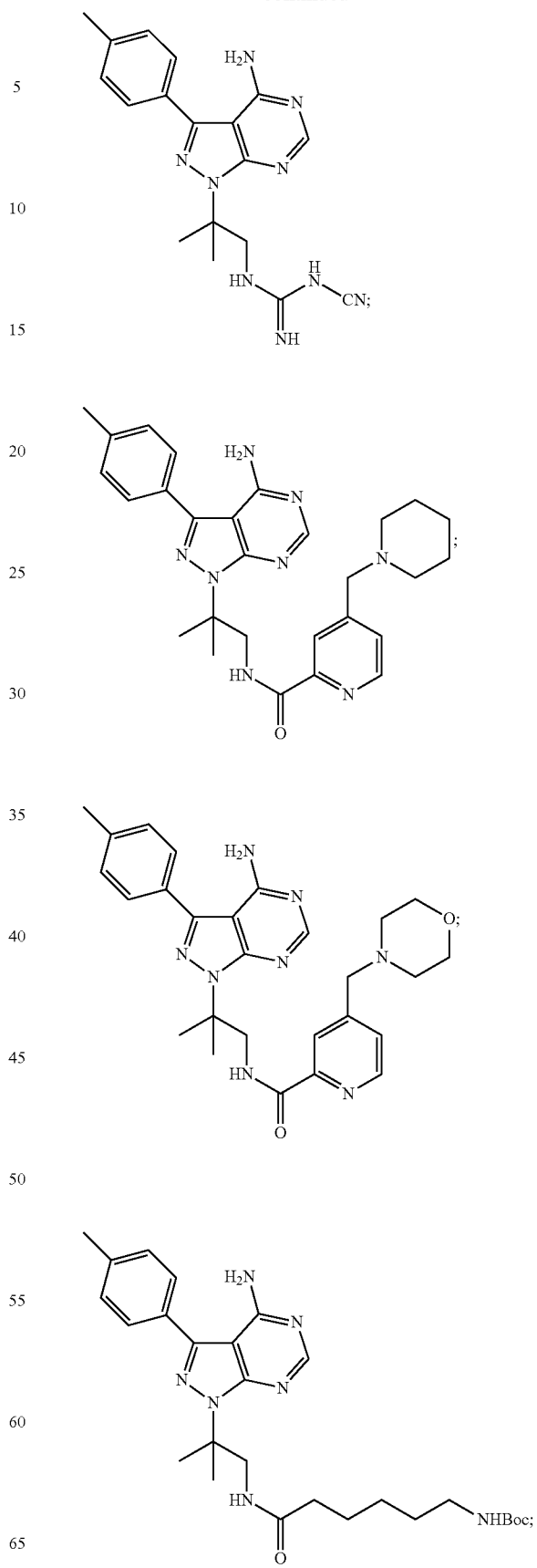

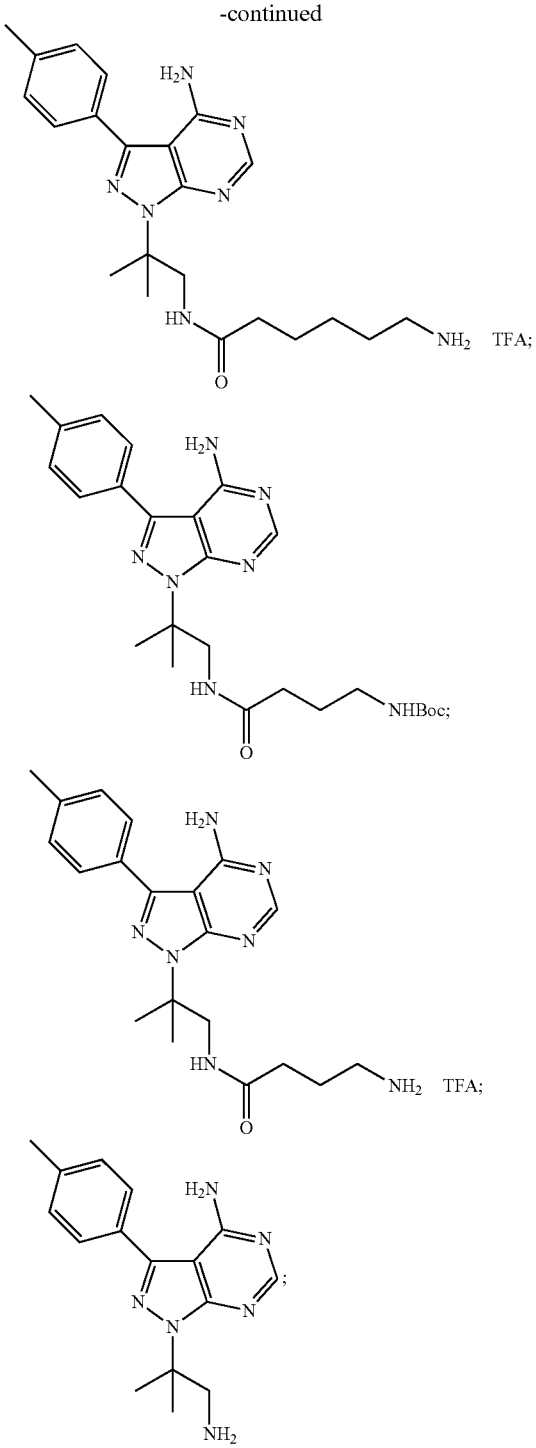

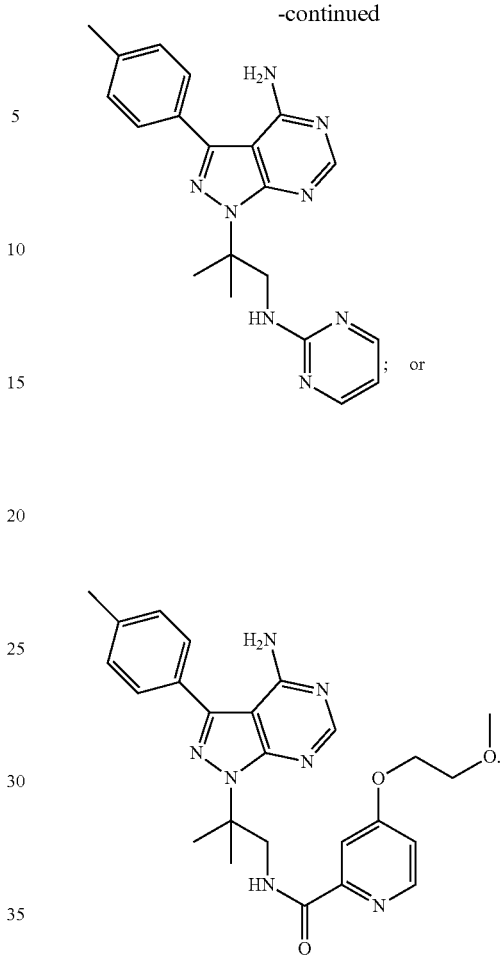

17. A pharmaceutical composition comprising a compound according to claim 1 or claim 16, or a salt thereof, and at least one pharmaceutically acceptable adjuvant, carrier or diluent.

18. A method of treating a tumour comprising administering an effective amount of the compound according to claim 1 or claim 16, or a salt thereof, to a patient in need thereof.

19. The method of claim 18 wherein the tumour is colon cancer.

20. The method of claim 18 wherein the tumour is breast cancer.

21. The method of claim 18 wherein the tumour is lung cancer.

22. The method of claim 18 wherein the tumour is prostate cancer.

* * * * *

UNITED STATES PATENT AND TRADEMARK OFFICE
CERTIFICATE OF CORRECTION

PATENT NO. : 8,962,830 B2  
APPLICATION NO. : 13/809369  
DATED : February 24, 2015  
INVENTOR(S) : Guillaume Laurent Lessene Page 1 of 3

It is certified that error appears in the above-identified patent and that said Letters Patent is hereby corrected as shown below:

In the Specification

Column 15, First structure:

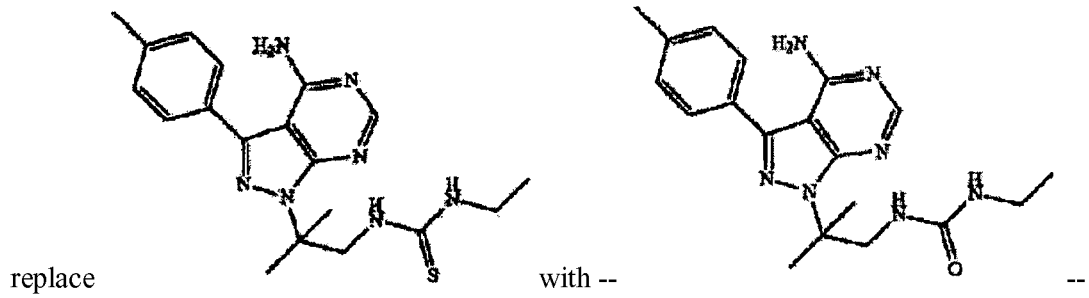

Column 22, Second structure:

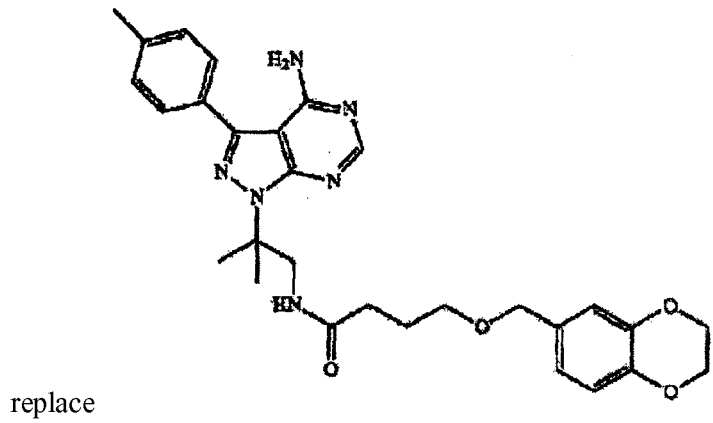

replace

Signed and Sealed this  
Sixteenth Day of June, 2015

Michelle K. Lee  
*Director of the United States Patent and Trademark Office*

CERTIFICATE OF CORRECTION (continued)
U.S. Pat. No. 8,962,830 B2

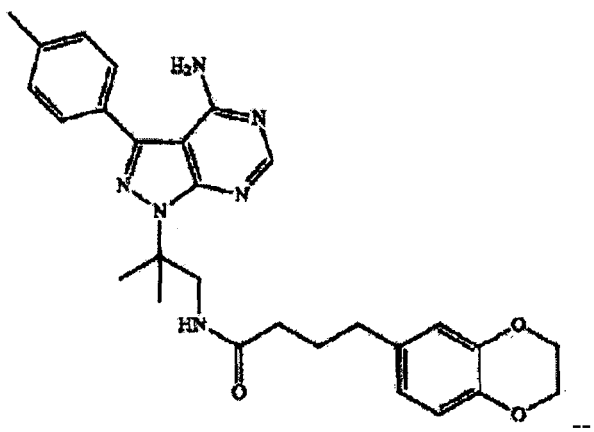

with --                                                            --

In the Claims

Claim 16, Column 132, Fifth structure:

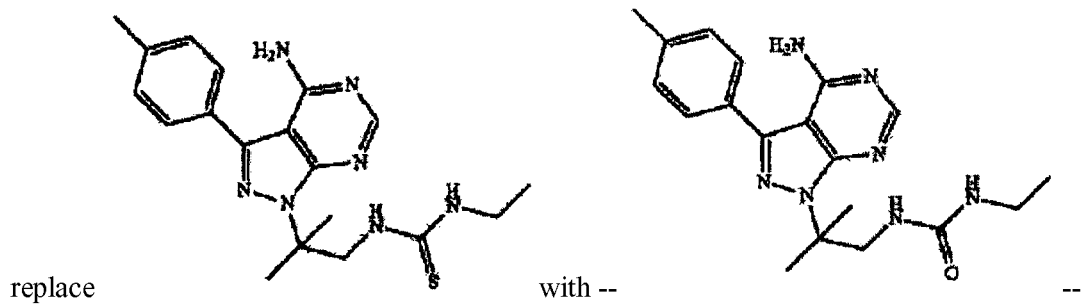

replace                                                with --                                                            --

Claim 16, Column 139, Last structure:

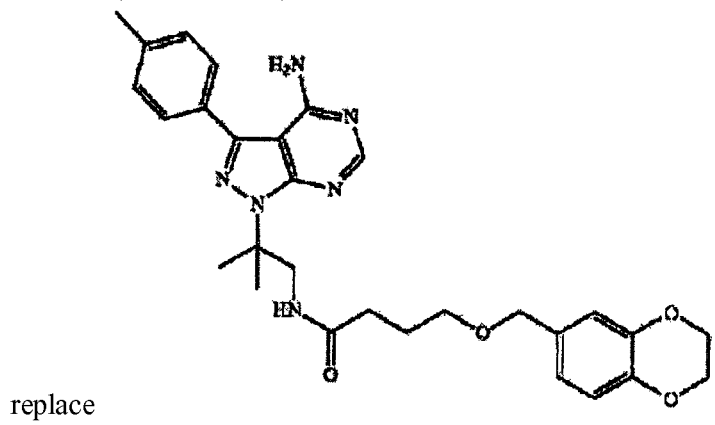

replace

CERTIFICATE OF CORRECTION (continued)
U.S. Pat. No. 8,962,830 B2

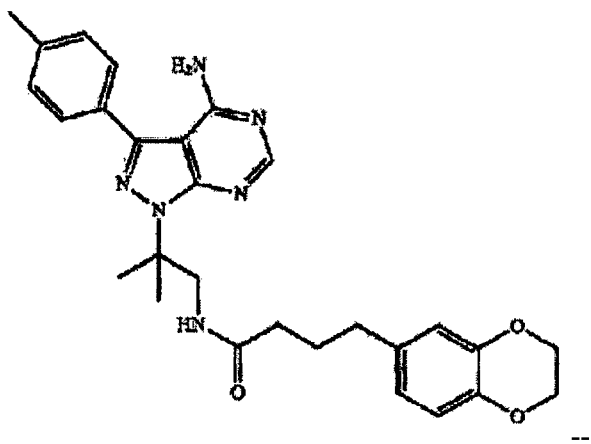

with -- --